US010871489B2

(12) United States Patent
Scoville

(10) Patent No.: US 10,871,489 B2
(45) Date of Patent: Dec. 22, 2020

(54) IMMUNOLOGICALLY ACTIVE POLYPEPTIDE

(71) Applicant: Institute of Arthritis Research, LLC, Idaho Falls, ID (US)

(72) Inventor: Craig D. Scoville, Idaho Falls, ID (US)

(73) Assignee: Institute of Arthritis Research, LLC, Idaho Falls, ID (US)

( * ) Notice: Subject to any disclaimer, the term of this patent is extended or adjusted under 35 U.S.C. 154(b) by 149 days.

(21) Appl. No.: 15/787,234

(22) Filed: Oct. 18, 2017

(65) Prior Publication Data

US 2018/0224447 A1 Aug. 9, 2018

Related U.S. Application Data

(62) Division of application No. 14/206,884, filed on Mar. 12, 2014, now Pat. No. 9,816,989.

(60) Provisional application No. 61/777,568, filed on Mar. 12, 2013.

(51) Int. Cl.
| | |
|---|---|
| *G01N 33/564* | (2006.01) |
| *C07K 14/435* | (2006.01) |
| *C07K 7/08* | (2006.01) |
| *C07K 16/18* | (2006.01) |
| *C07K 7/06* | (2006.01) |
| *C07K 16/28* | (2006.01) |

(52) U.S. Cl.
CPC ............ *G01N 33/564* (2013.01); *C07K 7/06* (2013.01); *C07K 7/08* (2013.01); *C07K 14/435* (2013.01); *C07K 16/18* (2013.01); *C07K 16/2896* (2013.01); *C07K 2317/10* (2013.01); *C07K 2317/21* (2013.01); *C07K 2317/565* (2013.01); *C07K 2317/567* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,646,003 | A | 7/1997 | Barnea et al. |
| 5,981,198 | A | 11/1999 | Barnea et al. |
| 2004/0019187 | A1 | 1/2004 | Nagy et al. |
| 2011/0129473 | A1 | 6/2011 | Paniagua-Solís et al. |

FOREIGN PATENT DOCUMENTS

| | | | | |
|---|---|---|---|---|
| EP | 1642905 A1 | 4/2006 | | |
| WO | 03/004601 A2 | 1/2003 | | |
| WO | 2005/040196 A2 | 5/2005 | | |
| WO | WO-2006029459 A1 | * | 3/2006 | ....... C07K 14/70503 |
| WO | 2007/031741 A1 | 3/2007 | | |
| WO | 2010/132659 A2 | 11/2010 | | |
| WO | 2011/112566 A2 | 9/2011 | | |

OTHER PUBLICATIONS

Kato et al., J Am Soc Nephrol. Jul. 2009;20(7):1565-76. doi: 10.1681/ASN.2008090957. Epub May 14, 2009.*
Cadden et al., "Neutrophils, but not Lymphocytes or Monocytes, Infiltrate Maternal Systemic Vasculature in Women with Preeclampsia," *Hypertens Pregnancy* 27(4):396-405, 2008.
Cardozo et al., "The Neutrophil: The Unnoticed Threat in Xenotransplantation?" *Transplantation* 78(12):1721-1728, 2004.
De Larco et al., "The Potential Role of Neutrophils in Promoting the Metastatic Phenotype of Tumors Releasing Interleukin-8," *Clinical Cancer Research* 10:4895-4900, 2004.
Di Carlo et al., "The intriguing role of polymorphonuclear neutrophils in antitumor reactions," *Blood* 97:339-345, 2001.
Good et al., "Toll-like Receptor 2 Is Required for LPS-induced Toll-like Receptor 4 Signaling and Inhibition of Ion Transport in Renal Thick Ascending Limb," *J. Biol. Chem.* 287:20208-20220, 2012.
Goossens et al., "Frequent occurrence of deletions and duplications during somatic hypermutation: implications for oncogene translocations and heavy chain disease," GenBank Accession No. CAA12632. 1, 8 pages.
Gregory et al., "Tumor-Associated Neutrophils: New Targets for Cancer Therapy," *Cancer Research* 71(7):2411-2416, 2011.
Haruyama et al., "Effects of endometrial IgG on PHA-induced T cell mitogenesis," *Journal of Reproductive Immunology* 19:1-12, 1991.
Kitano et al., "Immunoregulatory Activity in Human Decidua," *Acta Obst Gynaec Jpn* 42(7):739- 746, Jul. 1990.
Kutteh et al., "Quantification of immunoglobulins and cytokines in human cervical mucus during each trimester of pregnancy," *American Journal of Obstetrics and Gynecology* 184(5):865-874, 2001.
Li et al., "Antitumor effects of recombinant human Interleukin-6 on mouse bladder carcinoma through Fas-mediated apoptosis," *Cancer Chemotherapy and Pharmacology* 66:981-986, 2010.
Li et al., "Xenotransplantation: Role of natural immunity," *Transplant Immunology* 21:70-74, 2009.
Lu et al., "Polysaccharide Krestin is a Novel TLR2 Agonist that Mediates Inhibition of Tumor Growth via Stimulation of CD8 T Cells and NK Cells," *Clin Cancer Res* 17:67-76, 2011.
Mantovani et al., "Neutrophils in the activation and regulation of innate and adaptive immunity," *Nature Reviews Immunology* 11:519-531, 2011.

(Continued)

*Primary Examiner* — Michael Szperka
(74) *Attorney, Agent, or Firm* — Seed IP Law Group LLP

(57) ABSTRACT

Disclosed are immunomodulatory polypeptides that elicit an unusual induced cytokine profile, compositions comprising such polypeptides, compositions comprising antibodies that specifically bind to such polypeptides, and methods of using the same, including in cancer treatment, in the treatment of autoimmune diseases, in organ transplantation and for reducing graft rejection, for promoting fertility, and for identifying a neutrophil subset and/or other cellular subset including by flow cytometry. Pharmaceutical compositions and kits, and treatment methods are also disclosed.

2 Claims, 12 Drawing Sheets
Specification includes a Sequence Listing.

(56) References Cited

OTHER PUBLICATIONS

Mitchell et al., "Toll-like receptor-mediated adjuvanticity and immunomodulation in dendritic cells," *Human Vaccines* 7 (Suppl.):85-93, 2011.

Müller et al., "Polymorphonuclear neutrophils and T lymphocytes: strange bedfellows or brothers in arms?" *Trends in Immunology* 30:522-530, 2009.

Mumm et al., "IL-10 Elicits IFNγ-Dependent Tumor Immune Surveillance," *Cancer Cell* 20:781-796, 2011.

Park et al., "Human immunoglobulin heavy chain variable regions," GenBank Accession No. ADW08230.1, Mar. 1, 2011, 13 pages.

Rodriguez et al., "Arginase I-Producing Myeloid-Derived Suppressor Cells in Renal Cell Carcinoma Are a Subpopulation of Activated Granulocytes," *Cancer Research* 69(4): 1553-1560, 2009.

Soehnlien, "An elegant defense: how neutrophils shape the immune response," *Trends in Immunology* 30:511-512, 2009.

Soo et al., "Pre-operative Determination of an Individual's Neutrophil Response: A Potential Predictor of Early Cardiac Transplant Cellular Rejection," *Journal of Heart and Lung Transplantation* 28:1198-1205, 2009.

Strausberg et al., "Generation and initial analysis of more than 15,000 full-length human and mouse cDNA sequences," GenBank Accession No. AAH90938, Jul. 28, 2005, 2 pages.

Sweeney et al., "A Toll-Like Receptor 2 Pathway Regulates the Ppargc 1a/b Metabolic Co-Activators in Mice with *Staphylococcal aureus* Sepsis," *PLoS One* 6(9), 12 pages, 2011.

Vasconcelos et al., "G-CSF-treated granulocytes inhibit acute graft-versus-host disease," *Blood* 107(5):2192-2199, 2006.

Verleden et al., "Interleukin-17 and Neutrophils Are Increased in BAL Fluid During Acute Lung Rejection," *Chest* 131(6):1988-1989, 2007.

\* cited by examiner

IMMUNOLOGICALLY ACTIVE POLYPEPTIDE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 750061_402D1_SEQUENCE_LISTING.txt. The text file is 112 KB, was created on Oct. 15, 2017, and is being submitted electronically via EFS-Web.

BACKGROUND

Technical Field

The presently disclosed invention embodiments relate generally to immunomodulatory polypeptides, compositions comprising such polypeptides, and methods of using the same.

Description of the Related Art

Cancer remains a devastating and largely intractable disease with significant unmet needs in the areas of patient treatment, clinical outcome and overall survival. The American Cancer Society (ACS) estimates that there will be over 1.6 million new cases of cancer diagnosed in the United States in 2012, not including non-invasive carcinoma in situ and also not including new cases of basal cell carcinoma and squamous cell skin cancer. The ACS also projects that there will be 577,190 cancer-related deaths in 2012, or an average of 1500 Americans dying each day from cancer, making cancer the second most common cause of death in the U.S., after heart disease. In 2007 the total medical cost of cancer in the U.S. was $226.8 billion, including direct medical costs for treatment of $103.8 billion and indirect costs due to lost productivity and premature death of $123 billion. The mean five-year survival rate overall for U.S. cancer patients has improved from 49% in 1975-1977 to 67% in 2001-2007. There clearly, however, still remains a pressing need for improved treatments and enhanced overall outcomes for cancer patients.

Organ transplantation is often the best or only treatment option for end-stage organ failure, such as kidney disease, chronic conditions such as severe cirrhosis of the liver, and cancer, such as liver cancer, leukemias and lymphomas. Both solid organ and bone marrow transplants are performed in order to treat patients in need. It is estimated that about 100,000 solid organ transplants were performed worldwide in 2007, and of the roughly 30,000 bone marrow transplants performed annually, about 15,000 are allogenic transplants. Kidney, liver and heart transplants are the most common solid organ transplants.

The worldwide demand for donor tissues and organs far surpasses the supply, and there is a significant need in transplantation medicine to improve the availability of donor organs and minimize the long term risk of rejection. For example, the World Health Organization (WHO) has estimated that only 10% of those in need of kidney transplants manage to get one. The National Kidney Foundation claims that about 18 patients die daily while waiting for a transplant of a vital organ such as a heart, liver, kidney, pancreas, lung, or bone marrow. Furthermore the long-term graft survival rates for kidney and liver transplants are about 60-70% at 5-10 years post-transplant.

Rejection of the donor tissue by the host immune system is one of the largest problems faced in allogenic transplants. Despite donor-recipient human leukocyte antigen (HLA) histocompatibility matching and ABO blood group testing to provide matched donor tissue to the recipient, patients receiving transplants must undergo immunosuppressive treatment in an effort to prevent graft rejection or, in the case of bone marrow transplants, graft-versus-host disease (GVHD). Most immunosuppressors target T cells or cytokines secreted by T cells, and types of immunosuppressive agents currently used include monoclonal antibodies to lymphocytes and cytokine receptors (e.g., anti-IL-2Rα), calcineurin inhibitors (e.g., cyclosporine and tacrolimus), and cytokine receptor signal transduction inhibitors (e.g., sirolimus) (Chinen and Buckley, *J Allergy Clin Immunol*, 2010, 125(2 Suppl 2):S324-S335). The downside to using immunosuppressive agents, sometimes over a course of several months, is that while protecting the graft from being rejected by the host immune system, or vice versa in the case of GVHD, they make the recipient especially vulnerable to infections and malignancies.

In addition, despite advances in immunosuppressive treatments which have significantly improved first year graft survival, long-term survival is still unsatisfactory. In a study of long term kidney graft survival, Fernandez-Rodriguez et al (*Transplantation Proceedings* 2009 41(6): 2357-2359) followed 1,029 first renal transplantations performed between November 1979 and December 2007, observed renal graft survival at 1, 5 and 10 years and correlated the results to the immunosuppressive therapy used, including azathioprine (AZA), cyclosporine (CsA), and tacrolimus (TAC). The findings indicated that graft survival rates at 5 and 10 years post-transplant were, respectively, 56% and 46% on AZA, 69% and 54% on CsA, and 77% and 60% on TAC. The study concluded that despite the decrease in acute rejection in kidney transplants, there was a significant decrease in renal graft survival after 12 months. Another study by Ruiz et al (*Arch Surg* 2006 141:735-742) reported liver graft survival at 1, 3 and 5 years post-transplant of 70%, 65% and 65%, respectively, and kidney graft survival at 1, 3 and 5 years post-transplant of 76%, 72% and 70%, respectively, thereby demonstrating that there is a significant decrease in graft survival following the first year.

As a semi-allograft, the maternal-host acceptance and tolerance of an embryo and placenta is similar in many ways to an allogeneic organ transplant. Implantation of the blastocyst into the uterine wall is a critical checkpoint for a successful pregnancy and results in the embryo adhering to the uterine lining and generating a vascular connection. Implantation failure can result in repeated miscarriages and failed in vitro fertilization (IVF) attempts. In particular, embryo implantation success rates in IVF patients vary widely, and success rates ranging from about 15% to about 30% have been reported (see, e.g., Croo et al. *Human Reproduction*, 15(6):1383-1388, 2000). Inflammation and the mother's immune response are believed to play a role in the successful implantation of an embryo.

Inflammation also plays a role later on in pregnancy, such as in preeclampsia and eclampsia, which affect an estimated 5-8% of all pregnancies and are the leading cause of maternal and fetal illness and mortality worldwide. Preeclampsia is characterized by high blood pressure and proteinuria, and if left unchecked, it can lead to the seizures of eclampsia. During pregnancy, the maternal adaptive immune response is down-regulated, and the innate immune response is enhanced. However, the innate immunity also must be regulated, and it has been shown that neutrophils, non-antigen specific white blood cells of hematopoietic origin that are typically associated with inflammatory and anti-microbial responses, play a large role in preeclampsia (Cadden and Walsh, *Hypertens Pregnancy* (2008) 27(4): 396-405).

Indeed, studies indicate that innate immune cells, such as neutrophils (often referred to as polymorphonuclear neutrophils, or PMN), are important in shaping, enhancing and regulating the adaptive immune response (see, e.g., Soehnlein, *Trends in Immunology,* 2009, 30(11):511-512 and Müller et al, *Trends in Immunology,* 2009, 30(11):522-530). Recent studies indicate that neutrophils may play a significant role in antitumor reactions (DiCarlo et al., 2001 *Blood* 97:339; Mumm et al., 2011 *Canc. Cell* 20:781) and in transplant rejection, in addition to the historical role of lymphocytes. In particular, Soo et al. (*J. Heart and Lung Transplantation,* 2009, 28(11):1198-1205) examined pre-operative neutrophil adhesion molecule expression after in vitro stimulation with LPS or PMA and then correlated these results with actual allograft success. Interestingly, pre-operative neutrophil surface CD11b expression after LPS stimulation correlated proportionally with the degree of rejection as detected in the first endomyocardial biopsy sample post heart transplantation, and the authors concluded "that neutrophils may contribute more to cardiac allograft rejection than previously thought."

Another study identified increased IL-17 and neutrophilia in the broncho-alveolar lavage of patients undergoing acute lung transplant rejection (*Chest* 2007 131(6):1988-9). Furthermore, neutrophils have been shown to play a significant role in xenotransplantation rejection (*Transplant Immunology* 2009 21:70-74, *Transplantation* 2004 78: 1721-1718), and means of attenuating neutrophil activity may play a significant role in improving the success of this type of transplantation approach. There is also increasing evidence that neutrophils can be activated to express MHC Class II molecules and develop antigen presenting cell (APC) characteristics and release cytokines such as IL-4, IL6, IL-10, IL-12, and TNFa and suppress T cell activity (e.g., Muller et al., 2009 *Trends in Immunology* 30(11):522-530, 2009; Vasconcelos et al., 2006 *Blood* 107:2192-2199; Rodriguez et al., 2009 *Cancer Research* 69:1553-1560, 2009. Therefore the role of neutrophils may also be involved in allograft and xenograft acceptance.

Neutrophils are clearly of interest for research due to their role in inflammation and infection as well as other immune functions, including roles in pregnancy, transplantation and autoimmunity. A number of cell surface markers present on neutrophils have been utilized in an effort to characterize, identify and determine their activation state, such as CD64, CD11b, and CD83; however few neutrophil markers exist that can readily be used to identify a distinct subset of neutrophils in the same way that other hematopoietic cell surface markers can be used to categorize adaptive immune cells, for instance, according to maturational state, differentiation lineage, and functional properties (e.g., CD4 versus CD8 T lymphocytes, surface immunoglobulin (sIg) changes in B lymphocyte differentiation and maturation, and other regulatory cell markers, e.g., CD45 isoforms, distinct integrin α and β chain heterodimer expression, etc.). Accordingly, a need exists for more refined neutrophil markers in order to functionally characterize these cells. (See, e.g., Mason et al., (Eds.), *Leukocyte Typing VII,* 2002 Oxford Univ. Press, USA.)

An increased understanding of the mechanisms resulting in graft rejection have lead to advancements in the availability and mechanistic understanding of immunosuppressants; however, there is still a significant medical need for immunosuppressive agents that are capable of improving the acceptance of donor organs and minimizing the risk of rejection while at the same time placing recipients at a lesser risk of infections and malignancies. In particular, there is an unmet need for treatments that improve long term graft survival and also improve the success of xenotransplantation. In addition, immunosuppressive agents that are useful for conception, providing improved rates of implantation and a reduced risk of multiples, as well as preventing conditions like preeclampsia, are needed.

The compositions and methods of certain presently disclosed invention embodiments address the needs described above and offer other related advantages.

BRIEF SUMMARY

According to certain embodiments of the invention disclosed herein, there is provided an isolated immunomodulatory polypeptide of no more than 31, 30, 29, 28, 27, 26, 25, 24, 23, 22, 21, 20, 19, 18, 17, 16, 15, 14, 13 or 12 amino acids, which comprises either (i) the amino acid sequence KSIAYLQMNSLK as set forth in SEQ ID NO:2, or (ii) the amino acid sequence of general formula: K-X1-X2-X3-YLQM-X4-X5-LK as set forth in SEQ ID NO:106, wherein X1 is selected from S and N, X2 is selected from I, T, S, M, R and N, X3 is selected from A, L, V and Q, X4 is selected from N, D, S, T and A, and X5 is selected from S, T and N. In certain further embodiments the polypeptide comprises up to 23 contiguous amino acids of the amino acid sequence set forth in any one of SEQ ID NOS:3 and 5-104, said 23 contiguous amino acids including the amino acid sequence KSIAYLQMNSLK as set forth in SEQ ID NO:2. In certain other further embodiments the immunomodulatory polypeptide of claim 1 which comprises no more than 22, 21, 20, 19, 18, 17, 16, 15, 14, 13 or 12 contiguous amino acids. In another embodiment there is provided an isolated polynucleotide comprising a nucleic acid sequence that encodes any of the just-described immunomodulatory polypeptides. In certain other embodiments there is provided an expression vector comprising the polynucleotide. In certain other embodiments there is provided a host cell transformed or transfected with the expression vector.

In certain other embodiments there is provided a method of producing an immunomodulatory polypeptide of no more than 31, 30, 29, 28, 27, 26, 25, 24, 23, 22, 21, 20, 19, 18, 17, 16, 15, 14, 13 or 12 amino acids that comprises the amino acid sequence set forth in SEQ ID NO:2 or in SEQ ID NO:106, the method comprising the steps of a) culturing the above described host cell under conditions and for a time sufficient to permit expression of the immunomodulatory polypeptide; and b) isolating the immunomodulatory polypeptide from the cultured host cell. In another embodiment there is provided a pharmaceutical composition, comprising a) an immunomodulatory polypeptide of no more than 31, 30, 29, 28, 27, 26, 25, 24, 23, 22, 21, 20, 19, 18, 17, 16, 15, 14, 13 or 12 amino acids, comprising the amino acid sequence set forth in either SEQ ID NO:2 or in SEQ ID NO:106; and b) a physiologically acceptable carrier. In another embodiment there is provided an isolated antisense polynucleotide comprising a nucleic acid sequence that is complementary to the polynucleotide described above and herein. In another embodiment there is provided an isolated small interfering RNA (siRNA) polynucleotide that is capable of substantially silencing, and is complementary to a region of 18-69 contiguous nucleotides in, a nucleic acid which encodes the immunomodulatory polypeptide that comprises up to 23 contiguous amino acids of the amino acid sequence set forth in any one of SEQ ID NOS:3 and 5-104, said 23 contiguous amino acids including the amino acid sequence KSIAYLQMNSLK as set forth in SEQ ID NO:2. Certain other embodiments provide an isolated ribozyme that specifically binds to the polynucleotide described above and herein.

Certain other embodiments provide an isolated antibody, or antigen-binding fragment thereof, that specifically binds to an immunomodulatory polypeptide of no more than 31, 30, 29, 28, 27, 26, 25, 24, 23, 22, 21, 20, 19, 18, 17, 16, 15, 14, 13 or 12 amino acids, the immunomodulatory polypeptide comprising the amino acid sequence set forth in SEQ ID NO:2 or in SEQ ID NO:106. In certain embodiments the antibody is a monoclonal antibody.

In certain embodiments there is provided a pharmaceutical composition comprising the just-described antibody and a physiologically acceptable carrier. According to certain embodiments there is provided a method for detecting, in a biological sample, an immunomodulatory polypeptide of no more than 31, 30, 29, 28, 27, 26, 25, 24, 23, 22, 21, 20, 19, 18, 17, 16, 15, 14, 13 or 12 amino acids that comprises the amino acid sequence set forth in SEQ ID NO:2 or in SEQ ID NO:106, said method comprising the steps of: a) contacting the biological sample with an antibody that specifically binds said immunomodulatory polypeptide, or an antigen-binding fragment of said antibody, under conditions and for a time sufficient for specific antibody binding to the immunomodulatory polypeptide to take place; and b) detecting specific binding of the antibody to the immunomodulatory peptide, and thereby detecting the immunomodulatory peptide in the sample. In certain further embodiments the antibody is linked to a support material. In certain other further embodiments the antibody is linked to a detectable label. In certain other further embodiments the biological sample is obtained from a subject that is selected from a human, a non-human primate, a non-primate mammal, a non-mammalian vertebrate, an invertebrate eukaryote and a prokaryote.

In certain embodiments there is provided a pharmaceutical composition, comprising a) an immunomodulatory polypeptide of no more than 31, 30, 29, 28, 27, 26, 25, 24, 23, 22, 21, 20, 19, 18, 17, 16, 15, 14, 13 or 12 amino acids comprising the amino acid sequence set forth in SEQ ID NO:2 or in SEQ ID NO:106; and b) a physiologically acceptable carrier.

In certain embodiments there is provided a method for detecting, in a biological sample that comprises one or a plurality of nucleic acid molecules, expression of a polynucleotide that encodes an immunomodulatory polypeptide of no more than 31, 30, 29, 28, 27, 26, 25, 24, 23, 22, 21, 20, 19, 18, 17, 16, 15, 14, 13 or 12 amino acids, comprising the amino acid sequence set forth in SEQ ID NO:2 or in SEQ ID NO:106, said method comprising the steps of a) contacting the sample with at least one of (i) the antisense polynucleotide of claim 9, and (ii) the polynucleotide of claim 4, under conditions and for a time sufficient for specific nucleic acid hybridization to occur; and b) detecting specific hybridization of at least one nucleic acid to at least one of said antisense polynucleotide and said polynucleotide of claim 4, and thereby detecting, in the sample, expression of the polynucleotide that encodes the immunomodulatory peptide. In certain further embodiments the biological sample is obtained from a subject that is selected from a human, a non-human primate, a non-primate mammal, a non-mammalian vertebrate, an invertebrate eukaryote and a prokaryote.

In another embodiment there is provided a fusion protein comprising an immunomodulatory polypeptide that comprises up to 23 contiguous amino acids of the amino acid sequence set forth in any one of SEQ ID NOS:3 and 5-104, said 23 contiguous amino acids including the amino acid sequence KSIAYLQMNSLK as set forth in SEQ ID NO:2 or the amino acid sequence set forth in SEQ ID NO:106, fused to a fusion polypeptide domain. In certain further embodiments there is provided a pharmaceutical composition comprising the fusion protein; and a physiologically acceptable carrier.

In another embodiment there is provided a method of treating or preventing graft rejection in a transplant patient, comprising administering a therapeutically effective amount of an immunomodulatory polypeptide comprising the amino acid sequence set forth in SEQ ID NO:2 or in SEQ ID NO:106. In certain embodiments the transplant is selected from kidney, heart, liver, pancreas and lung. In another embodiment there is provided a method of treating or preventing graft versus host disease in a bone marrow transplant patient, comprising administering a therapeutically effective amount of an immunomodulatory polypeptide comprising the amino acid sequence set forth in SEQ ID NO:2 or in SEQ ID NO:106. In another embodiment there is provided a method of treating preeclampsia in a patient, comprising administering a therapeutically effective amount of an immunomodulatory polypeptide comprising the amino acid sequence set forth in SEQ ID NO:2 or in SEQ ID NO:106. In another embodiment there is provided a method of treating or preventing eclampsia in a patient, comprising administering a therapeutically effective amount of an immunomodulatory polypeptide comprising the amino acid sequence set forth in SEQ ID NO:2 or in SEQ ID NO:106. In certain further embodiments the patient has been diagnosed with severe preeclampsia. In another embodiment there is provided a method of treating or preventing HELLP syndrome in a patient, comprising administering a therapeutically effective amount of an immunomodulatory polypeptide comprising the amino acid sequence set forth in SEQ ID NO:2 or in SEQ ID NO:106. In certain further embodiments, the patient has been diagnosed with severe preeclampsia.

In another embodiment there is provided a method of treating rheumatoid arthritis in a patient, comprising administering a therapeutically effective amount of an immunomodulatory polypeptide comprising the amino acid sequence set forth in SEQ ID NO:2 or in SEQ ID NO:106.

In another embodiment there is provided a method of inducing a peripheral blood white cell response that includes cellular release of at least one of IL-6, IL-10 and TNFα, comprising contacting one or a plurality of peripheral blood white cells in vitro or in vivo with an immunomodulatory polypeptide comprising the amino acid sequence set forth in SEQ ID NO:2 or in SEQ ID NO:106, under conditions and for a time sufficient to induce detectable cellular release of at least one of IL-6, IL-10 and TNFα. In another embodiment there is provided a method of treating an organ to be transplanted into an allogeneic recipient to reduce a likelihood or severity of allograft rejection by the recipient, comprising contacting the organ with an immunomodulatory polypeptide comprising the amino acid sequence set forth in SEQ ID NO:2 or in SEQ ID NO:106, under conditions and for a time sufficient to reduce the likelihood or severity of allograft rejection. In another embodiment there is provided a method of promoting implantation of an embryo in a pregnant or pseudopregnant mammal, comprising contacting at least one of the embryo and the pregnant or pseudopregnant mammal with an immunomodulatory polypeptide comprising the amino acid sequence set forth in SEQ ID NO:2 or in SEQ ID NO:106, under conditions and for a time sufficient to promote embryonic implantation. In certain further embodiments the pregnant or pseudopregnant mammal is a human. In certain further embodiments the embryo is produced by in vitro fertilization.

In certain embodiments there is provided a method of selectively labeling a mammalian peripheral blood white cell neutrophil subpopulation, comprising contacting a population of mammalian peripheral blood white cells which comprises neutrophils with an immunomodulatory polypeptide that comprises an immunomodulatory polypeptide comprising the amino acid sequence set forth in SEQ ID NO:2 or in SEQ ID NO:106, wherein the immunomodulatory polypeptide comprises a detectable label. In certain further embodiments the detectable label is selected from the group consisting of a fluorescent dye, a radioactive substance and a metal particle.

In certain further embodiments of the above-described methods, the immunomodulatory peptide is selected from IgX, a fragment of IgX, and a variant of IgX. In certain embodiments the immunomodulatory polypeptide comprises no more than 31, 30, 29, 28, 27, 26, 25, 24, 23, 22, 21, 20, 19, 18, 17, 16, 15, 14, 13 or 12 amino acids. In certain embodiments the immunomodulatory polypeptide comprises a scFv of an immunoglobulin that is selected from (i) IgX and (ii) an immunoglobulin that comprises an immunoglobulin polypeptide that is selected from the group consisting of a polypeptide comprising the amino acid sequence set forth in any one of SEQ ID NOS:3 and 5-104. In certain embodiments the immunomodulatory polypeptide comprises a Fab of an immunoglobulin that is selected from (i) IgX and (ii) an immunoglobulin that comprises an immunoglobulin polypeptide that is selected from the group consisting of a polypeptide comprising the amino acid sequence set forth in any one of SEQ ID NOS:3 and 5-104. In certain embodiments the immunomodulatory polypeptide comprises a (Fab')$_2$ of an immunoglobulin that is selected from (i) IgX and (ii) an immunoglobulin that comprises an immunoglobulin polypeptide that is selected from the group consisting of a polypeptide comprising the amino acid sequence set forth in any one of SEQ ID NOS:3 and 5-104.

In certain embodiments the immunomodulatory polypeptide comprises an intact immunoglobulin heavy chain variable region having an amino acid sequence of an immunoglobulin variable region that is present in an immunoglobulin polypeptide that is selected from the group consisting of a polypeptide comprising the amino acid sequence set forth in any one of SEQ ID NOS:3 and 5-104. In certain embodiments the immunomodulatory polypeptide comprises an intact immunoglobulin heavy chain having an amino acid sequence of an immunoglobulin heavy chain that is selected from the sequences set forth in SEQ ID NOs:3 and 5-104. In certain embodiments the immunomodulatory polypeptide comprises an intact antibody, wherein the antibody comprises an intact immunoglobulin heavy chain having an amino acid sequence of an immunoglobulin heavy chain that is selected from the sequences set forth in SEQ ID NOs: 3 and 5-104.

According to certain embodiments there is provided a method of treating a malignant condition, comprising administering to a subject having or suspected of having a malignancy at least one composition that is selected from (a) a composition that comprises a therapeutically effective amount of an immunomodulatory polypeptide that comprises either the amino acid sequence set forth in SEQ ID NO:2 or the amino acid sequence set forth in SEQ ID NO:106, and (b) a composition that comprises a therapeutically effective amount of an antibody, or antigen-binding fragment thereof, that specifically binds to an immunomodulatory polypeptide of no more than 31, 30, 29, 28, 27, 26, 25, 24, 23, 22, 21, 20, 19, 18, 17, 16, 15, 14, 13 or 12 amino acids, said immunomodulatory polypeptide comprising either the amino acid sequence set forth in SEQ ID NO:2 or the amino acid sequence set forth in SEQ ID NO:106, and thereby treating the malignant condition. Preferably, treating the malignant condition comprises at least one of killing a tumor cell and inhibiting metastasis. In certain embodiments the malignant condition is selected from breast cancer, ovarian cancer, adenoma, colorectal carcinoma, gastric carcinoma, lung carcinoma, prostate carcinoma, hepatocellular carcinoma, melanoma, leukemia and lymphoma.

Certain other embodiments provide a method of treating an autoimmune disease, comprising administering to a subject having or suspected of having an autoimmune disease a composition that comprises a therapeutically effective amount of an immunomodulatory polypeptide that comprises either the amino acid sequence set forth in SEQ ID NO:2 or the amino acid sequence set forth in SEQ ID NO:106, or by administering antibodies directed against the SEQ ID NO:2 or against the amino acid sequence set forth in SEQ ID NO:106 and thereby treating the autoimmune disease. In certain further embodiments the autoimmune disease is selected from rheumatoid arthritis, psoriatic arthritis, ulcerative colitis, Crohn's disease, seronegative spondyloarthopathies, systemic lupus erythematosus, Behcet's disease and vasculitis.

In certain embodiments, there is provided an immunomodulatory polypeptide that competes with PeptideX2 or a variant thereof for specific binding to a human neutrophil, wherein said PeptideX2 comprises the amino acid sequence set forth in SEQ ID NO:2 and wherein the variant thereof comprises the amino acid sequence set forth in SEQ ID NO:106.

These and other aspects and embodiments of the present invention will become apparent upon reference to the following detailed description and attached drawings. All references disclosed herein are hereby incorporated by reference in their entirety as if each was incorporated individually.

BRIEF DESCRIPTION OF THE SEQUENCES

Figure 1:
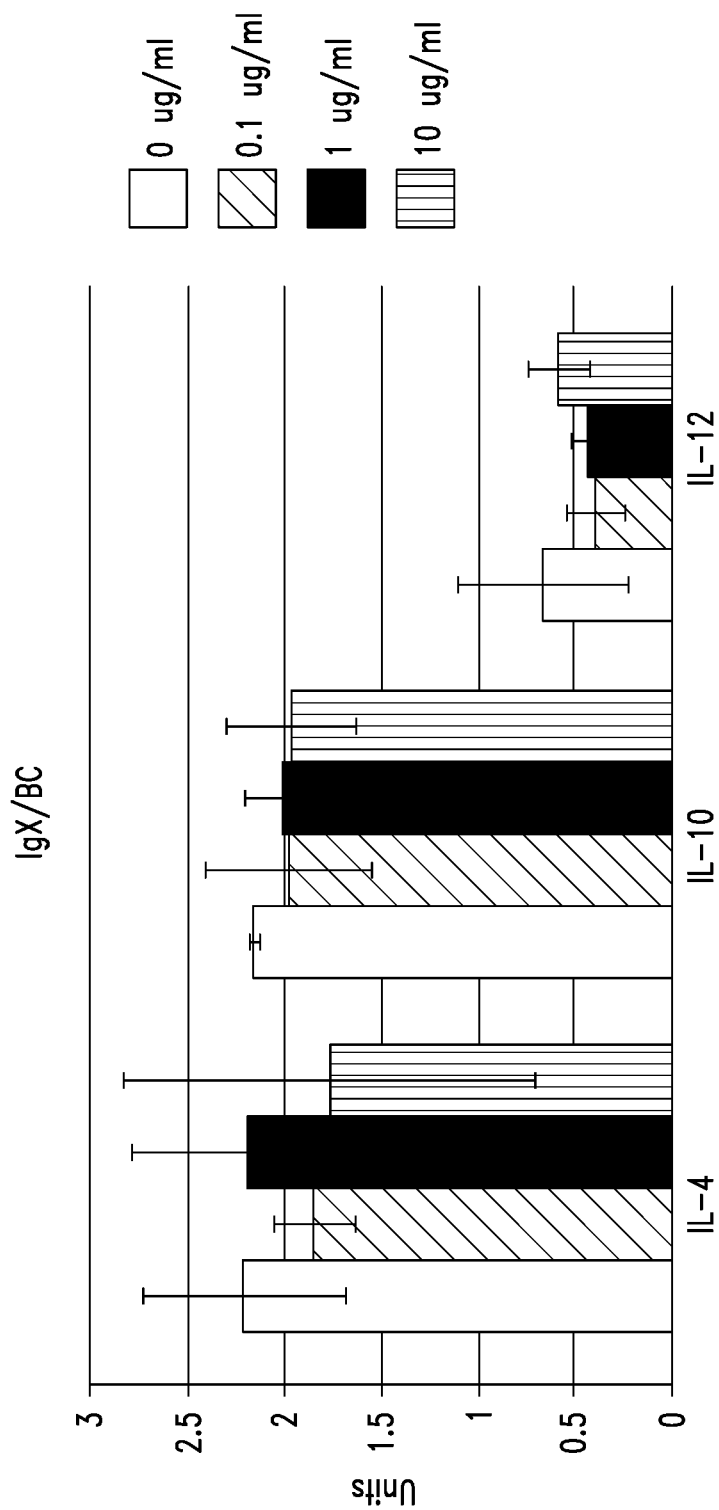
FIG. 1 is a bar graph that shows IL-4, IL-10 and IL-12 produced by whole peripheral blood cells from Donor #66 in response to culture with 0, 0.1, 1 or 10 ug/ml IgX derived from placental sample BC.

SEQ ID NO:1 is the amino acid sequence AEDTAVYYCAR of PeptideX1.

SEQ ID NO:2 is the amino acid sequence KSIAYLQMNSLK of PeptideX2.

SEQ ID NO:3 is the amino acid sequence of AAH90938.1.

SEQ ID NO:4 is the amino acid sequence KSIAYLQMNSLKTEDTALYYCTR, corresponding to amino acid residues at positions 97-119 of AAH90938.1.

SEQ ID NOs:5-104 correspond to the amino acid sequences of Ig heavy chains and Ig heavy chain variable regions identified in the BLAST search as set forth in Table 2 below.

SEQ ID NO:105 is the amino acid sequence KSIAYLQMNSLKTEDTALYYC, corresponding to amino acid residues at positions 97-117 of AAH90938.1.

SEQ ID NO:106 is the amino acid sequence of general formula K-X1-X2-X3-YLQM-X4-X5-LK wherein X1 is selected from S and N, X2 is selected from I, T, S, M, R and N, X3 is selected from A, L, V and Q, X4 is selected from N, D, S, T and A, and X5 is selected from S, T and N.

SEQ ID NO: 107 is the illustrative spacer amino acid sequence Glu-Gly-Lys-Ser-Ser-Gly-Ser-Gly-Ser-Glu-Ser-Lys-Val-Asp.

SEQ ID NO: 108 is the illustrative spacer amino acid sequence Lys-Glu-Ser-Gly-Ser-Val-Ser-Ser-Glu-Gln-Leu-Ala-Gln-Phe-Arg-Ser-Leu-Asp.

SEQ ID NO: 109 is the flexible polylinker amino acid sequence Gly-Gly-Gly-Gly-Ser.

SEQ ID NO: 110 is the AAH90938.1 amino acid sequence EVQLVE.

SEQ ID NO: 111 is the amino acid sequence DVQLLE, corresponding to the N-terminal sequence for sample BC H chain.

SEQ ID NOS: 112-115 are IgX H chain partial sequences from four different placental samples listed in Table 1.

DETAILED DESCRIPTION

The present disclosure relates to immunomodulatory polypeptides and peptides, and in particular to an unusual placentally derived human immunoglobulin described herein and designated IgX, and its derivative polypeptide PeptideX2 as described herein, including variants thereof, which peptides exhibit the immunomodulatory properties of IgX. Embodiments of the present invention are based in pertinent part on the discovery of a restricted immunoglobulin (Ig) heavy chain polypeptide, referred to herein as "IgX," and its surprising immunomodulatory effects. Unexpectedly, an immunoglobulin comprising the IgX polypeptide was isolated from human placentas and found to elicit the expression of cytokines, including in particular interleukin-6 (IL-6) and tumor necrosis factor-alpha (TNFα) and also interleukin-10 (IL-10), by peripheral blood leukocytes (PBL). This property, qualitatively shared by IgX and PeptideX2 as described herein, is quite remarkable in that this cytokine expression pattern by PBL is not characteristic of either a classic helper T cell type 1 (Th1) or a helper T cell type 2 (Th2) response. Even more remarkably, an isolated dodecapeptide derived from the heavy chain hypervariable region of IgX, referred to herein as "PeptideX2," exhibits the immunomodulatory properties of IgX. Furthermore, and as described in greater detail herein, PeptideX2 preferentially binds to and thus identifies a neutrophil subpopulation.

Without wishing to be bound by theory, it is hypothesized that the herein described placentally derived protein, IgX, contributes mechanistically to allograft success of the fetus in pregnancy and that the structural features of IgX which underlie this functional attribute reside at least in part in PeptideX2, which forms a portion of the IgX heavy-chain variable (Vh) region and, as disclosed herein, has also been identified in the Vh regions of 100 human IgG1(K) immunoglobulins. Further according to non-limiting theory, the immunomodulatory mechanisms that are recruited by IgX, including via PeptideX2 (which forms a portion of the IgX Vh structure), in the course of protecting the fetal-maternal allograft from immunological rejection without severely compromising overall immune potential and without triggering a massive inflammatory reaction, may also be usefully exploited in a number of medically relevant contexts, including improving outcomes in organ transplantation by decreasing (e.g., in a statistically significant manner relative to appropriate control conditions) immunological rejection mechanisms that may otherwise be manifest in host responses to organ or tissue grafts, including allografts and xenografts.

The distinctive immunomodulatory properties of IgX and PeptideX2 may also find beneficial uses in treating cancer, including promotion of mechanisms of tumor cell killing and/or in inhibition of metastasis, and also in treating GVHD in bone marrow transplant recipients, and in the context of reproductive medicine, for example, to improve fertility (including pregnancy initiated following in vitro fertilization (IVF)) by promoting embryonic implantation, and in reducing the severity of symptoms associated with preeclampsia and eclampsia during pregnancy. IgX or PeptideX2, including other polypeptides that contain one or more copies of the dodecameric Peptide X2 amino acid sequence as set forth in SEQ ID NO:2 such as the human IgG1(K) immunoglobulins presented in Table 2, may additionally be advantageously administered in treating autoimmune diseases such as rheumatoid arthritis, psoriatic arthritis, Crohn's disease, systemic lupus erythematosus and other autoimmune diseases, and may more generally induce a heretofore unprecedented non-Th1, non-Th2 immunological response that is characterized by up-regulated (e.g., increased in a statistically significant manner relative to an appropriate control) release of at least one of (and in certain preferred embodiments at least two of) IL-6, IL-10 and TNFα, by peripheral white blood cells.

According to a certain embodiment disclosed herein, there is provided PeptideX2, an immunomodulatory polypeptide that specifically binds to a cell surface structure that is present on certain human neutrophils. The immunomodulatory polypeptides described herein, for instance, IgX and PeptideX2 and other PeptideX2-containing immunoglobulins such as those described herein, may thus find immunotherapeutic uses, for example as agents for regulated immunosuppressive treatment. In certain contemplated embodiments, these and related PeptideX2-containing immunomodulatory polypeptides may usefully suppress immune effector cell proliferation in response to an allograft or xenograft, without severely compromising host immune potential and without inducing massive inflammation. The herein disclosed immunomodulatory polypeptides may, for example by way of illustration and not limitation, be used in transplant patients to prevent or ameliorate graft rejection and/or GVHD.

In certain other embodiments the invention relates to the use of the herein disclosed immunomodulatory polypeptides (e.g., PeptideX2, IgX, or other PeptideX2-containing polypeptides) in fertility treatments, and particularly for use in increasing the likelihood of embryonic implantation in a variety of contexts, including natural pregnancies as well as those that may result from introduction into a surrogate mother (such as a pseudopregnant female) of an embryo produced by IVF. In other embodiments, the herein disclosed immunomodulatory polypeptides (PeptideX2, IgX, or other PeptideX2-containing polypeptides) may be used in the prevention and/or treatment of pregnancy related conditions including preeclampsia and eclampsia. In such applications of the herein described compositions and methods, the present immunomodulatory polypeptide may be contacted with the embryo in vitro or in vivo and/or with the pregnant or pseudopregnant female in whom it is desired to promote fertility.

Other herein contemplated embodiments encompass the use of the disclosed immunomodulatory polypeptides (e.g., PeptideX2, IgX, or other PeptideX2-containing polypeptides) or the use of engineered antibodies specifically targeted to bind to peptideX2, IgX, or other peptideX2-containing polypeptides in order to control immunity and inflammation, for example, as controlled immunosuppressants in the treatment of autoimmune diseases and disorders as provided herein, such as rheumatoid arthritis, psoriatic arthritis, Crohn's disease, and others.

As described herein, placentally derived IgX having unusual immunological properties contains in its heavy chain sequence a region in the vicinity of the Vh CDR3 the amino acid sequence referred to as PeptideX2:

[SEQ ID NO: 2]
KSIAYLQMNSLK

Immunomodulatory properties of IgX are presented below include the ability to induce release of IL-6, IL-10 and TNFα by peripheral blood white cells, a property shared qualitatively by PeptideX2. Accordingly, certain useful embodiments as disclosed herein contemplate exploiting these and related properties of PeptideX2 and/or PeptideX2-containing polypeptides of no more than 31, 30, 29, 28, 27, 26, 25, 24, 23, 22, 21, 20, 19, 18, 17, 16, 15, 14, 13 or 12 amino acids, for example a polypeptide of sequence:

[SEQ ID NO: 105]
KSIAYLQMNSLKTEDTALYYC

In certain other useful embodiments the IgX immunomodulatory properties reside in structurally related polypeptides, including polypeptides of no more than 31, 30, 29, 28, 27, 26, 25, 24, 23, 22, 21, 20, 19, 18, 17, 16, 15, 14, 13 or 12 amino acids, that contain the amino acid sequence of general formula:

K-X1-X2-X3-YLQM-X4-X5-LK as set forth in SEQ
ID NO:106, wherein X1 is selected from S and N, X2 is selected from I, T, S, M, R and N, X3 is selected from A, L, V and Q, X4 is selected from N, D, S, T and A, and X5 is selected from S, T and N. In certain such embodiments wherein the polypeptide comprises a sequence having the general formula of SEQ ID NO:106 but in which the included sequence according to SEQ ID NO:106 is not the same as the sequence set forth in SEQ ID NO:2, polypeptides of more than 31 amino acids are also contemplated, such as polypeptides of 32, 33, 34, 35, 36, 37, 38, 39, 40, 41, 42, 43, 44, 45, 46, 47, 48, 49, 50, 51, 52, 53, 54, 55, 56, 57, 58, 59, 60, 61-70, 71-80, 81-90, 91-100 or more amino acids.

Certain other embodiments contemplate exploiting these and related properties of larger PeptideX2-containing polypeptides, in particular, immunoglobulin heavy chain variable region polypeptides that contain the PeptideX2 sequence (SEQ ID NO:2) or the sequence set forth in SEQ ID NO:106 as part of their primary structures, for instance, any of the human IgG1 heavy chain polypeptides (or Vh regions thereof or fragments or variants thereof so long as SEQ ID NO:2 or SEQ ID NO:106 is present) such as the human IgG1(K) heavy chains identified in Table 2.

It will therefore be appreciated that in certain herein disclosed embodiments an isolated immunomodulatory polypeptide comprising the PeptideX2 sequence set forth in SEQ ID NO:2 or SEQ ID NO:106 as provided herein may comprise 31, 30, 29, 28, 27, 26, 25, 24, 23, 22, 21, 20, 19, 18, 17, 16, 15, 14, 13 or 12 amino acids, with SEQ ID NO:2 or SEQ ID NO:106 being situated at the N-terminus with 0-19 amino acids of any sequence forming the C-terminus (e.g., as is the case in SEQ ID NOS:4 and 105), or SEQ ID NO:2 or SEQ ID NO:106 may be situated at the C-terminus with 0-19 amino acids of any sequence forming the N-terminus, or SEQ ID NO:2 or SEQ ID NO:106 may be situated at neither the N-terminus nor the C-terminus and may be linked via peptide bonds to additional amino acids of any sequence that form N- and C-termini, so long as the entire polypeptide is of no more than 31, 30, 29, 28, 27, 26, 25, 24, 23, 22, 21, 20, 19, 18, 17, 16, 15 or 14 amino acids in length. As also noted above, longer polypeptides are also contemplated in which is contained the sequence according to SEQ ID NO:106 so long as the so-contained sequence differs from SEQ ID NO:2 in at least one of the amino acid positions X1, X2, X3, X4 or X5 of SEQ ID NO:106.

According to certain other embodiments the PeptideX2-containing polypeptide need not be so limited and may comprise larger polypeptide sequences such as the SEQ ID NO:2-containing IgG1 Vh domain polypeptide sequences presented in Tables 1 and 2.

The presently disclosed embodiments for the first time provide specific immunoglobulin antigen-combining (V) region fragments having immunomodulatory properties as described herein, which have not previously been recognized. Depressed levels of overall endometrial/decidual IgG levels have previously been correlated with advancing trimesters during the course of pregnancy (Kutteh et al., 2001 *Am J Obstet. Gynecol.* 184:865) but no identification of individual IgG species or their specificities or biological effects have been described. Prior reports of an immunoglobulin component that was present in immunosuppressive endometrial extracts traced the immunosuppressive activity to the immunoglobulin constant (Fc) domain (Haruyama et al., 1991 *J. Reprod. Immunol.* 19:1; Kitano et al, 1990 *Acta Obst. Gynaec. Jpn.* 42(7):739), which does not mediate specific antigen recognition and binding. By pointing to a non-antigen specific biological effect mediated by the immunoglobulin constant (C) region, these earlier reports teach away from the presently described IgX and PeptideX2 polypeptides, which comprise immunomodulatory polypeptide regions of a distinctive immunoglobulin variable (V) region sequence.

Polypeptides and Proteins

The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. Thus, a "polypeptide" or a "protein" can comprise one (termed "a monomer") or a plurality (termed "a multimer") of amino acid chains. The terms "peptide," "polypeptide" and "protein" specifically encompass the immunomodulatory polypeptides of the present disclosure, or sequences that have deletions from, additions to, and/or substitutions of one or more amino acid of an immunomodulatory polypeptide.

The terms "isolated protein" and "isolated polypeptide" referred to herein means that a subject protein or polypeptide (1) is free of at least some other proteins or polypeptides with which it would typically be found in nature, (2) is essentially free of other proteins or polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein or polypeptide with which the "isolated protein" or "isolated polypeptide" may be associated in nature, (6) is operably associated (by covalent or noncovalent interaction) with a polypeptide with which it is not associated in nature, or (7) does not occur in nature. Such an isolated protein or polypeptide can be encoded by genomic DNA, cDNA, mRNA or other RNA, of may be of synthetic origin according to any of a number of well known chemistries for artificial peptide and protein synthesis, or any combination thereof. In certain embodiments, the isolated protein or polypeptide is substantially free from proteins or polypeptides or other contaminants that are found in its natural environment that would interfere with its use (therapeutic, diagnostic, prophylactic, research or otherwise).

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide. As used herein, "contiguous amino acids" refers to covalently linked amino acids corresponding to an uninterrupted linear portion of a disclosed amino acid sequence. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long.

Polypeptides may comprise a signal (or leader) sequence at the N-terminal end of the protein, which co-translationally or post-translationally directs transfer of the protein. The polypeptide may also be fused in-frame or conjugated to a linker or other sequence for ease of synthesis, purification or identification of the polypeptide (e.g., poly-His), or to enhance binding of the polypeptide to a solid support. Fusion domain polypeptides may be joined to the polypeptide at the N-terminus and/or at the C-terminus, and may include as non-limiting examples, immunoglobulin-derived sequences such as Ig constant region sequences or portions thereof, affinity tags such as His tag (e.g., hexahistidine or other polyhistidine), FLAG™ or myc or other peptide affinity tags, detectable polypeptide moieties such as green fluorescent protein (GFP) or variants thereof (e.g., yellow fluorescent protein (YFP), blue fluorescent protein (BFP), other aequorins or derivatives thereof, etc.) or other detectable polypeptide fusion domains, enzymes or portions thereof such as glutathione-S-transferase (GST) or other known enzymatic detection and/or reporter fusion domains, and the like, as will be familiar to the skilled artisan.

Cysteine-containing peptides may be used as fusion peptides that can be joined to the N- and/or C-terminus of the herein described peptide X2 (e.g., SEQ ID NO:2) or peptide X2-like (e.g., SEQ ID NO:106) containing polypeptides to permit ready assembly of such polypeptides into disulfide-crosslinked dimers, trimers, tetramers or higher multimers according to established methodologies. For example, fusion polypeptides containing immunoglobulin gene super-family member-derived sequences that include cysteine residues capable of forming interchain disulfide bridges are well known, as also are other strategies for engineering S—S linked multimers (e.g., Reiter et al., 1994 *Prot. Eng.* 7:697; Zhu et al., 1997 *Prot. Sci.* 6:781; Mabry et al., 2010 *Mabs* 2:20; Gao et al., 1999 *Proc. Nat. Acad. Sci. USA* 96:6025; Lim et al., 2010 *Biotechnol. Bioeng.* 106:27) Alternative approaches are also contemplated for grafting peptide sequences that promote multimer assembly as fusion domains onto a desired polypeptide such as the herein described immunomodulatory peptides (e.g., Fan et al., 2008 *FASEB J.* 22:3795).

Polypeptide modifications may be effected biosynthetically and/or chemically according to a wide variety of well known methodologies, and may also include conjugation to carrier proteins (e.g., keyhole limpet hemocyanin (KLH), bovine serum albumin (BSA), ovalbumin (OVA) or other molecules), and covalent or non-covalent immobilization on solid supports. Chemical or biosynthetic conjugation to a carrier is contemplated, according to certain embodiments, for generation of conjugates that are multivalent with respect to the herein described peptide X2 (e.g., a polypeptide that contains SEQ ID NO:2) or peptide X2-like (e.g., a polypeptide that contains SEQ ID NO:106) moieties. For example and according to non-limiting theory, it is believed that target cells for immunomodulation (e.g., a neutrophil subset) that express certain cell surface receptors for peptide X2 may transduce biological signals more efficiently when stimulated by a multivalent peptide X2 structure, relative to the level of induction that may be afforded by a monovalent peptide X2 structure. Also contemplated is detectable labeling with detectable indicator moieties (sometimes referred to as reporter moieties) such as fluorophores (e.g., FITC, TRITC, Texas Red, etc.). Examples of a broad range of detectable indicators (including colorimetric indicators) that may be selected for specific purposes are described in Haugland, 2002 *Handbook of Fluorescent Probes and Research Products*—Ninth Ed., Molecular Probes, Eugene, Oreg.; in Mohr, 1999 *J. Mater. Chem.*, 9: 2259-2264; in Suslick et al., 2004 *Tetrahedron* 60:11133-11138; and in U.S. Pat. No. 6,323,039. (See also, e.g., Fluka Laboratory Products Catalog, 2001 Fluka, Milwaukee, Wis.; and Sigma Life Sciences Research Catalog, 2000, Sigma, St. Louis, Mo.) A detectable indicator may be a fluorescent indicator, a luminescent indicator, a phosphorescent indicator, a radiometric indicator, a dye, an enzyme, a substrate of an enzyme, an energy transfer molecule, or an affinity label.

Other detectable indicators for use in certain embodiments contemplated herein include affinity reagents such as antibodies, lectins, immunoglobulin Fc receptor proteins (e.g., *Staphylococcus aureus* protein A, protein G or other Fc receptors), avidin, biotin, other ligands, receptors or counterreceptors or their analogues or mimetics, and the like. For such affinity methodologies, reagents for immunometric measurements, such as suitably labeled antibodies or lectins, may be prepared including, for example, those labeled with radionuclides, with fluorophores, with affinity tags, with biotin or biotin mimetic sequences or those prepared as antibody-enzyme conjugates (see, e.g., Weir, D. M., *Handbook of Experimental Immunology,* 1986, Blackwell Scientific, Boston; Scouten, W. H., 1987 *Methods in Enzymology* 135:30-65; Harlow and Lane, *Antibodies: A Laboratory Manual,* 1988 Cold Spring Harbor Laboratory, Cold Spring Harbor, N.Y.; Haugland, *Handbook of Fluorescent Probes and Research Products*—Ninth Ed., 2002 Molecular Probes, Eugene, Oreg.; Scopes, R. K., *Protein Purification: Principles and Practice,* 1987, Springer-Verlag, NY; Hermanson, G. T. et al., *Immobilized Affinity Ligand Techniques,* 1992, Academic Press, Inc., NY; Luo et al., 1998 *J. Biotechnol.* 65:225 and references cited therein).

A peptide linker/spacer sequence may also be employed to separate multiple polypeptide components by a distance sufficient to ensure that each polypeptide folds into its secondary and/or tertiary structures, if desired. Such a peptide linker sequence can be incorporated into a fusion polypeptide using standard techniques well known in the art.

Certain peptide spacer sequences may be chosen, for example, based on: (1) their ability to adopt a flexible extended conformation; (2) their inability to adopt a secondary structure that could interact with functional epitopes on the first and second polypeptides; and/or (3) the lack of hydrophobic or charged residues that might react with the polypeptide functional epitopes.

In one illustrative embodiment, peptide spacer sequences contain, for example, Gly, Asn and Ser residues. Other near neutral amino acids, such as Thr and Ala, may also be included in the spacer sequence.

Other amino acid sequences which may be usefully employed as spacers include those disclosed in Maratea et al., *Gene* 40:39 46 (1985); Murphy et al., *Proc. Natl. Acad. Sci. USA* 83:8258 8262 (1986); U.S. Pat. Nos. 4,935,233 and 4,751,180.

Other illustrative spacers may include, for example, Glu-Gly-Lys-Ser-Ser-Gly-Ser-Gly-Ser-Glu-Ser-Lys-Val-Asp (SEQ ID NO: 107) (Chaudhary et al., 1990, Proc. Natl. Acad. Sci. U.S.A. 87:1066-1070) and Lys-Glu-Ser-Gly-Ser-Val-Ser-Ser-Glu-Gln-Leu-Ala-Gln-Phe-Arg-Ser-Leu-Asp (SEQ ID NO: 108) (Bird et al., 1988, Science 242:423-426).

In some embodiments, spacer sequences are not required when the first and second polypeptides have non-essential N-terminal amino acid regions that can be used to separate the functional domains and prevent steric interference. Two coding sequences can be fused directly without any spacer or by using a flexible polylinker composed, for example, of the pentamer Gly-Gly-Gly-Gly-Ser (SEQ ID NO: 109) repeated 1 to 3 times.

In certain illustrative embodiments, a peptide spacer is between 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids.

In other illustrative embodiments, a peptide spacer comprises about 1, 5, 10, 15, 20, 25, 30, 35, 40, 45, 50 or more amino acids in length.

Amino acid sequence modification(s) of the immunomodulatory polypeptides (e.g., PeptideX2 [SEQ ID NO:2] sequence-containing polypeptides) described herein are contemplated, including polypeptides that contain in their sequence the amino acid sequence set forth in SEQ ID NO:106. For example, it may be desirable to improve the binding affinity and/or other biological properties of the immunomodulatory polypeptide. For example, amino acid sequence variants may be prepared by introducing appropriate nucleotide changes into a polynucleotide that encodes the immunomodulatory polypeptide or by peptide synthesis. Such modifications include, for example, deletions from, and/or insertions into and/or substitutions of, residues within the amino acid sequence of the immunomodulatory polypeptide. Any combination of deletion, insertion, and substitution may be made to arrive at the final immunomodulatory polypeptide variant, provided that the final construct possesses the desired characteristics (e.g., suppresses cell proliferation in a mixed lymphocyte reaction, or induces elaboration by peripheral blood white cells of the non-Th1/non-Th2 cytokine profile as described herein, or exhibits activity in a preimplantation factor activity assay such as those described in U.S. Pat. Nos. 5,646,003, 5,981,198, or WO 2005/040196). The amino acid changes also may alter post-translational processes of the immunomodulatory polypeptide, such as changing the number or position of glycosylation sites.

Determination of the three-dimensional structures of representative polypeptides (e.g., PeptideX2 or a SEQ ID NO:2-containing polypeptide) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., *Nature* 450:259 (2007); Raman et al. *Science* 327:1014-1018 (2010). Some additional non-limiting examples of computer algorithms that may be used for these and related embodiments, such as for rational design of immunomodulatory polypeptides as provided herein, include VMD which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/.

Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrödinger (Munich, Germany).

Antibodies

Certain embodiments of the present invention include antibodies that specifically bind to a PeptideX2 [SEQ ID NO:2]—containing polypeptide as provided herein, while certain other embodiments include antibodies that themselves include the PeptideX2 sequence set forth in SEQ ID NO:2. As described herein, PeptideX2 (SEQ ID NO:2) was identified as a region of placentally derived antibody IgX, and PeptideX2 shares with IgX certain advantageous and unexpected immunomodulatory properties.

The term "antibody" (Ab) as used herein includes monoclonal antibodies, polyclonal antibodies, multispecific antibodies (e.g., bispecific antibodies), and antibody fragments, so long as they exhibit the desired biological activity, e.g., specifically bind to neutrophils. The term "immunoglobulin" (Ig) is used interchangeably with "antibody" herein.

The basic antibody unit is a heterotetrameric glycoprotein composed of two identical light (L) chains and two identical heavy (H) chains. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. It will be appreciated that mammals encoding multiple Ig isotypes will be able to undergo isotype class switching.

An IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain. In the case of IgG, the 4-chain unit is generally about 150,000 daltons. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The V domain mediates antigen binding and defines specificity of a particular antibody for its particular antigen. The gene sequence encoding the $V_H$ domain has multiple copies of variable (V), diversity (D), and joining (J) segments. The gene sequence encoding the $V_L$ domain contains multiple copies of V and J segments. The $V_H$ and $V_L$ regions undergo gene rearrangement (i.e., somatic recombination) to develop diverse antigen specificity in antibodies. The term "variable" refers to the fact that certain segments of the V domains differ extensively in sequence among antibodies.

However, the variability is not evenly distributed across the 110-amino acid span of the variable domains. Instead, the V regions consist of relatively invariant stretches called framework regions (FRs) of 15-30 amino acids separated by short regions of extreme variability called "hypervariable regions." These hypervariable regions are the result of somatic hypermutation during the affinity maturation process, and they are typically each 9-18 amino acids long. However, they have been found to range from 4-28 amino acids in length depending upon the particular epitope. For example, CDR3 regions up to at least 22 or 23 amino acids in length have been described. See, e.g., Morea V, et al., J Mol Biol. 275(2):269-94 (1998) and Kabat, E. A., et al., Sequences of Proteins of Immunological Interest, Fifth Edition. NIH Publication No. 91-3242 (1991).

The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 28-36(H1), 50-65 (H2) and 95-102 (H3) in the $V_H$; Kabat et al., Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the $V_L$, and 26-32 (H1), 53-55 (H2) and 96-101 (H3) in the $V_H$; Chothia and Lesk, J. Mol. Biol. 196:901-917 (1987)).

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Bradford method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, silver stain. Isolated antibody includes the antibody in situ within recombinant cells since at least one component of the antibody's natural environment will not be present. Ordinarily, however, isolated antibody will be prepared by at least one purification step.

An "intact" antibody is one that comprises an antigen-binding site as well as a $C_L$ and at least heavy chain constant domains, $C_H 1$, $C_H 2$ and $C_H 3$. The constant domains may be native sequence constant domains (e.g., human native sequence constant domains) or amino acid sequence variants thereof. Preferably, the intact antibody has one or more effector functions.

An "antibody fragment" is a polypeptide comprising or consisting of a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H 1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Both the Fab and F(ab')$_2$ are examples of "antigen-binding fragments." Fab' fragments differ from Fab fragments by having additional few residues at the carboxy terminus of the $C_H 1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions (i.e., the CH2 and CH3 domains) of both H chains held together by disulfides. The effector functions of antibodies are determined by sequences in the Fc region. The Fc domain is the portion of the antibody recognized by cell receptors, such as the FcR, and to which the complement-activating protein, C1q, binds.

"Fv" is the minimum antibody fragment that contains a complete antigen-recognition and antigen-binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

As used herein, the term "polyclonal antibody" refers to an antibody obtained from a population of antigen-specific antibodies that recognize more than one epitope of the specific antigen. "Antigen" or "immunogen" refers to a peptide, lipid, polysaccharide or polynucleotide which is recognized by the adaptive immune system. Antigens may be self or non-self molecules. Examples of antigens include, but are not limited to, bacterial cell wall components, pollen, and rh factor. The region of an antigen that is specifically recognized by a specific antibody is an "epitope" or "antigenic determinant." A single antigen may have multiple epitopes.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different epitopes, each monoclonal antibody is directed against a single epitope of the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in certain embodiments of the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric antibodies" in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, U.S. Pat. Nos. 4,816,567; 5,530,101 and 7,498,415; and Morrison et al., Proc. Natl. Acad. Sci. USA, 81:6851-6855 (1984)). For example, chimeric antibodies may comprise human and non-human residues. Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992). Chimeric antibodies also include primatized and humanized antibodies.

A "humanized antibody" is generally considered to be a human antibody that has one or more amino acid residues introduced into it from a source that is non-human. These non-human amino acid residues are typically taken from a variable domain. Humanization is traditionally performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting non-human variable sequences for the corresponding sequences of a human antibody. Accordingly, such "humanized" antibodies are chimeric antibodies (U.S. Pat. Nos. 4,816,567; 5,530,101 and 7,498,415) wherein substantially less than an intact human variable domain has been substituted by the corresponding sequence from a non-human species. In some instances, a "humanized" antibody is one which is produced by a non-human cell or animal and comprises human sequences, e.g., $H_C$ domains.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance. In some instances, human antibodies are produced by transgenic animals. For example, see U.S. Pat. Nos. 5,770,429; 6,596,541 and 7,049,426.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

The phrase "functional fragment or analog" of an antibody is a compound having qualitative biological activity in common with a full-length antibody. For example, a functional fragment or analog of an anti-PeptideX2 antibody is one that can bind to PeptideX2.

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, a PeptideX2-specific antibody specifically binds to PeptideX2 if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (Ann. N. Y. Acad. Sci. USA 51:660 (1949)).

Binding properties of an antibody to antigens, cells or tissues thereof may generally be determined and assessed using immunodetection methods including, for example, immunofluorescence-based assays, such as immunohistochemistry (IHC) and/or fluorescence-activated cell sorting (FACS).

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

Nucleic Acids and Polynucleotides

Immunomodulatory polypeptides as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

The present invention thus further provides in certain embodiments an isolated nucleic acid encoding PeptideX2 (comprising the amino acid sequence set forth in SEQ ID NO:2) or a polypeptide of 12, 13, 14, 15, 16, 17, 18, 19, 20, 21, 22, 23, 24, 25, 26, 27, 28, 29, 30 or 31 amino acids that includes the dodecameric sequence of PeptideX2, including the IgX heavy chain and also including, for example, any of the polypeptides having the amino acid sequences set forth in SEQ ID NO:3 and SEQ ID NOS:5-104. As described below (see Examples), the PeptideX2 sequence may occur within or partially within a defined immunoglobulin complementarity determining region (CDR) in such sequences, such that in certain embodiments an isolated nucleic acid that comprises a polynucleotide sequence encoding SEQ ID NO:2 may comprise all or a portion of an immunoglobulin chain-encoding polynucleotide (e.g., an immunoglobulin heavy chain such as a human gamma chain).

Certain other embodiments additionally contemplate an antibody or antigen-binding fragment thereof that specifically binds to PeptideX2 as described herein, for instance, an antibody that may itself be an immunomodulatory polypeptide that competes with PeptideX2 for specific binding to a human neutrophil. Certain related embodiments may therefore contemplate a nucleic acid which codes for an anti-PeptideX2 immunoglobulin complementarity determining region (CDR) or heavy-chain variable (VH) or light-chain variable (VL) domain as described herein. Nucleic acids include DNA and RNA. These and related embodiments may include polynucleotides encoding immunomodulatory polypeptides as described herein. The term "isolated polynucleotide" as used herein shall mean a polynucleotide of genomic, cDNA, or synthetic origin or some combination thereof, wherein by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

Immunomodulatory polypeptides as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Such modifications may include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phosphoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, *Nucl. Acids Res.,* 14:9081; Stec et al., 1984, *J. Am. Chem. Soc.,* 106:6077; Stein et al., 1988, *Nucl. Acids Res.,* 16:3209; Zon et al., 1991, *Anti-Cancer Drug Design,* 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, *Chemical Reviews,* 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, the present disclosure also provides polynucleotides encoding the immunomodulatory polypeptides (e.g., PeptideX2, IgX, and other PeptideX2 sequence-containing polypeptides) described herein. In certain embodiments, polynucleotides are provided that comprise some or all of a polynucleotide sequence encoding a peptide as described herein and complements of such polynucleotides.

In other related embodiments, polynucleotide variants may have substantial identity to a polynucleotide sequence encoding an immunomodulatory polypeptide described herein. For example, a polynucleotide may be a polynucleotide comprising at least 70% sequence identity, preferably at least 75%, 80%, 85%, 90%, 95%, 96%, 97%, 98%, or 99% A or higher, sequence identity compared to a reference polynucleotide sequence such as a sequence encoding an antibody described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the antibody encoded by the variant polynucleotide is not substantially diminished relative to an antibody encoded by a polynucleotide sequence specifically set forth herein.

In certain other related embodiments, polynucleotide fragments may comprise or consist essentially of various lengths of contiguous stretches of sequence identical to or complementary to a sequence encoding an immunomodulatory polypeptide as described herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of a sequences the encodes an immunomodulatory polypeptide, or variant thereof, disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of a polynucleotide encoding an immunomodulatory polypeptide described herein or at both ends of a polynucleotide encoding an immunomodulatory polypeptide described herein.

In another embodiment, polynucleotides are provided that are capable of hybridizing under moderate to high stringency conditions to a polynucleotide sequence encoding an immunomodulatory polypeptide, or variant thereof, provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the polynucleotides described above, e.g., polynucleotide variants, fragments and hybridizing sequences, encode immunomodulatory polypeptides that bind neutrophils. In other embodiments, such polynucleotides encode immunomodulatory polypeptides, or variants thereof, that bind to neutrophils at least about 50%, at least about 70%, and in certain embodiments, at least about 90% as well as an immunomodulatory polypeptide sequence specifically set forth herein (e.g., PeptideX2). In further embodiments, such polynucleotides encode immunomodulatory polypeptides, or variants thereof, that bind to neutrophils with greater affinity than the immunomodulatory polypeptides set forth herein, for example, that bind quantitatively at least about 105%, 106%, 107%, 108%, 109%, or 110% as well as an immunomodulatory peptide sequence specifically set forth herein.

As described elsewhere herein, determination of the three-dimensional structures of representative polypeptides (e.g., PeptideX2, IgX or another PeptideX2 sequence-containing polypeptide of 13, 14, 15, 16, 17, 18, 19, 20, 21, 22, 23, 24, 25, 26, 27, 28, 29, 30, 31 or more amino acids) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. A variety of computer programs are known to the skilled artisan for determining appropriate amino acid substitutions (or appropriate polynucleotides encoding the amino acid sequence) within an antibody such that, for example, affinity is maintained or better affinity is achieved.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an immunomodulatory peptide as described herein, or an antibody that specifically binds to such a peptide, as described herein. Some of these polynucleotides bear minimal sequence identity to the nucleotide sequence of the native or original polynucleotide sequence that encode immunomodulatory polypeptides described herein. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the immunomodulatory polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the polynucleotide sequences that encode an immunomodulatory polypeptide disclosed herein, or a variant thereof, to alter one or more properties of the encoded polypeptide, such as the binding affinity of the peptide or the variant thereof, or the immunosuppressive or immunostimulatory effects. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

According to certain related embodiments there is provided a recombinant host cell which comprises one or more constructs as described herein; a nucleic acid encoding immunomodulatory polypeptide or variant thereof; and a method of producing of the encoded product, which method comprises expression from encoding nucleic acid therefor. Expression may conveniently be achieved by culturing under appropriate conditions recombinant host cells containing the nucleic acid. Following production by expression, an immunomodulatory polypeptide may be isolated and/or purified using any suitable technique, and then used as desired.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli.

The expression of peptides in prokaryotic cells such as E. coli is well established in the art. For a review, see for example Pluckthun, A. Bio/Technology 9: 545-551 (1991). Expression in eukaryotic cells in culture is also available to those skilled in the art as an option for production of immunomodulatory polypeptides, see recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described immunomodulatory polypeptides, and which further expresses or is capable of expressing a selected gene of interest, such as a gene encoding any herein described immunomodulatory polypeptide. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide such as an immunomodulatory polypeptide as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

Certain embodiments contemplated herein include antisense-based nucleic acid technologies that may be implemented in a manner that specifically alters (e.g., increases or decreases in a statistically significant manner) expression of a PeptideX2-encoding polynucleotide, or of a polynucleotide that encodes a polypeptide as provided herein which comprises the PeptideX2 [SEQ ID NO:2] amino acid sequence, such as a polynucleotide that encodes any of the polypeptides having amino acid sequences set forth in SEQ ID NOS:2 and 4-105. Such antisense-based technologies include RNA interference, ribozymes and antisense nucleic acids.

RNA interference (RNAi) is a polynucleotide sequence-specific, post-transcriptional gene silencing mechanism effected by double-stranded RNA that results in degradation of a specific messenger RNA (mRNA), thereby reducing the expression of a desired target polypeptide encoded by the mRNA (see, e.g., WO 99/32619; WO 01/75164; U.S. Pat. No. 6,506,559; Fire et al., Nature 391:806-11 (1998); Sharp, Genes Dev. 13:139-41 (1999); Elbashir et al. Nature 411: 494-98 (2001); Harborth et al., J. Cell Sci. 114:4557-65 (2001)). RNAi is mediated by double-stranded polynucleotides as also described hereinbelow, for example, double-stranded RNA (dsRNA), having sequences that correspond to exonic sequences encoding portions of the polypeptides for which expression is compromised. RNAi reportedly is not effected by double-stranded RNA polynucleotides that share sequence identity with intronic or promoter sequences (Elbashir et al., 2001). RNAi pathways have been best characterized in *Drosophila* and *Caenorhabditis elegans*, but "small interfering RNA" (siRNA) polynucleotides that interfere with expression of specific polypeptides in higher eukaryotes such as mammals (including humans) have also been described (e.g., Tuschl, 2001 *Chembiochem.* 2:239-245; Sharp, 2001 *Genes Dev.* 15:485; Bernstein et al., 2001 *RNA* 7:1509; Zamore, 2002 *Science* 296:1265; Plasterk, 2002 *Science* 296:1263; Zamore 2001 *Nat. Struct. Biol.* 8:746; Matzke et al., 2001 *Science* 293:1080; Scadden et al., 2001 *EMBO Rep.* 2:1107) and subsequently elaborated upon.

According to a current non-limiting model, the RNAi pathway is initiated by ATP-dependent, processive cleavage of long dsRNA into double-stranded fragments of about 18-27 (e.g., 19, 20, 21, 22, 23, 24, 25, 26, etc.) nucleotide base pairs in length, called small interfering RNAs (siRNAs) (see review by Hutvagner et al., *Curr. Opin. Gen. Dev.* 12:225-32 (2002); Elbashir et al., 2001; Nykänen et al., *Cell* 107:309-21 (2001); Zamore et al., *Cell* 101:25-33 (2000); Bass, *Cell* 101:235-38 (2000)). In *Drosophila*, an enzyme known as "Dicer" cleaves the longer double-stranded RNA into siRNAs; Dicer belongs to the RNase III family of dsRNA-specific endonucleases (WO 01/68836; Bernstein et al., *Nature* 409:363-66 (2001)). Further according to this non-limiting model, the siRNA duplexes are incorporated into a protein complex, followed by ATP-dependent unwinding of the siRNA, which then generates an active RNA-induced silencing complex (RISC) (WO 01/68836). The complex recognizes and cleaves a target RNA that is complementary to the guide strand of the siRNA, thus interfering with expression of a specific protein (Hutvagner et al., supra).

In *C. elegans* and *Drosophila*, RNAi may be mediated by long double-stranded RNA polynucleotides (WO 99/32619; WO 01/75164; Fire et al., 1998; Clemens et al., *Proc. Natl. Acad. Sci. USA* 97:6499-6503 (2000); Kisielow et al., *Biochem. J.* 363:1-5 (2002); see also WO 01/92513 (RNAi-mediated silencing in yeast)). In mammalian cells, however, transfection with long dsRNA polynucleotides (i.e., greater than 30 base pairs) leads to activation of a non-specific sequence response that globally blocks the initiation of protein synthesis and causes mRNA degradation (Bass, *Nature* 411:428-29 (2001)). Transfection of human and other mammalian cells with double-stranded RNAs of about 18-27 nucleotide base pairs in length interferes in a sequence-specific manner with expression of particular polypeptides encoded by messenger RNAs (mRNA) containing corresponding nucleotide sequences (WO 01/75164; Elbashir et al., 2001; Elbashir et al., *Genes Dev.* 15:188-200 (2001)); Harborth et al., *J. Cell Sci.* 114:4557-65 (2001);

Carthew et al., *Curr. Opin. Cell Biol.* 13:244-48 (2001); Mailand et al., *Nature Cell Biol.* Advance Online Publication (Mar. 18, 2002); Mailand et al. 2002 *Nature Cell Biol.* 4:317).

siRNA polynucleotides may offer certain advantages over other polynucleotides known to the art for use in sequence-specific alteration or modulation of gene expression to yield altered levels of an encoded polypeptide product. These advantages include lower effective siRNA polynucleotide concentrations, enhanced siRNA polynucleotide stability, and shorter siRNA polynucleotide oligonucleotide lengths relative to such other polynucleotides (e.g., antisense, ribozyme or triplex polynucleotides).

By way of a brief background, "antisense" polynucleotides bind in a sequence-specific manner to target nucleic acids, such as mRNA or DNA, to prevent transcription of DNA or translation of the mRNA (see, e.g., U.S. Pat. Nos. 5,168,053; 5,190,931; 5,135,917; 5,087,617; see also, e.g., Clusel et al., 1993 *Nucl. Acids Res.* 21:3405-11, describing "dumbbell" antisense oligonucleotides). "Ribozyme" polynucleotides can be targeted to any RNA transcript and are capable of catalytically cleaving such transcripts, thus impairing translation of mRNA (see, e.g., U.S. Pat. Nos. 5,272,262; 5,144,019; and 5,168,053, 5,180,818, 5,116,742 and 5,093,246; U.S. 2002/193579). "Triplex" DNA molecules refers to single DNA strands that bind duplex DNA to form a colinear triplex molecule, thereby preventing transcription (see, e.g., U.S. Pat. No. 5,176,996, describing methods for making synthetic oligonucleotides that bind to target sites on duplex DNA). Such triple-stranded structures are unstable and form only transiently under physiological conditions.

Because single-stranded polynucleotides do not readily diffuse into cells and are therefore susceptible to nuclease digestion, development of single-stranded DNA for antisense or triplex technologies often requires chemically modified nucleotides to improve stability and absorption by cells. siRNAs, by contrast, are readily taken up by intact cells, are effective at interfering with the expression of specific polypeptides at concentrations that are several orders of magnitude lower than those required for either antisense or ribozyme polynucleotides, and do not require the use of chemically modified nucleotides.

It will be appreciated that the practice of the several embodiments of the present invention will employ, unless indicated specifically to the contrary, conventional methods in virology, immunology, microbiology, molecular biology and recombinant DNA techniques that are within the skill of the art, and many of which are described below for the purpose of illustration. Such techniques are explained fully in the literature. See, e.g., *Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); *Animal Cell Culture* (R. Freshney, ed., 1986); Perbal, *A Practical Guide to Molecular Cloning* (1984) and other like references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

As used in this specification and the appended claims, the singular forms "a," "an" and "the" include plural references unless the content clearly dictates otherwise. Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. Each embodiment in this specification is to be applied mutatis mutandis to every other embodiment unless expressly stated otherwise.

Compositions and Methods of Use

The present disclosure provides compositions comprising the herein described immunomodulatory polypeptides and variants thereof, which in preferred embodiments may comprise a PeptideX2-containing polypeptide as provided herein (e.g., a polypeptide comprising SEQ ID NO:2, SEQ ID NO:4, SEQ ID NO:105 or SEQ ID NO:106) and/or an antibody as provided herein that specifically binds to such a PeptideX2-containing polypeptide, and also provides administration of such compositions in a variety of therapeutic settings.

Administration of the immunomodulatory polypeptides, or antibodies specific therefor, described herein, in pure form or in an appropriate pharmaceutical composition, can be carried out via any of the accepted modes of administration of agents for serving similar utilities. The pharmaceutical compositions can be prepared by combining an immunomodulatory polypeptide or immunomodulatory polypeptide-containing composition or an antibody specific for PeptideX2 with an appropriate physiologically acceptable carrier, diluent or excipient, and may be formulated into preparations in solid, semi-solid, liquid or microparticle— (e.g., microdroplet) containing gaseous forms, such as tablets, capsules, powders, granules, ointments, solutions, suppositories, injections, inhalants, gels, microspheres, and aerosols. In addition, other pharmaceutically active ingredients (including other immunosuppressive agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical.

Preferred modes of administration depend upon the nature of the condition to be treated or prevented, which in certain embodiments will refer to a deleterious or clinically undesirable condition the extent, severity, likelihood of occurrence and/or duration of which may be decreased (e.g., reduced in a statistically significant manner relative to an appropriate control situation such as an untreated control)

according to certain methods provided herein. An amount that, following administration, detectably reduces, inhibits, prevents or delays such a condition, for instance, the rejection of a transplant such as an organ allograft or bone marrow transplant, or the partial or complete reduction of a tumor burden, is considered effective. Persons skilled in the relevant arts will be familiar with any number of diagnostic, surgical and other clinical criteria to which can be adapted administration of the immunomodulatory compositions described herein. See, e.g., Humar et al., Atlas of Organ Transplantation, 2006, Springer; Kuo et al., Comprehensive Atlas of Transplantation, 2004 Lippincott, Williams & Wilkins; Gruessner et al., Living Donor Organ Transplantation, 2007 McGraw-Hill Professional; Antin et al., Manual of Stem Cell and Bone Marrow Transplantation, 2009 Cambridge University Press; Wingard et al. (Ed.), Hematopoietic Stem Cell Transplantation: A Handbook for Clinicians, 2009 American Association of Blood Banks.

In another embodiment, the amount administered is sufficient to increase the rate of embryo implantation. In certain embodiments, the immunomodulatory polypeptide is administered to in vitro fertilization (IVF) patients (which may include a pseudopregnant patient such as a surrogate mother), and/or contacted with an IVF-generated embryo in vitro, to increase, promote or permit implantation of the embryo. In other embodiments, the immunomodulatory polypeptide is administered to an individual trying to get pregnant with or without prior diagnosed fertility difficulties. The effectiveness of an immunomodulatory polypeptide to modulate the immune response, and thereby modulate embryo implantation, can be determined using assays known in the art, such as, for example, the "PIF assays" described in U.S. Pat. Nos. 5,646,003 and 5,981,198 and PCT Application Publication Nos. WO 2003/004601 and WO 2005/040196, the disclosures of which are incorporated herein by reference in their entirety. Principles and practices in reproductive medicine are known to skilled clinicians, who will appreciate the factors involved in adaptation of the present disclosure to the clinical setting. See, e.g., Lebovic et al., Reproductive Endocrinology and Infertility: Handbook for Clinicians, 2005 Scrub Hill Press; Botros et al., Infertility and Assisted Reproduction, 2008 Cambridge Univ. Press; Greene et al., Creasy and Resnick's Maternal-Fetal Medicine: Principle and Practice, 2008 Saunders Publishing; Cunningham et al., Williams' Obstetrics-23$^{rd}$ Ed. 2009 McGraw-Hill Professional.

In other embodiments, the amount administered is sufficient to result in clinically relevant reduction in symptoms of preeclampsia, hemolysis-elevated liver enzymes-low platelet count (HELLP) syndrome and eclampsia, such as, but not limited to, reduction of any one or more of hypertension, edema of the hands and/or face, proteinuria, sudden weight gain, nausea, vomiting, abdominal pain, shoulder pain, lower back pain, muscle aches or pains, headache, changes in vision, blurry vision, hyperreflexia, racing pulse, mental confusion, anxiety, shortness of breath, hemolysis, elevated liver enzymes, low platelet count, decreased urine output, fatigue, fluid retention, nosebleeds, enlarged liver and seizures or convulsions.

In other embodiments, the amount of PeptideX2-containing polypeptide (e.g., a polypeptide comprising SEQ ID NO:2, SEQ ID NO:4, SEQ ID NO:105 or SEQ ID NO:106) or specific anti-PeptideX2 antibody that is administered is sufficient to result in clinically relevant reduction in symptoms of autoimmune diseases, including but not limited to rheumatoid arthritis (RA), systemic lupus erythematosus (SLE), inflammatory bowel disease (IBD), psoriatic arthritis, Crohn's disease, ulcerative colitis, seronegative spondyloarthropathies, Behcet's disease, vasculitis, and other autoimmune diseases. Reduction in RA symptoms may be evidenced, for example by way of illustration and not limitation, as reduction of any one or more of fatigue, loss of appetite, low fever, swollen glands, weakness, swollen joints, joint pain, morning stiffness, warm, tender, and stiff joints when not used for as little as an hour, bilateral joint pain (fingers (but not the fingertips), wrists, elbows, shoulders, hips, knees, ankles, toes, jaw, and neck may be affected); loss of range of motion of affected joints, pleurisy, eye burning, eye itching, eye discharge, nodules under the skin, numbness, tingling, or burning in the hands and feet. Criteria for diagnosis and clinical monitoring of RA patients are well known to those skilled in the relevant art. See, e.g., Hochberg et al., Rheumatology, 2010 Mosby; Firestein et al., Textbook of Rheumatology, 2008 Saunders. Criteria for diagnosis and clinical monitoring of patients having RA and/or other autoimmune diseases are also well known to those skilled in the relevant art. See, e.g., Petrov, Autoimmune Disorders: Symptoms, Diagnosis and Treatment, 2011 Nova Biomedical Books; Mackay et al. (Eds.), The Autoimmune Diseases-Fourth Edition, 2006 Academic Press; Brenner (Ed.), Autoimmune Diseases: Symptoms, Diagnosis and Treatment, 2011 Nova Science Pub. Inc.

Certain embodiments contemplate method of treating a malignant condition, comprising administering to a subject having or suspected of having a malignancy a composition that comprises a therapeutically effective amount of an immunomodulatory polypeptide that comprises either the amino acid sequence set forth in SEQ ID NO:2 or the amino acid sequence set forth in SEQ ID NO:106, or the use of antibodies that specifically bind to peptideX2, IgX, or other peptideX2-containing polypeptides (e.g., a polypeptide comprising SEQ ID NO:2, SEQ ID NO:4, SEQ ID NO:105 or SEQ ID NO:106) and thereby treating the malignant condition. According to certain such embodiments, the peptide that comprises SEQ ID NO:2, SEQ ID NO:4, SEQ ID NO:105 or SEQ ID NO:106, or the antibody that is capable of specifically binding to a peptide that comprises SEQ ID NO:2, SEQ ID NO:4, SEQ ID NO:105 or SEQ ID NO:106, promotes altered (e.g., increased or decreased in a statistically significant manner) immunological activity that results in immune system-potentiated killing of tumor cells and/or inhibition of tumor metastasis. By way of non-limiting theory, such altered immunological activity may be induced or promoted by binding of the herein described immunomodulatory polypeptide (e.g., the polypeptide which comprises SEQ ID NO:2, SEQ ID NO:4, SEQ ID NO:105 or SEQ ID NO:106) to one or more cognate receptors on immunologically active cells including neutrophils, or by interference with such binding by antibody blockade when an anti-PeptideX2 antibody is administered.

Neutrophil roles in cancer cell rejection and metastasis have been described, including in breast cancer, ovarian cancer, adenoma, colorectal, gastric, lung, prostate and hepatocellular carcinoma, melanoma, and hematologic (e.g., leukemia, lymphoma) and other malignancies (e.g., DiCarlo et al., 2001 *Blood* 97; 339; Mantovani et al., 2011 *Nat. Rev. Immunol.* 11:519; Gregory et al., 2011 *Canc. Res.* 71:2411; De Larco et al., 2004 *Clin. Canc. Rec.* 10:4895), as have antitumor effects of the known neutrophil products IL-6 and IL-10 (e.g., Li et al., 2010 *Canc. Chemother. Pharmacol.* 66:981; Mumm et al., 2011 *Canc. Cell* 20:781). As described herein for the first time and presented in greater detail below, the presently provided peptide X2 directly binds to neutrophils and also, after being contacted with neutrophil-containing peripheral blood leukocyte preparations, induces, inter alia, elaboration of IL-6 and IL-10. This effect on a local and/or systemic cytokine profile is thus believed to provide immunomodulatory properties of the herein described PeptideX2 and IgX polypeptides and/or of antibodies specific for such PeptideX2 or IgX polypeptides, through their alteration (e.g., statistically significant increases or decreases) in the activity levels of one or more cellular regulators of immune status. (See, e.g., DiCarlo et al., 2001 *Blood* 97; 339; Mantovani et al., 2011 *Nat. Rev. Immunol.* 11:519.)

The presence of a malignant condition in a subject refers to the presence of dysplastic, cancerous and/or transformed cells in the subject, including, for example neoplastic, tumor, non-contact inhibited or oncogenically transformed cells, or the like (e.g., carcinomas such as adenocarcinoma, squamous cell carcinoma, small cell carcinoma, oat cell carcinoma, etc., sarcomas such as chondrosarcoma, osteosarcoma, etc.) which are known to the art and for which criteria for diagnosis and classification are established (e.g., Hanahan and Weinberg, 2011 *Cell* 144:646; Hanahan and Weinberg 2000 *Cell* 100:57; Cavallo et al., 2011 *Canc. Immunol. Immunother.* 60:319; Kyrigideis et al., 2010 *J. Carcinog.* 9:3) In preferred embodiments contemplated by the present invention, for example, such cancer cells may be cells of mixed lineage leukemia, esophageal cancer, ovarian cancer, prostate cancer, kidney cancer, colon cancer, liver cancer, stomach cancer, breast cancer and pancreatic cancer, and other solid cancers. The precise dosage and duration of treatment is a function of the condition or disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The immunomodulatory-containing compositions may be administered alone or in combination with other known immunosuppressive treatments, such as monoclonal antibodies to lymphocytes and cytokine receptors (e.g., anti-IL-2Rα), calcineurin inhibitors (e.g., cyclosporine and tacrolimus), and cytokine receptor signal transduction inhibitors (e.g., sirolimus). The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described immunomodulatory polypeptide in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of an immunomodulatory polypeptide of the present disclosure, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of an immunomodulatory polypeptide as herein disclosed such that a suitable dosage will be obtained. Typically, this amount is at least 0.01% of the immunomodulatory polypeptide in the composition. When intended for oral administration, this amount may be varied to be between 0.1 and about 70% of the weight of the composition. Certain oral pharmaceutical compositions contain between about 4% and about 75% of the immunomodulatory polypeptide. In certain embodiments, pharmaceutical compositions and preparations according to the present invention are prepared so that a parenteral dosage unit contains between 0.01 to 10% by weight of the immunomodulatory polypeptide prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the immunomodulatory polypeptide according to certain embodiments of the invention and thereby assists in the delivery of the compound. Suitable agents that may act in this capacity include monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises an immunomodulatory polypeptide as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the peptide composition so as to facilitate dissolution or homogeneous suspension of the immunomodulatory polypeptide in the aqueous delivery system.

The compositions are administered in a therapeutically effective amount, which will vary depending upon a variety of factors including the activity of the specific compound (e.g., IgX or PeptideX2) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the immunomodulatory polypeptides of the present disclosure may also be administered simultaneously with, prior to, or after administration of one or more other therapeutic agents. Such combination therapy may include administration of a single pharmaceutical dosage formulation which contains a compound according to certain embodiments of the invention and one or more additional active agents, as well as administration of compositions comprising antibodies according to certain embodiments of the invention and each active agent in its own separate pharmaceutical dosage formulation. For example, an immunomodulatory polypeptide as described herein and the other active agent can be administered to the patient together in a single oral dosage composition such as a tablet or capsule, or each agent administered in separate oral dosage formulations. Similarly, an immunomodulatory polypeptide as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising antibodies and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of immunomodulatory polypeptide compositions of this disclosure in combination with one or more other therapeutic agents. Such therapeutic agents may be accepted in the art as a standard treatment for a particular disease state as described herein, such as rheumatoid arthritis, inflammation or preeclampsia. Exemplary therapeutic agents contemplated include cytokines, growth factors, steroids, NSAIDs, DMARDs, anti-inflammatories, chemotherapeutics, or other active and ancillary agents.

In various embodiments, the immunomodulatory polypeptides described herein are conjugated to a detectable label that may be detected directly or indirectly. In this regard, an immunomodulatory polypeptide "conjugate" refers to an immunomodulatory polypeptide that is covalently linked to a detectable label. In certain embodiments of the present invention, DNA probes, RNA probes, monoclonal antibodies, antigen-binding fragments thereof, and antibody derivatives thereof, such as a single-chain-variable-fragment antibody or an epitope tagged antibody, may all be covalently linked to a detectable label. In "direct detection", only one detectable antibody is used, i.e., a primary detectable antibody. Thus, direct detection means that the antibody that is conjugated to a detectable label may be detected, per se, without the need for the addition of a second antibody (secondary antibody).

A "detectable label" is a molecule or material that can produce a detectable (such as visually, electronically or otherwise) signal that indicates the presence and/or concentration of the label in a sample. When conjugated to a peptide, the detectable label can be used to locate and/or quantify the target to which the specific peptide is bound. Thereby, the presence and/or concentration of the target in a sample can be detected by detecting the signal produced by the detectable label. A detectable label can be detected directly or indirectly, and several different detectable labels conjugated to different specific-antibodies can be used in combination to detect one or more targets.

Examples of detectable labels, which may be detected directly, include fluorescent dyes and radioactive substances and metal particles. In contrast, indirect detection requires the application of one or more additional antibodies, i.e., secondary antibodies, after application of the primary antibody. Thus, the detection is performed by the detection of the binding of the secondary antibody or binding agent to the primary detectable antibody. Examples of primary detectable binding agents or antibodies requiring addition of a secondary binding agent or antibody include enzymatic detectable binding agents and hapten detectable binding agents or antibodies.

In some embodiments, the detectable label is conjugated to a nucleic acid polymer which comprises the first binding agent (e.g., in an ISH, WISH, or FISH process). In other embodiments, the detectable label is conjugated to an antibody which comprises the first binding agent (e.g., in an IHC process).

Examples of detectable labels which may be conjugated to immunomodulatory polypeptides used in the methods of the present disclosure include fluorescent labels, enzyme labels, radioisotopes, chemiluminescent labels, electrochemiluminescent labels, bioluminescent labels, polymers, polymer particles, metal particles, haptens, and dyes.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include micro particles or latex particles of polystyrene, PMMA or silica, which can be embedded with fluorescent dyes, or polymer micelles or capsules which contain dyes, enzymes or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphthol (CN), .alpha.-naphthol pyronin (.alpha.-NP), o-dianisidine (OD), 5-bromo-4-chloro-3-indolylphosp-hate (BCIP), Nitro blue tetrazolium (NBT), 2-(p-iodophenyl)-3-p-nitropheny-I-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/-fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

Detectable labels may be linked to the immunomodulatory polypeptides described herein or to any other molecule that specifically binds to a biological marker of interest, e.g., an antibody, a nucleic acid probe, or a polymer. Furthermore, one of ordinary skill in the art would appreciate that detectable labels can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.).

The invention also provides, in certain embodiments, kits for detecting immunomodulatory polypeptides (e.g., IgX or PeptideX2) or cells (e.g., neutrophils) in a sample, wherein the kits contain at least one antibody, polypeptide, polynucleotide, vector or host cell as described herein. In certain embodiments, a kit may comprise buffers, enzymes, labels, substrates, beads or other surfaces to which the antibodies of the invention are attached, and the like, and instructions for use.

EXAMPLES

Example 1

Identification of IgX

The modulation of the immune response during pregnancy has been the focus of numerous studies; however, the underlying mechanisms that modulate the maternal immune system to allow for implantation, placental entrenchment, the balance between pro-inflammatory and anti-inflammatory signals, and the eventual achievement of a full term pregnancy remain unclear. For example, it is unclear why a majority of women with rheumatoid arthritis experience disease amelioration during pregnancy. In order to identify naturally occurring immunoregulatory agents, placentas from healthy women were analyzed.

Placental Preparation

Placentas were obtained from healthy women using appropriate informed consent. The umbilical cord and embryonic sac were removed, the placenta was washed generously in physiologic saline three times, and it was homogenized using a blender at medium speed for 30 seconds followed by one minute at slow speed. Samples were then placed into conical tubes and centrifuged at 1400 g for 10 minutes. Supernatants were removed and stored. The pelleted tissue component was prepared by adding 10 ml of nanopure water to each individual conical tube, placing each tube on ice, sonicating each conical tube with placental tissue for 30 seconds, allowing it to cool for 3 minutes, and then repeating three times. Next, 50 cc of nanopure water was added to each conical tube and mixed to create a hypotonic solution and cause cell lysis. Each sample was diluted to 1:10,000 in merthiolate, incubated at 4° C. for 48 hours, then centrifuged at 1400 g for 25 minutes, and then the lysate was aspirated from the conical tube and stored as −20° C.

IgX Preparation

Frozen lysate from the placental tissue was thawed and centrifuged 10,000 g for 13 minutes. The resulting supernatant was collected, and 500 mg EDTA (all reagents were from Sigma, St. Louis, Mo., unless otherwise noted) was added to each tube and mixed well. The lysates were then incubated at room temperature for 30 minutes with gentle rocking. Then this solution was centrifuged 10,000 g for 13 minutes, the supernatant collected and treated with DNase/RNase preparation (1 mg/ml of each enzyme in total 1 ml stock solution) to make the sample 25 ug DNase and 25 ug RNase per 5 ml, incubated at 37° C. for one hour, then centrifuged 5000 g for 10 minutes, the supernatant collected, filtered with a 0.22 micron Millipore™ (Millipore Inc., Bedford, Mass.) filter. Samples of 5 ml each were applied to a HiPrep™ 26/60 Sephacryl™ S-200 HR column (GE Healthcare Bio-Sciences Corp., Piscataway, N.J.) at flow rate 1.0 ml/min in 0.05 M phosphate, 0.15 M NaCl buffered saline, pH 7.8. Fractions 30-33 (total 7 cc per run) were collected and concentrated using Millipore™ spin concentrators (nominal molecular weight limit 100 kDa). The resulting samples were diluted 1:1 with Protein A IgG Binding buffer (0.02 M Na citrate, 0.1M phosphate buffer, pH 7.4, Pierce Chemical Co., Rockford, Ill.), and applied to a Protein A column (5 ml Protein A/column) (Pierce). The column was then washed with binding buffer (10× column volume and repeated until an absorption reading of zero was observed), and then immunoglobulin was eluted with Immunopure™ IgG elution buffer (0.02 M Na citrate, 0.1M NaCl, pH 2.5, Pierce) at 1 ml/min. Fractions were collected, and samples were brought to a final concentration of 0.05 M phosphate, 0.15 M NaCl buffered saline, pH 7.4, using Millipore concentrators according to the manufacturer's recommendations by performing about 2-3 cycles of concentrating and then adding buffer. Protein concentrations were assayed using the BCA technique (Pierce) and then samples were stored at −20° C.

SDS-PAGE and Protein Identification

Samples were diluted to 1:5 in HES buffer (10 mM HEPES, 10 mM EDTA, 250 mM sucrose), and then diluted to 1:1 with reducing sample buffer (Pierce). The samples were then boiled for 10 minutes, and SDS-PAGE (8%) was performed to obtain separated immunoglobulin heavy (H) and light (L) chains. The gels were stained using Imperial Protein Stain (Pierce) in order to cut out the H and L chain bands. Proteomic analysis of the H and L chain bands was performed by ProtTech (Norristown, Pa.) using proprietary techniques and mass spectrometery. N-terminal amino acid sequencing of H and L chains was obtained by preparing H and L chains by SDS-PAGE, transferring H and L chains to polyvinylidene fluoride (PVDF) membranes, staining the membranes with MemCode™ Reversible Protein Stain Kit for PVDF membrane (Pierce), cutting out the H and L bands, and sending the bands to Alphalyze, Inc. (Palo Alto, Calif.) to perform the sequencing.

The placental tissue lysate samples from 11 donors were examined under reducing and non-reducing conditions using SDS-PAGE and showed an electrophoretic migration pattern suggesting, respectively, the intact form (non-reducing) of the immunoglobulin and the separated (reducing) H and L chains of immunoglobulin G. Since these results suggested a unique placental immunoglobulin G, henceforth this protein was identified as IgX. The bands corresponding to the H and L chains were sent for protein analysis and indeed showed the presence of H and L chains, but also some impurities.

In order to enhance the purification of these bands for protein analysis, the placental tissue lysates from four donors (RA, BC, MP, and KS) were treated under non-reducing conditions with gel filtration followed by protein A purification and then tested under reducing condition with SDS-PAGE. The H and L bands were sent for protein identification and cross matching with other protein sequences in the protein data bank and were found to have nearly identical sequences with each other and with an IgG1 H chain identified as GenBank accession number AAH90938.1 (SEQ ID NO:3, Table 1). The sequences were found to be nearly identical at residues 1-19, 133-157, 298-311, 325-343, 340-347, 368-383, 395-432, as shown by the alignments in Table 1.

The H bands and L bands from the SDS-PAGE gel were transferred to PVDF, stained, excised and sent for N-terminal amino acid sequencing. These results showed that sample KS had 70-80% credibility of having the AAH90938.1 N-terminal sequence EVQLVE (SEQ ID NO: 110), and the amino terminal sequence for sample BC H chain was also highly homologous to EVQLVE (SEQ ID NO: 110). Interestingly, the N-terminal sequence for sample BC H chain was identified as DVQLLE (SEQ ID NO: 111) by protein analysis using mass spectrometry. These N-terminal amino acid sequences were nearly identical to the amino acid sequence of AAH90938.1 at residues 19-24. Therefore, the preceding (upstream) residues were believed according to non-limiting theory to represent a signal sequence for the H chain.

TABLE 1

IgX H chain partial sequences from four different placental samples (SEQ ID NOS: 3, 112, 113, 114, 115):

```
AAH90938.1  mefglswvfl vailkgvqce vqlvesgggl vqpgrslrls ctssgftfgd yamnwvrqap gkglewvgfi rskpyggtte yaaslkgrft vsrddsksia
KS                              e vklvesgggl vqpgrslr--
MP                              e vklvesgggl vqpgrslr--
BC                              d vqllesgggl vqpggslr--
RA                              e vqlvesgggl vqpgrslr--

AAH90938.1  ylcqmnslkte dtalyyctrs lrgvqqpldy wggtlvtvs sastkgpsvf plapssksts ggtaalgclv kdyfpepvtv swnsgaltsg vhtfpaylqs
KS                                         --gtlvtvs sastkgpsvf plapssk---
MP                                         --gtlvtvs sastkgpsvf plapssk---
BC                                                            gpsvf plapssk---
RA                                                            gpsvf plapssk---

AAH90938.1  sglyslssvv tvpssslgtq tyicnvnhkp sntkvdkkve pkscdkthtc ppcpapellg gpsvflfppk pkdtlmisrt pevtcvvvdv shedpevkfn
KS                                                                                                                    fn
MP                                                                                                                    fn
BC                                                                                                                    fn
RA                                                                                                                    fn AAH90938.1  wyvdgvevhn aktkpreeqy nstyrvvsyl tvlhqdwlng keykckvsnk alpapiekti skakggqprep qvytlppsrd eltknqvslt clvkgfypsd
KS          wyvdgvevhn ak-------- ---------- --vvsyl tvlhqdwlng keyk------ ---------- ---------- ep qvytlppsr- ---------- gfypsd
MP          wyvdgvevhn ak-------- ---------- ---------- ---------- ---------- -alpapiek- ---------- ep qvytlppsre emtk------ gfypsd
BC          wyvdgvevhn ak-------- ---------- --vvsyl tvlhqdwlng keyk------ -alpapiek- ---------- ep qvytlppsre emtk------ gfypsd
RA          wyvdgvevhn ak-------- ---------- -vvvsyl yvlhqdwlng keyk------ -alpapiek- ---------- ep qvytlppsrd eltk------ gfypsd AAH90938.1  iavewesngq pennykttpp vldsdgsffl yskltvdksr wqqgnvfsc vmhealhnhy tqkslslspg k
KS          iavewesngq pennykttpp vldsdgsffl ysk--------
MP          iavewesngq pennykttpp vldsdgsffl ysk--------
BC          iavewesngq pennykttpp vldsdgsffl ysk--------
RA          iavewesngq pennykttpp vldsdgsffl ysk--------
```

SEQ ID NO: 3: (Acc. No. AAH90938.1 GI:60551126)
```
  1   MEFGLSWVFL VAILKGVQCE VQLVESGGGL VQPGRSLRLS CTSSGFTFGD YAMNWVRQAP

61   GKGLEWVGFI RSKPYGGTTE YAASLKGRFT VSRDDSKSIA YLQMNSLKTE DTALYYCTRS

121   LRGVQGPLDY WGQGTLVTVS SASTKGPSVF PLAPSSKSTS GGTAALGCLV KDYFPEPVTV

181   SWNSGALTSG VHTFPAVLQS SGLYSLSSVV TVPSSSLGTQ TYICNVNHKP SNTKVDKKVE

241   PKSCDKTHTC PPCPAPELLG GPSVFLFPPK PKDTLMISRT PEVTCVVVDV SHEDPEVKFN

301   WYVDGVEVHN AKTKPREEQY NSTYRVVSVL TVLHQDWLNG KEYKCKVSNK ALPAPIEKTI

361   SKAKGQPREP QVYTLPPSRD ELTKNQVSLT CLVKGFYPSD IAVEWESNGQ PENNYKTTPP

421   VLDSDGSFFL YSKLTVDKSR WQQGNVFSCS VMHEALHNHY TQKSLSLSPG K
```
(Strausberg et al., 2002 Proc. Nat. Acad. Sci. 99:16899)

Example 2

IgX Induces Cytokine Production

In order to examine the biological activity of IgX, cytokine production from human peripheral whole blood samples incubated with IgX was measured. Peripheral whole blood samples from three different donors (#66, 67, and 85) were obtained with appropriate informed consent and incubated with concentrations of IgX ranging from 0 to 200 ug/ml.

Cytokine Analysis

Protein A purified IgX was prepared from placental sample BC, brought to 0.05 M phosphate, 0.15 M NaCl buffer, pH 7.4, treated with an endotoxin affinity column (ActiClean Etox™ from Sterogene, Carlsbad, Calif.) according to the supplier's instructions, and then sent to IBT Biosciences (Gaithersburg, Md.) for human peripheral blood testing. This sample was found to have 1 EU/ml of endotoxin per 10 ug/ml of sample. All peripheral blood cells were suspended in RPMI-1640 media. Various concentrations of IgX were incubated with peripheral blood cells from donor D66 (50 y/o female) for 18 hours, and then the samples were stimulated with 1 ug/ml of PHA, 50 ng/ml of LPS, or 10 ng/ml of IFNγ (200 U/ml) for four hours. Samples of culture supernatant fluids were tested in duplicate for the presence of IL-2, IL-4, IL-6, IL-10, IL-12, and TNFα using a Meso Scale Discovery (MSD, Gaithersburg, Md.) panel.

Figure 2:
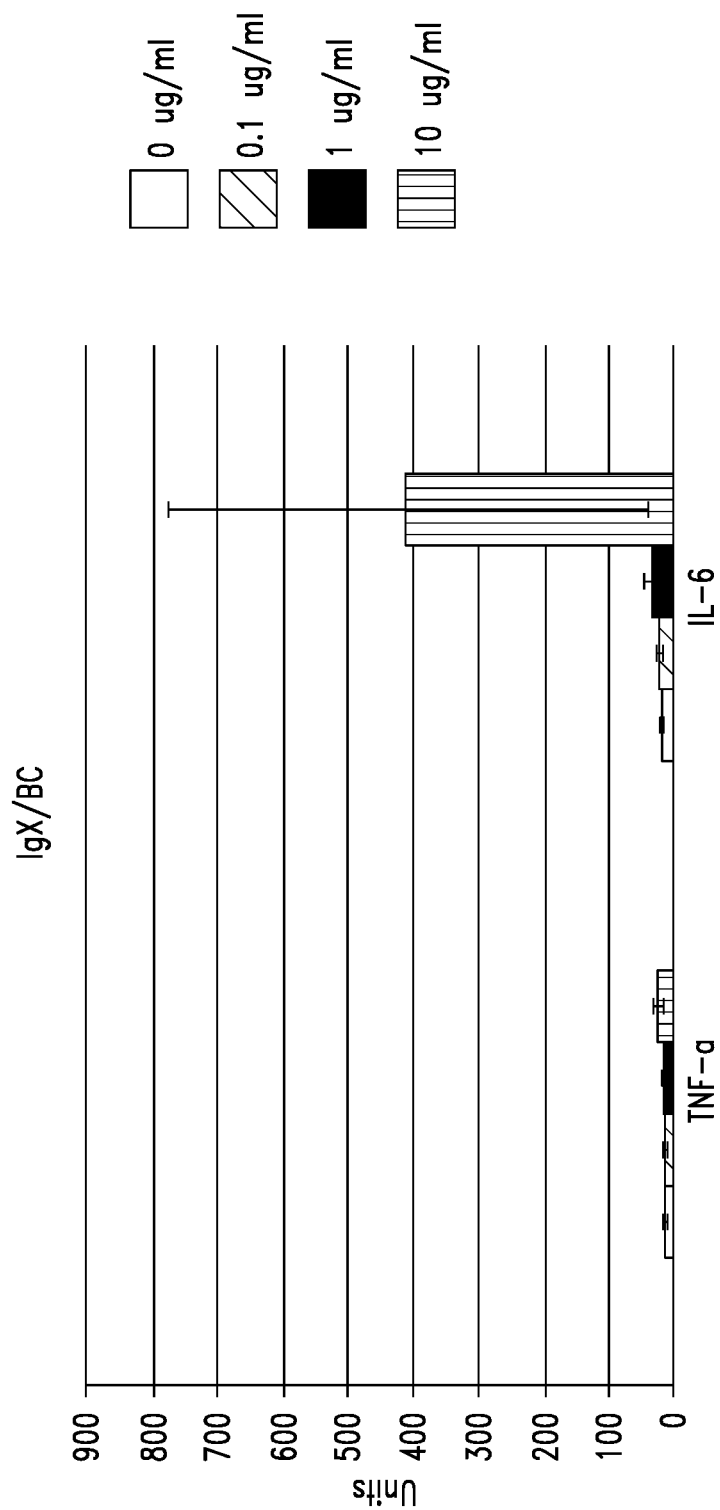
FIG. 2 is a bar graph that shows TNFα and IL-6 produced by whole peripheral blood cells from Donor #66 in response to culture with 0, 0.1, 1 or 10 ug/ml IgX derived from placental sample BC.
Figure 3:
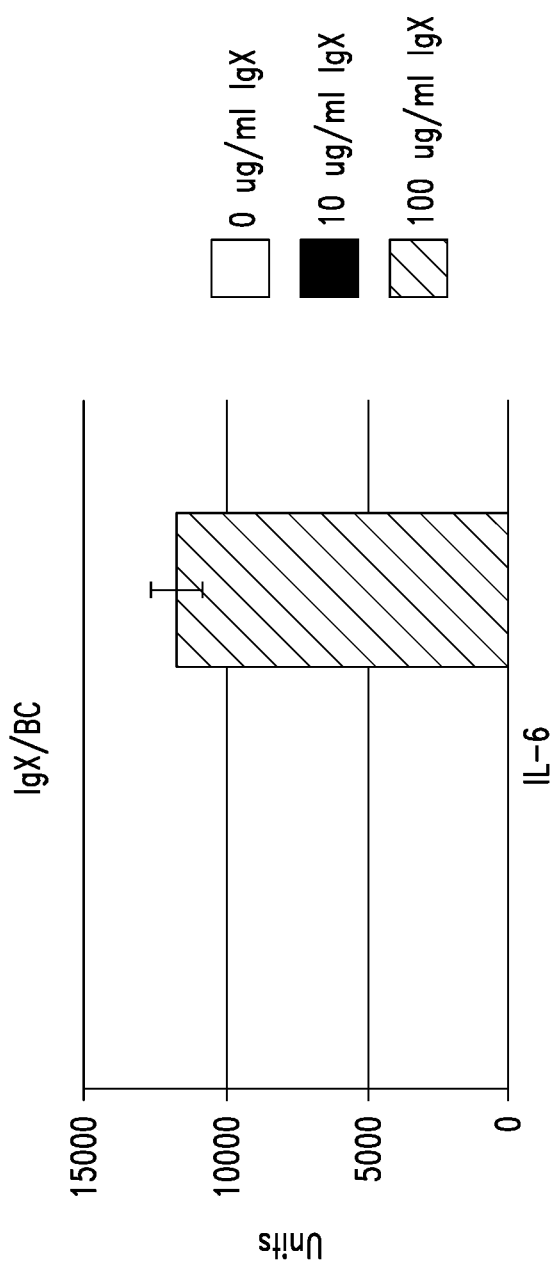
FIG. 3 is a bar graph that shows IL-6 produced by whole peripheral blood cells from Donor #67 in response to culture with 0, 10 or 100 ug/ml IgX derived from placental sample BC.
Figure 4:
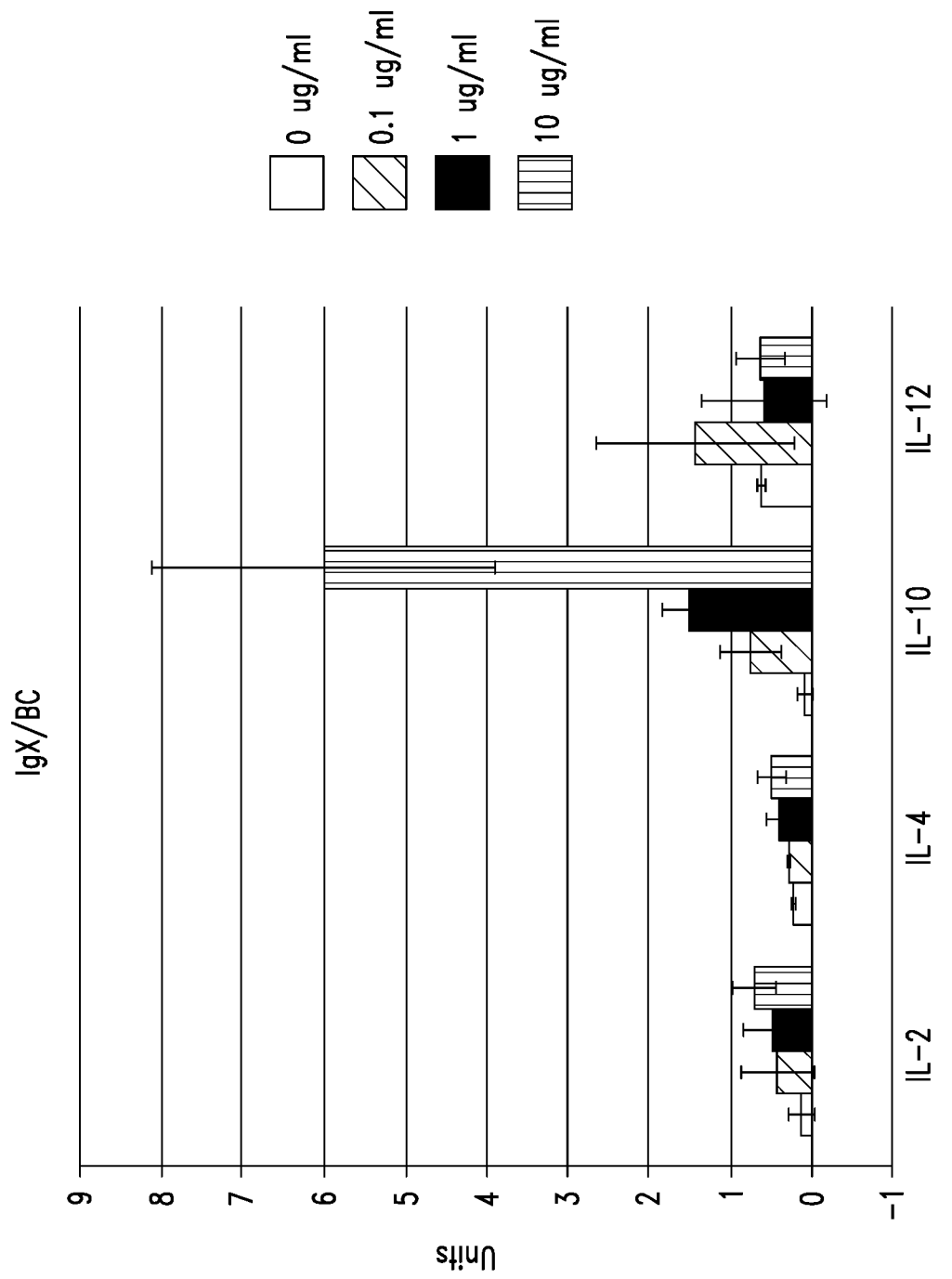
FIG. 4 is a bar graph that shows IL-2, IL-4, IL-10 and IL-12 produced by whole peripheral blood cells from Donor #85 in response to culture with 0, 10, 100 or 200 ug/ml IgX derived from placental sample BC.
Figure 5:
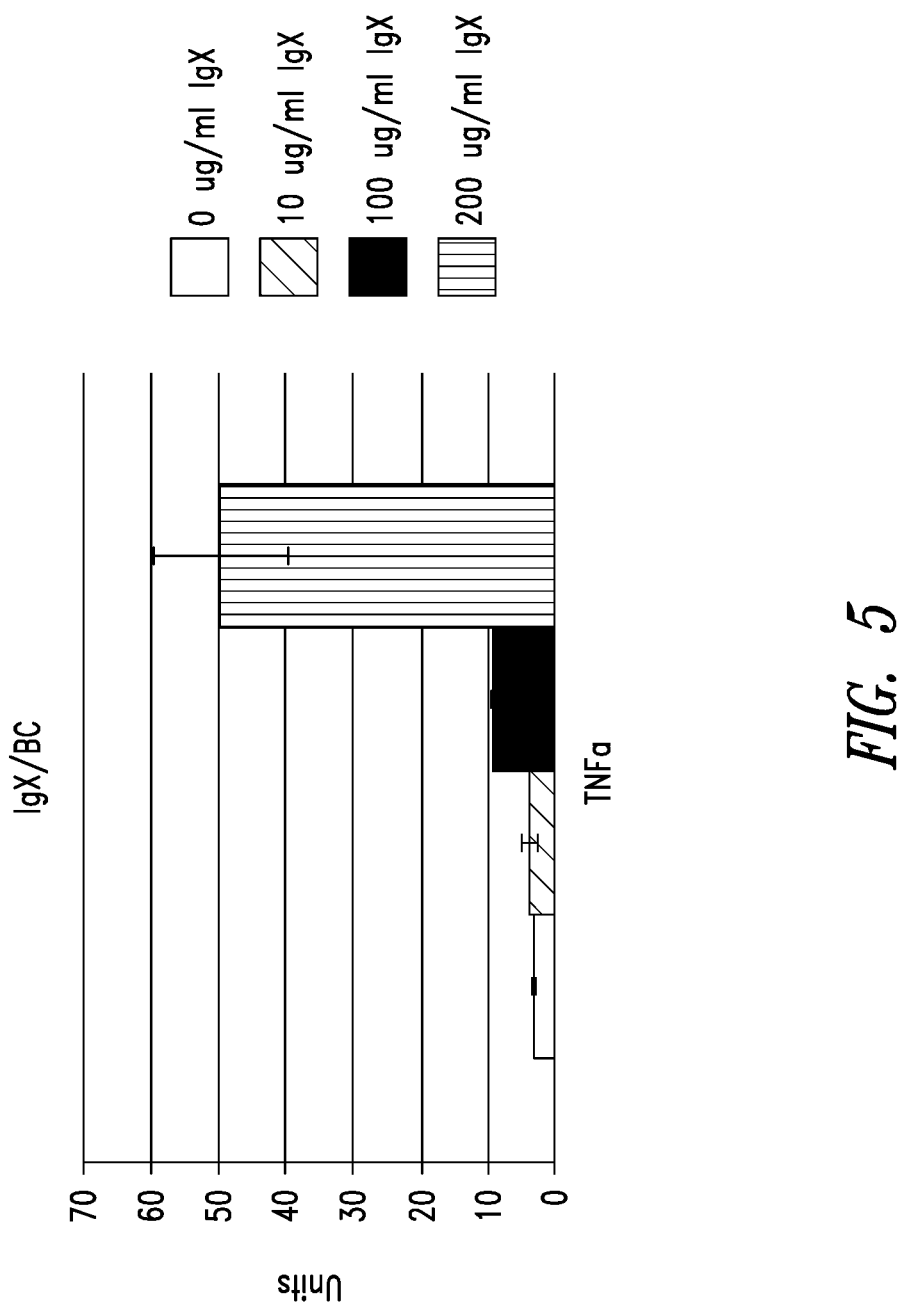
FIG. 5 is a bar graph that shows TNFα produced by whole peripheral blood cells from Donor #85 in response to culture with 0, 10, 100 or 200 ug/ml IgX derived from placental sample BC.
Figure 6:
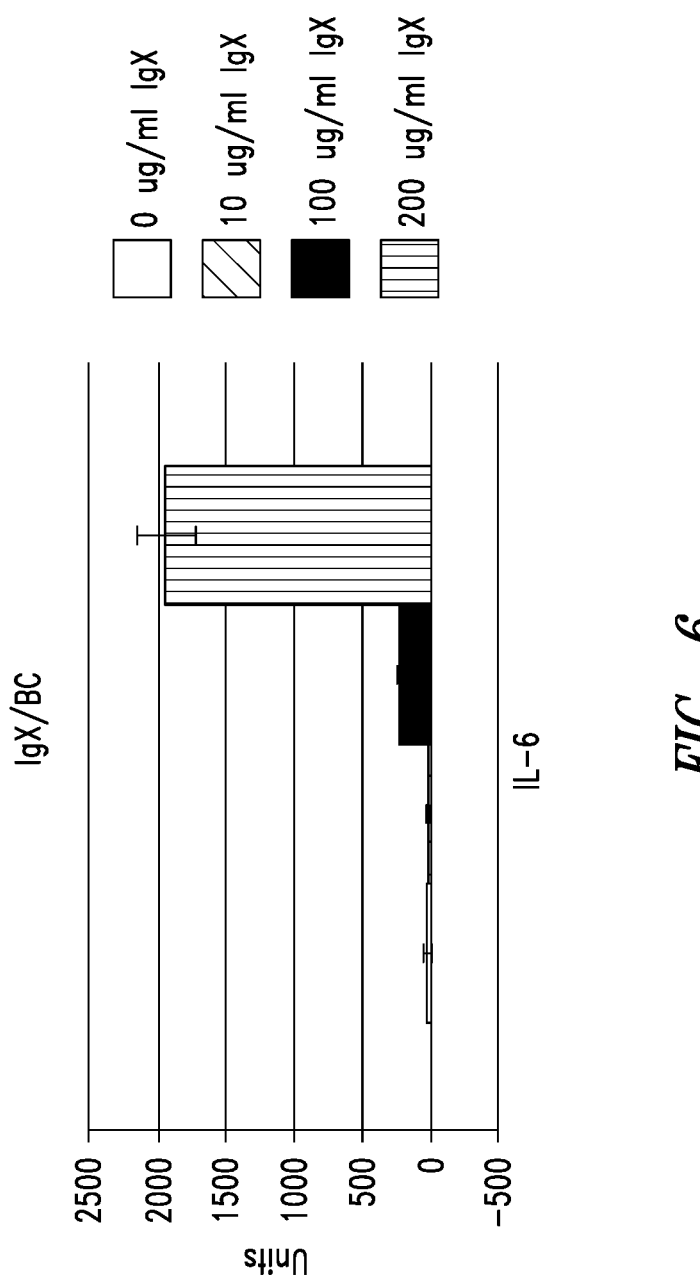
FIG. 6 is a bar graph that shows IL-6 produced by whole peripheral blood cells from Donor #85 in response to culture with 0, 10, 100 or 200 ug/ml IgX derived from placental sample BC.

Production of the cytokines IL-2, IL-4, IL-6, IL-10, IL-12, and TNFα was determined for peripheral blood cells following exposure to IgX. Cells from donor #66 were sensitive to lower doses of IgX compared to the other donors, and these cells showed a significant increase in IL-6 production and, to a lesser degree, an increase in TNFα production at 10 ug/ml IgX (FIGS. 1 and 2). Cells from the other donors showed a significant increase in IL-6 and, to a lesser degree, an increase in TNFα, at higher concentrations of IgX ranging from 100 to 200 ug/ml (FIGS. 3, 5 and 6). Cells from donor #85 also had a slight increase in IL-10 production at 200 ug/ml IgX (FIG. 4). There was no significant increase in the other cytokines measured (i.e., IL-2, IL-4 and IL-12). IgX did not appear to have an immunosuppressive effect on peripheral blood cells when incubated in the presence of LPS, PHA or IFNγ.

Example 3

Active Fragments of IgX

In order to determine if the immunomodulating potential of IgX lies within the Vh hypervariable region of AAH90938.1 (SEQ ID NO:3), peptides comprising amino acid sequences that corresponded to the third hypervariable region and third framework region were prepared. PeptideX1 had the amino acid sequence AEDTAVYYCAR (SEQ ID NO:1) of the H chain of sample BC, which shared 73% homology with AAH90938.1 at residues 109-119. Peptide X2 had the amino acid sequence KSIAYLQMNSLK (SEQ ID NO:2) that corresponded to residues 97-108 of the H chain of AAH90938.1.

Peptide Preparation

PeptideX1 and PeptideX2 were synthesized by Genscript, Inc. (Piscataway, N.J.) and solubilized by adding 50 ul of 10% acetic acid to 2 mg of sample. Then 450 ul of 0.1 M Tris buffer was added to each sample to provide a total volume of 500 ul at pH 7. Genscript also prepared conjugates of peptideX2-FITC (fluorescein isothiocyanate) with the fluoroprobe attached to the COOH end of peptideX2. 2 mg peptideX2-FITC was solubilized by adding 20 ul of 5% acetic acid solution, and then 980 ul of 0.01 M phosphate buffered saline, pH 6, was slowly added.

Cytokine Analysis

PeptideX1 and PeptideX2 were incubated with peripheral blood cells from donor D67 (30 y/o female) as described above and tested in duplicate for IL-6 activity. Another set of experiments examined peptideX2 and IgX, both prepared in 0.1 M Tris buffer, pH 7, and incubated with peripheral blood cells from donor D68 (27 y/o female). IgX was made endotoxin free by adding 4 ml of IgX 0.1 M Tris, pH 8.8, to a Strong Anion Exchange Spin Column (Pierce), centrifuging at 200×g for 5 minutes, washing twice with sterile 0.1 M Tris, pH 8.8, eluting from the membrane with two washes with sterile 0.1 M Tris, pH 7.2, and then concentrating the sample. All peripheral blood cells were suspended in RPMI-1640 media.

Flow Cytometry

Peripheral blood samples in EDTA were obtained with appropriate informed consent. 4 ml of ACK lysis buffer was added for every 4 ml of blood sample and allowed to mix in a 50 ml conical tube for 3-5 minutes at room temperature. The sample was centrifuged at 350 g for 5 minutes and the supernatant was discarded. Next, 2 ml of ACK lysis buffer was added and gently mixed with the cells prior to incubating the sample for 3-5 minutes. The sample was then centrifuged at 350×g for 5 minutes, and the supernatant was discarded. Next, 500 ul of stock Fc blocking solution (consisting of 40 ul of Fc blocking solution from eBiosciences, Inc. (San Diego, Calif.) plus 1 ml of 0.01 M phosphate buffered saline and 3% BSA) was added to the cell pellet and mixed gently for 10 minutes at room temperature. 100 ul aliquots were prepared with various concentrations of peptideX2-FITC and 1 ul of anti-CD markers (CD5-APC, CD14-PE, CD181-PE-Cy5, CD56-PE-Cy5) for each test sample and incubated for 15 min at room temperature. The reactions were stopped by adding 900 ul of cold PBS followed by centrifugation at 9000×g for 3 minutes. Supernatants were decanted, and the cold PBS wash with gentle vortexing was repeated with centrifugation following again, at 5800 rpm for 3 minutes. The supernatant was decanted again. The washing process was repeated a total of three times. After washing, 1 ml of 0.1% Triton X-100 in PBS was added and gently mixed with the cells. The cells were incubated at room temperature for 10 minutes before centrifuging at 5800 rpm for 3 min minutes and decanting the supernatant. Next, 500 ul of 1% paraformaldehyde in PBS was added to the cells and mixed gently. The cells were incubated for 10 min and then stored in the dark at 4° C. for up to 3 days. Results were acquired using a FACS-CALIBUR™ BD 4 Color flow cytometer (Becton Dickinson & Co., Rockville, Md.) according to the manufacturer's instructions. A macrophage cell line (THP-1) treated with 2 mg LPS incubated for 12 hours and without LPS was also examined. Following the 12 hour incubation with or without LPS, peptideX2-FITC was added at various concentrations and incubated for 15 minutes. The cells were then treated as described above and analyzed using flow cytometry.

Figure 7:
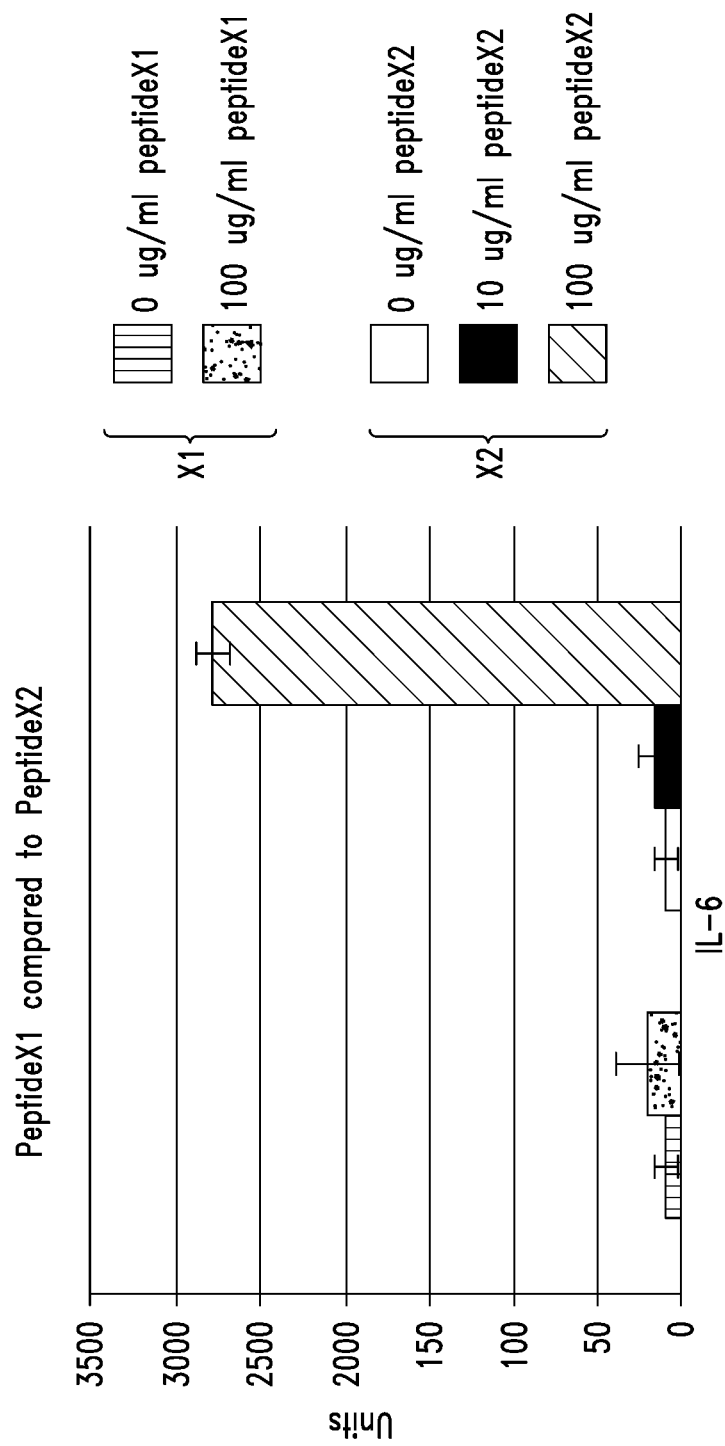
FIG. 7 is a bar graph that shows IL-6 produced by peripheral blood cells from Donor #67 in response to culture with PeptideX1 or PeptideX2.
Figure 8:
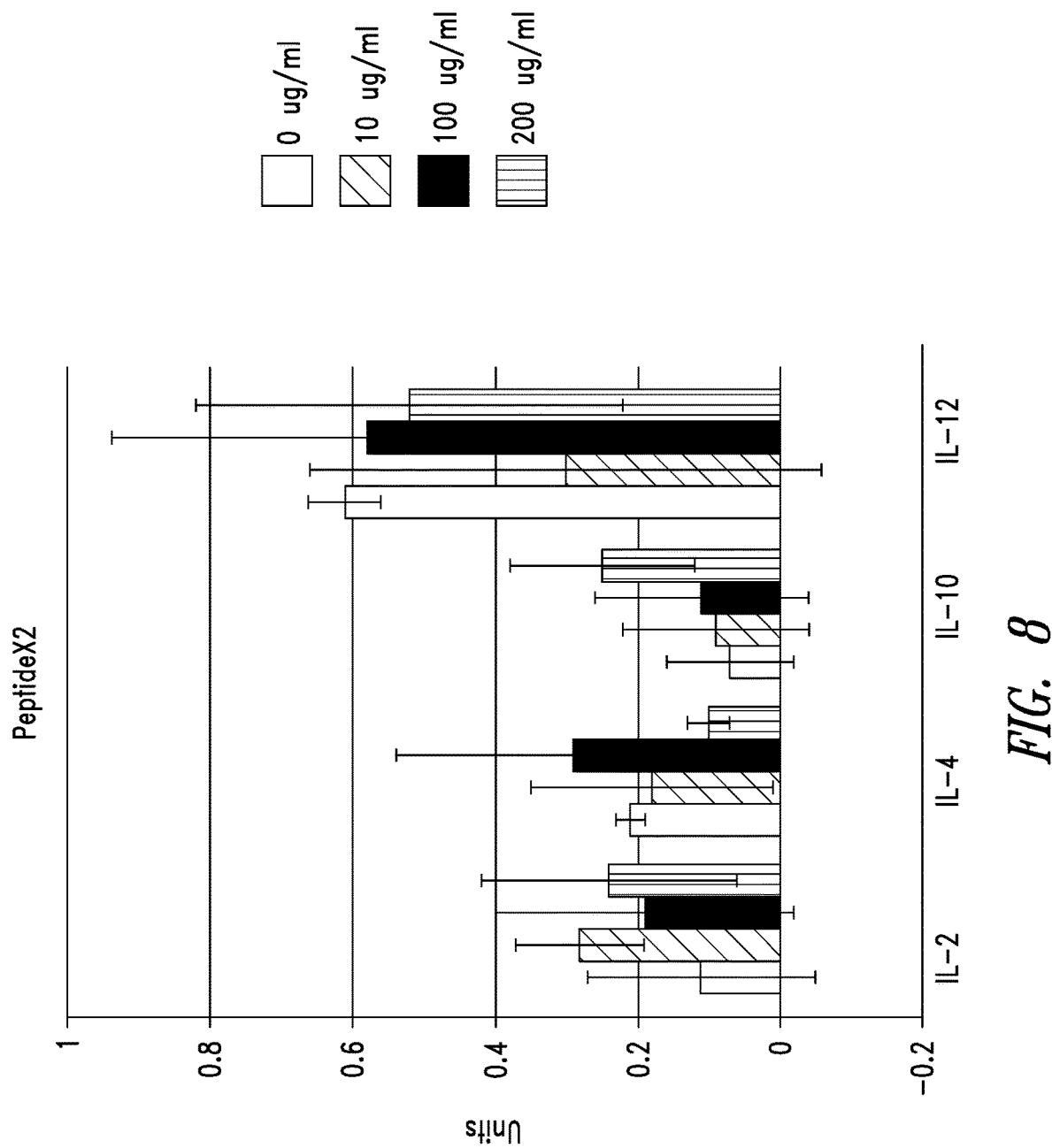
FIG. 8 is a bar graph that shows IL-2, IL-4, IL-10 and IL-12 produced by peripheral blood cells from Donor #85 in response to culture with 0, 10, 100 or 200 ug/ml PeptideX2.
Figure 9:
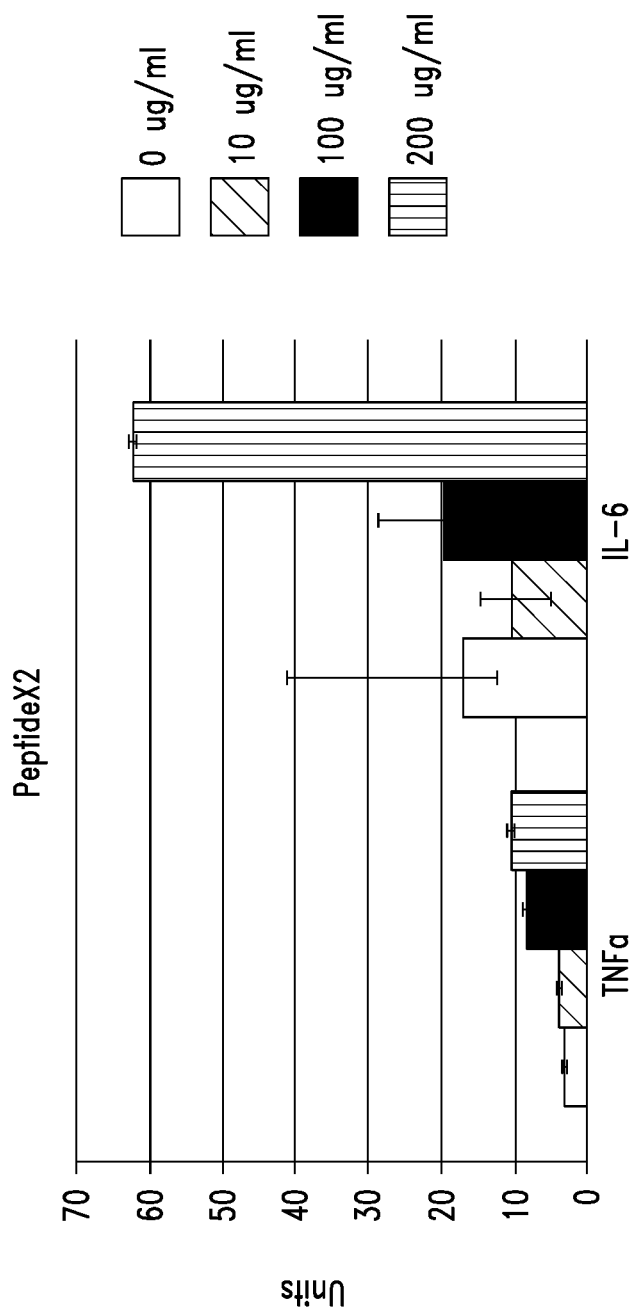
FIG. 9 is a bar graph that shows TNFα and IL-6 produced by peripheral blood cells from Donor #85 in response to culture with 0, 10, 100 or 200 ug/ml PeptideX2

Using cells from donor #67, peptideX2 induced a significantly greater IL-6 production compared to peptideX1 (FIG. 7). PeptideX2 was tested again using cells from a different donor (#85), and again it was found to induce enhanced production of IL-6 and, to a lesser degree, TNFα and IL-10 (FIGS. 8 and 9).

Figure 10:
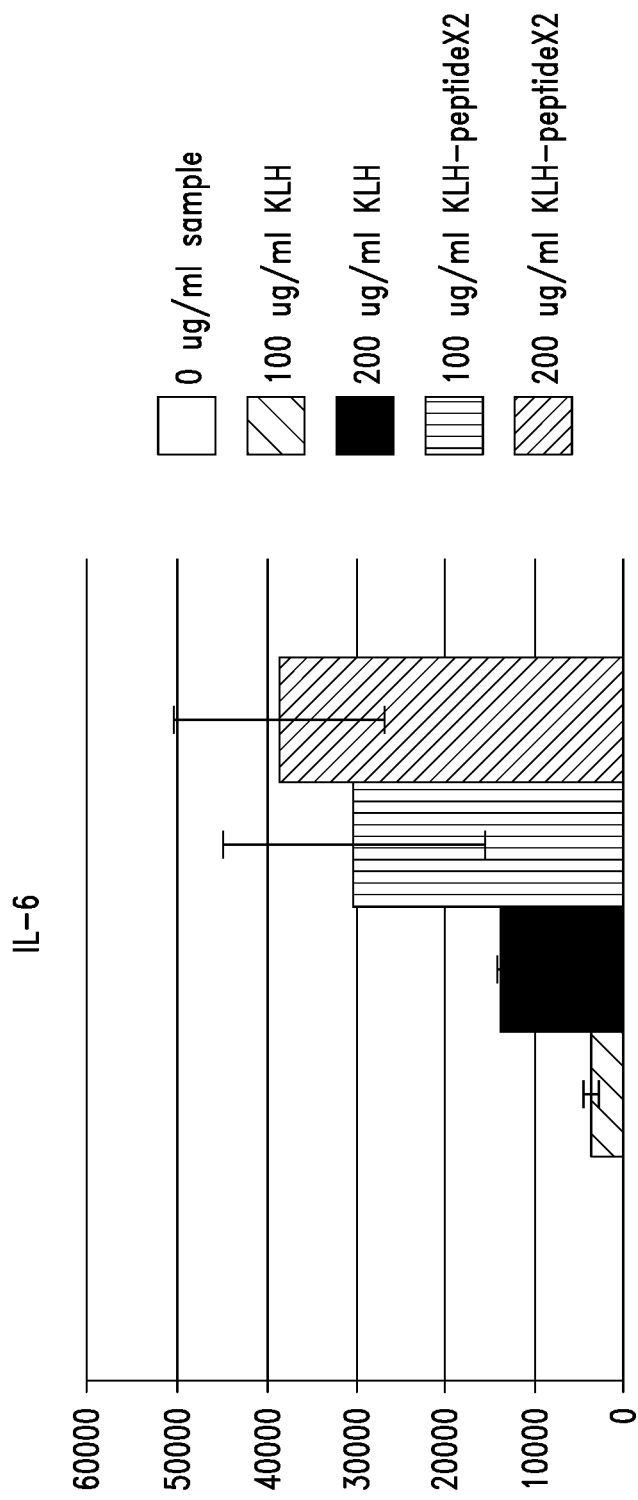
FIG. 10 is a bar graph that shows IL-6 produced by peripheral blood cells in response to culture with 100 or 200 ug/ml of KLH or PeptideX2-KLH conjugate.

In order to study the cell binding of pepideX2, the fluorescent conjugate peptideX2-FITC was prepared. However, it was important to determine whether or not conjugating the FITC to the COOH end of peptideX2 would alter its biological activity. Therefore, keyhole limpet hemocyanin (KLH) was conjugated to peptideX2 at its COOH end, and the biological activity was tested and found to be intact. In fact, KLH-peptideX2 had a significant positive impact on the production of IL-6 (FIG. 10). PeptideX2-FITC and antibodies for cell markers were incubated with human peripheral blood cells and prepared for flow cytometry. Surprisingly, PeptideX2-FITC bound to a subset of neutrophils but did not bind to NK cells, T cells, monocytes, and B cells at concentrations less than 20 ug/ml. Some nonspecific binding was observed at concentrations greater than 20 ug/ml. PeptideX2 was also incubated in the presence or absence of LPS in a monocyte cell line but without any binding.

Example 4

Amino Acid Sequence Homology to PeptideX2

In order to determine if there were any reported peptides having a high percentage of amino acid sequence identity to the 12 amino acid sequence of PeptideX2 [SEQ ID NO:2], a BLAST search of the NCBI amino acid sequence database was performed. Table 2 is a summary of the results, which revealed 100 polypeptides having sequences that included the 12 contiguous amino acids of SEQ ID NO:2. All of the amino acid sequences identified were human immunoglobulin G1 Vh domains of 67 amino acids in length or longer, derived from IgG1(K) immunoglobulins, and each one included, at varying positions within the sequence, the dodecameric PeptideX2 sequence, KSIALYQMNSLK (SEQ ID NO:2).

Homologues of the dodecameric PeptideX2 sequence (SEQ ID NO:2) were also identified as sequence variants that were present in murine and rat immunoglobulin heavy chain amino acid sequences in the database, where such variants differed from SEQ ID NO:2 at no more than 5, 4, 3, 2 or 1 positions within the amino acid dodecamer, such differences being present as substitutions, deletions or insertions. Relative to the human sequence in which SEQ ID NO:2 was identified, a greater number of variants was found among murine sequences than among rat sequences, suggesting evolutionary conservation of SEQ ID NO:2. Certain of the presently contemplated embodiments, however, may employ at least 1, 2, 3, 4 or 5 of the presently described SEQ ID NO:2 variants through generation of variant PeptideX2 structures that comprise the amino acid sequence of general formula:

K-X1-X2-X3-YLQM-X4-X5-LK as set forth in SEQ ID NO:106, wherein X1 is selected from S and N, X2 is selected from I, T, S, M, R and N, X3 is selected from A, L, V and Q, X4 is selected from N, D, S, T and A, and X5 is selected from S, T and N.

TABLE 2

Sequences producing significant alignments with PeptideX2

| SEQ ID NO: | Accession | Description | Max score | Total score | Query coverage | E value |
|---|---|---|---|---|---|---|
| 5 | ADW08230.1 | immunoglobulin heavy chain variable region [Homo sapiens] | 41.8 | 41.8 | 100% | 0.012 |
| 6 | ADW08228.1 | immunoglobulin heavy chain variable region [Homo sapiens] | 41.8 | 41.8 | 100% | 0.012 |
| 7 | ADW08227.1 | immunoglobulin heavy chain variable region [Homo sapiens] | 41.8 | 41.8 | 100% | 0.012 |
| 8 | ADX89690.1 | immunoglobulin epsilon heavy chain variable region [Homo sapiens] | 41.8 | 41.8 | 100% | 0.012 |
| 9 | ADX89674.1 | immunoglobulin epsilon heavy chain variable region [Homo sapiens] | 41.8 | 41.8 | 100% | 0.012 |
| 10 | ADX65711.1 | immunoglobulin variable region [Homo sapiens] | 41.8 | 41.8 | 100% | 0.012 |
| 11 | ADX65652.1 | immunoglobulin variable region [Homo sapiens] | 41.8 | 41.8 | 100% | 0.012 |
| 12 | ADX65553.1 | immunoglobulin variable region [Homo sapiens] | 41.8 | 41.8 | 100% | 0.012 |
| 13 | ADX65550.1 | immunoglobulin variable region [Homo sapiens] >gb\|ADX65551.1\| immunoglobulin variable region [Homo sapiens] | 41.8 | 41.8 | 100% | 0.012 |
| 14 | ADX65549.1 | immunoglobulin variable region [Homo sapiens] | 41.8 | 41.8 | 100% | 0.012 |
| 15 | ADX65548.1 | immunoglobulin variable region [Homo sapiens] | 41.8 | 41.8 | 100% | 0.012 |
| 16 | ADX65545.1 | immunoglobulin variable region [Homo sapiens] | 41.8 | 41.8 | 100% | 0.012 |
| 17 | ADX65526.1 | immunoglobulin variable region [Homo sapiens] >gb\|ADX65541.1\| immunoglobulin variable region [Homo sapiens] >gb\|ADX65542.1\| immunoglobulin variable region [Homo sapiens] | 41.8 | 41.8 | 100% | 0.012 |

TABLE 2-continued

Sequences producing significant alignments with PeptideX2

| SEQ ID NO: | Accession | Description | Max score | Total score | Query coverage | E value |
|---|---|---|---|---|---|---|
| 18 | ADU57684.1 | anti-vaccinia virus immunoglobulin heavy chain variable region [Homo sapiens] | 41.8 | 41.8 | 100% | 0.012 |
| 19 | ADQ01609.1 | immunoglobulin heavy chain variable region [Homo sapiens] >gb|ADQ01610.1| immunoglobulin heavy chain variable region [Homo sapiens] >gb|ADQ01662.1| immunoglobulin heavy chain variable region [Homo sapiens] >gb|ADQ01681.1| immunoglobulin heavy chain variable region [Homo sapiens] >gb|ADQ01683.1| immunoglobulin heavy chain variable region [Homo sapiens] | 41.8 | 41.8 | 100% | 0.012 |
| 20 | ADM44271.1 | immunoglobulin gamma 1 heavy chain variable region [Homo sapiens] | 41.8 | 41.8 | 100% | 0.012 |
| 21 | ADM43803.1 | immunoglobulin gamma 3 heavy chain variable region [Homo sapiens] | 41.8 | 41.8 | 100% | 0.012 |
| 22 | ADD14319.1 | immunoglobulin heavy chain [Homo sapiens] | 41.8 | 41.8 | 100% | 0.012 |
| 23 | ADD14256.1 | immunoglobulin heavy chain [Homo sapiens] | 41.8 | 41.8 | 100% | 0.012 |
| 24 | BAI51461.1 | immunoglobulin heavy chain variable region [Homo sapiens] | 41.8 | 41.8 | 100% | 0.012 |
| 25 | BAI51432.1 | immunoglobulin heavy chain variable region [Homo sapiens] | 41.8 | 41.8 | 100% | 0.012 |
| 26 | BAI52610.1 | immunoglobulin heavy chain variable region [Homo sapiens] | 41.8 | 41.8 | 100% | 0.012 |
| 27 | BAI52607.1 | immunoglobulin heavy chain variable region [Homo sapiens] | 41.8 | 41.8 | 100% | 0.012 |
| 28 | BAI52605.1 | immunoglobulin heavy chain variable region [Homo sapiens] | 41.8 | 41.8 | 100% | 0.012 |
| 29 | BAI52598.1 | immunoglobulin heavy chain variable region [Homo sapiens] | 41.8 | 41.8 | 100% | 0.012 |
| 30 | BAI52406.1 | immunoglobulin heavy chain variable region [Homo sapiens] | 41.8 | 41.8 | 100% | 0.012 |
| 31 | BAI52390.1 | immunoglobulin heavy chain variable region [Homo sapiens] | 41.8 | 41.8 | 100% | 0.012 |
| 32 | BAI52365.1 | immunoglobulin heavy chain variable region [Homo sapiens] | 41.8 | 41.8 | 100% | 0.012 |
| 33 | BAI52322.1 | immunoglobulin heavy chain variable region [Homo sapiens] | 41.8 | 41.8 | 100% | 0.012 |
| 34 | BAI52220.1 | immunoglobulin heavy chain variable region [Homo sapiens] | 41.8 | 41.8 | 100% | 0.012 |
| 35 | BAI52189.1 | immunoglobulin heavy chain variable region [Homo sapiens] | 41.8 | 41.8 | 100% | 0.012 |
| 36 | BAI52163.1 | immunoglobulin heavy chain variable region [Homo sapiens] | 41.8 | 41.8 | 100% | 0.012 |
| 37 | BAI52156.1 | immunoglobulin heavy chain variable region [Homo sapiens] | 41.8 | 41.8 | 100% | 0.012 |
| 38 | BAI52150.1 | immunoglobulin heavy chain variable region [Homo sapiens] | 41.8 | 41.8 | 100% | 0.012 |
| 39 | BAI52017.1 | immunoglobulin heavy chain variable region [Homo sapiens] | 41.8 | 41.8 | 100% | 0.012 |
| 40 | BAI52008.1 | immunoglobulin heavy chain variable region [Homo sapiens] | 41.8 | 41.8 | 100% | 0.012 |
| 41 | BAI51980.1 | immunoglobulin heavy chain variable region [Homo sapiens] | 41.8 | 41.8 | 100% | 0.012 |
| 42 | BAI51969.1 | immunoglobulin heavy chain variable region [Homo sapiens] | 41.8 | 41.8 | 100% | 0.012 |
| 43 | BAI51874.1 | immunoglobulin heavy chain variable region [Homo sapiens] | 41.8 | 41.8 | 100% | 0.012 |
| 44 | BAI51746.1 | immunoglobulin heavy chain variable region [Homo sapiens] | 41.8 | 41.8 | 100% | 0.012 |
| 45 | BAI51738.1 | immunoglobulin heavy chain variable region [Homo sapiens] | 41.8 | 41.8 | 100% | 0.012 |
| 46 | BAI51639.1 | immunoglobulin heavy chain variable region [Homo sapiens] | 41.8 | 41.8 | 100% | 0.012 |
| 47 | BAI51627.1 | immunoglobulin heavy chain variable region [Homo sapiens] | 41.8 | 41.8 | 100% | 0.012 |
| 48 | BAI51598.1 | immunoglobulin heavy chain variable region [Homo sapiens] | 41.8 | 41.8 | 100% | 0.012 |
| 49 | BAI51315.1 | immunoglobulin heavy chain variable region [Homo sapiens] | 41.8 | 41.8 | 100% | 0.012 |
| 50 | BAI50966.1 | immunoglobulin heavy chain variable region [Homo sapiens] | 41.8 | 41.8 | 100% | 0.012 |
| 51 | ACR16225.1 | immunoglobulin heavy chain variable region [Homo sapiens] | 41.8 | 41.8 | 100% | 0.012 |
| 52 | ACR16214.1 | immunoglobulin heavy chain variable region [Homo sapiens] | 41.8 | 41.8 | 100% | 0.012 |
| 53 | ACR16203.1 | immunoglobulin heavy chain variable region [Homo sapiens] | 41.8 | 41.8 | 100% | 0.012 |
| 54 | ACT68811.1 | immunoglobulin heavy chain variable region [Homo sapiens] | 41.8 | 41.8 | 100% | 0.012 |
| 55 | ACE75034.1 | immunoglobulin heavy chain variable region [Homo sapiens] | 41.8 | 41.8 | 100% | 0.012 |
| 56 | ACN43624.1 | immunoglobulin heavy chain variable region [Homo sapiens] | 41.8 | 41.8 | 100% | 0.012 |
| 57 | CAR62757.1 | immunoglobulin heavy chain variable region [Homo sapiens] | 41.8 | 41.8 | 100% | 0.012 |
| 58 | CAP78944.1 | immunoglobulin heavy chain variable region [Homo sapiens] >gb|ADQ01474.1| immunoglobulin heavy chain variable region [Homo sapiens] >gb|ADQ01475.1| immunoglobulin heavy chain variable region [Homo sapiens] >gb|ADQ01482.1| immunoglobulin heavy chain variable region [Homo sapiens] >gb|ADQ01514.1| immunoglobulin heavy chain variable region [Homo sapiens] >gb|ADQ01549.1| immunoglobulin heavy chain variable region [Homo sapiens] >gb|ADQ01563.1| immunoglobulin heavy chain variable region [Homo sapiens] | 41.8 | 41.8 | 100% | 0.012 |
| 59 | CAP78943.1 | immunoglobulin heavy chain variable region [Homo sapiens] >gb|ADQ01245.1| immunoglobulin heavy chain variable region [Homo sapiens] >gb|ADQ01263.1| immunoglobulin heavy chain variable region [Homo sapiens] >gb|ADQ01299.1| immunoglobulin heavy chain variable region [Homo sapiens] >gb|ADQ01358.1| immunoglobulin heavy chain variable region [Homo sapiens] >gb|ADQ01505.1| immunoglobulin heavy chain variable region [Homo sapiens] >gb|ADQ01599.1| immunoglobulin heavy chain variable region [Homo sapiens] | 41.8 | 41.8 | 100% | 0.012 |
| 60 | ABW80076.1 | immunoglobulin heavy chain variable region [Homo sapiens] | 41.8 | 41.8 | 100% | 0.012 |
| 61 | ABW79987.1 | immunoglobulin heavy chain variable region [Homo sapiens] | 41.8 | 41.8 | 100% | 0.012 |
| 62 | ABW79941.1 | immunoglobulin heavy chain variable region [Homo sapiens] | 41.8 | 41.8 | 100% | 0.012 |
| 63 | ABP98602.1 | immunoglobulin heavy chain variable region [Homo sapiens] | 41.8 | 41.8 | 100% | 0.012 |
| 64 | ABP98457.1 | immunoglobulin heavy chain variable region [Homo sapiens] | 41.8 | 41.8 | 100% | 0.012 |
| 65 | ABP98369.1 | immunoglobulin heavy chain variable region [Homo sapiens] | 41.8 | 41.8 | 100% | 0.012 |
| 66 | ABP98398.1 | immunoglobulin heavy chain variable region [Homo sapiens] | 41.8 | 41.8 | 100% | 0.012 |
| 67 | ABP98334.1 | immunoglobulin heavy chain variable region [Homo sapiens] | 41.8 | 41.8 | 100% | 0.012 |
| 68 | ABP98180.1 | immunoglobulin heavy chain variable region [Homo sapiens] | 41.8 | 41.8 | 100% | 0.012 |
| 69 | ABP98113.1 | immunoglobulin heavy chain variable region [Homo sapiens] | 41.8 | 41.8 | 100% | 0.012 |
| 70 | ABP98000.1 | immunoglobulin heavy chain variable region [Homo sapiens] | 41.8 | 41.8 | 100% | 0.012 |
| 71 | ABP98003.1 | immunoglobulin heavy chain variable region [Homo sapiens] | 41.8 | 41.8 | 100% | 0.012 |

TABLE 2-continued

Sequences producing significant alignments with PeptideX2

| SEQ ID NO: | Accession | Description | Max score | Total score | Query coverage | E value |
|---|---|---|---|---|---|---|
| 72 | ABP97942.1 | immunoglobulin heavy chain variable region [Homo sapiens] | 41.8 | 41.8 | 100% | 0.012 |
| 73 | ABP97768.1 | immunoglobulin heavy chain variable region [Homo sapiens] | 41.8 | 41.8 | 100% | 0.012 |
| 74 | ABP97575.1 | immunoglobulin heavy chain variable region [Homo sapiens] | 41.8 | 41.8 | 100% | 0.012 |
| 75 | ABP97570.1 | immunoglobulin heavy chain variable region [Homo sapiens] | 41.8 | 41.8 | 100% | 0.012 |
| 76 | ABV70953.1 | immunoglobulin heavy chain variable region [Homo sapiens] | 41.8 | 41.8 | 100% | 0.012 |
| 77 | ABM67236.1 | immunoglobulin heavy chain variable region [Homo sapiens] | 41.8 | 41.8 | 100% | 0.012 |
| 78 | CAK50728.1 | immunoglobulin A heavy chain variable region [Homo sapiens] | 41.8 | 41.8 | 100% | 0.012 |
| 79 | ABI35565.1 | immunoglobulin heavy chain variable region [Homo sapiens] | 41.8 | 41.8 | 100% | 0.012 |
| 80 | ABM53261.1 | immunoglobulin heavy chain variable region [Homo sapiens] | 41.8 | 41.8 | 100% | 0.012 |
| 81 | EAW82007.1 | hCG2029223 [Homo sapiens] | 41.8 | 41.8 | 100% | 0.012 |
| 82 | ABK81362.1 | immunoglobulin heavy chain variable region [Homo sapiens] | 41.8 | 41.8 | 100% | 0.012 |
| 83 | ABK81417.1 | immunoglobulin heavy chain variable region [Homo sapiens] | 41.8 | 41.8 | 100% | 0.012 |
| 84 | ABJ97553.1 | immunoglobulin heavy chain variable region [Homo sapiens] | 41.8 | 41.8 | 100% | 0.012 |
| 85 | ABI74220.1 | immunoglobulin heavy chain variable region [Homo sapiens] >gb\|ABI74221.1\| immunoglobulin heavy chain variable region [Homo sapiens] | 41.8 | 41.8 | 100% | 0.012 |
| 86 | ABI74341.1 | immunoglobulin heavy chain variable region [Homo sapiens] | 41.8 | 41.8 | 100% | 0.012 |
| 87 | ABI74230.1 | immunoglobulin heavy chain variable region [Homo sapiens] | 41.8 | 41.8 | 100% | 0.012 |
| 88 | ABG38442.1 | immunglobulin heavy chain variable region [Homo sapiens] | 41.8 | 41.8 | 100% | 0.012 |
| 89 | AAS85995.1 | immunoglobulin heavy chain [Homo sapiens] | 41.8 | 41.8 | 100% | 0.012 |
| 90 | AAS86095.1 | immunoglobulin heavy chain [Homo sapiens] | 41.8 | 41.8 | 100% | 0.012 |
| 91 | AAQ87970.1 | immunoglobulin E heavy chain variable region [Homo sapiens] | 41.8 | 41.8 | 100% | 0.012 |
| 92 | CAE45439.1 | immunoglobulin heavy chain variable region [Homo sapiens] | 41.8 | 41.8 | 100% | 0.012 |
| 93 | CAC10788.1 | immunoglobulin heavy chain variable region [Homo sapiens] | 41.8 | 41.8 | 100% | 0.012 |
| 94 | CAD19295.1 | immunoglobulin heavy chain variable region [Homo sapiens] | 41.8 | 41.8 | 100% | 0.012 |
| 95 | CAD44709.1 | immunoglobulin heavy chain variable region [Homo sapiens] | 41.8 | 41.8 | 100% | 0.012 |
| 96 | CAA12632.1 | Ig heavy chain variable region [Homo sapiens] | 41.8 | 41.8 | 100% | 0.012 |
| 97 | CAD60291.1 | immunoglobulin heavy chain variable region [Homo sapiens] | 41.8 | 41.8 | 100% | 0.012 |
| 98 | CAC94369.1 | immunoglobulin heavy chain variable region [Homo sapiens] | 41.8 | 41.8 | 100% | 0.012 |
| 99 | CAD60306.1 | immunoglobulin heavy chain variable region [Homo sapiens] | 41.8 | 41.8 | 100% | 0.012 |
| 100 | BAC02049.1 | immunoglobulin heavy chain VHDJ region [Homo sapiens] | 41.8 | 41.8 | 100% | 0.012 |
| 101 | BAC02301.1 | immunoglobulin heavy chain VHDJ region [Homo sapiens] | 41.8 | 41.8 | 100% | 0.012 |
| 102 | CAC10773.1 | immunoglobulin heavy chain VHDJ region [Homo sapiens] | 41.8 | 41.8 | 100% | 0.012 |
| 103 | BAC02007.1 | immunoglobulin heavy chain VHDJ region [Homo sapiens] | 41.8 | 41.8 | 100% | 0.012 |
| 104 | CAD60290.1 | immunoglobulin heavy chain variable region [Homo sapiens] | 41.8 | 41.8 | 100% | 0.012 |

Example 5

PeptideX2 Inhibited the Growth of E. coli

The results demonstrated in the previous Examples suggested that neutrophils may play a significant role in fetal-maternal allograft acceptance, and that IgX may be a significant immunomodulating molecule that exerted its immunomodulatory effect through the presence within the IgX heavy chain Vh domain of the PeptideX2 structure. To test this hypothesis, human peripheral white cells were incubated with E. coli in the presence and absence of PeptideX2.

Figure 11:
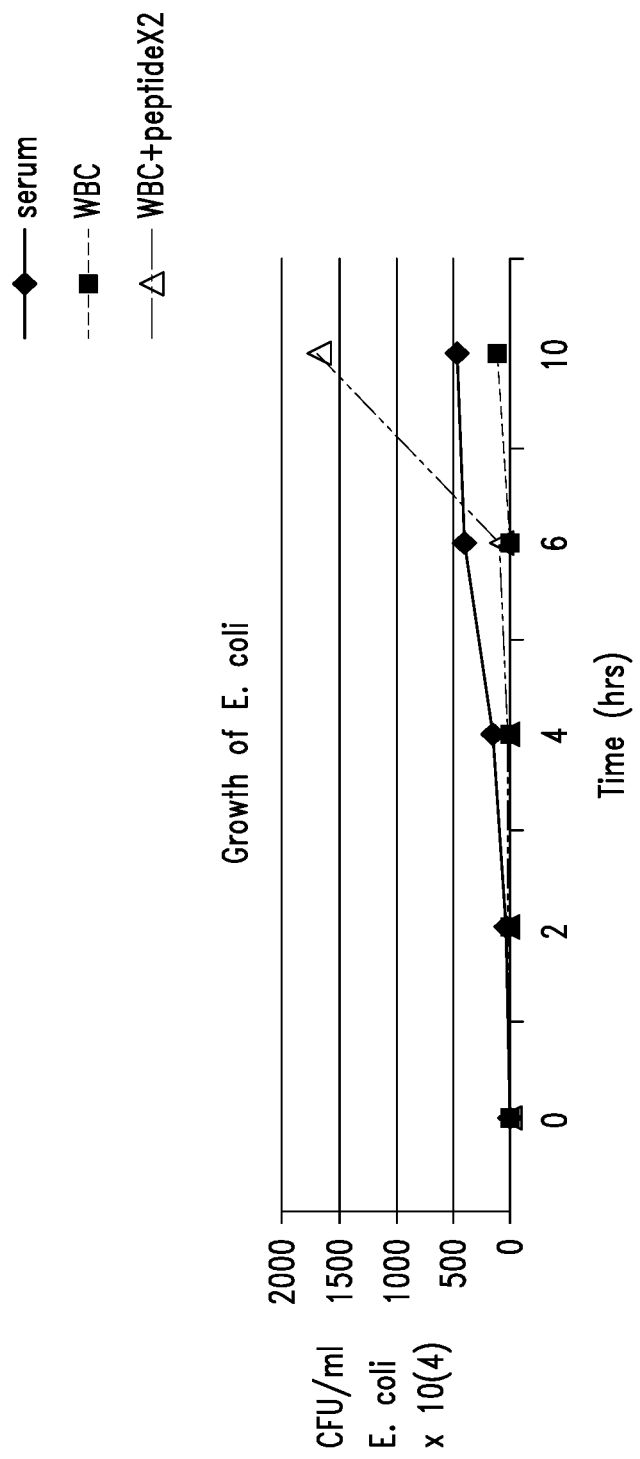
FIG. 11 is a bar graph that shows CFUs of E. coli incubated with serum, peripheral blood leukocytes or peripheral blood leukocytes in combination with PeptideX2 for 10 hours.
Figure 12:
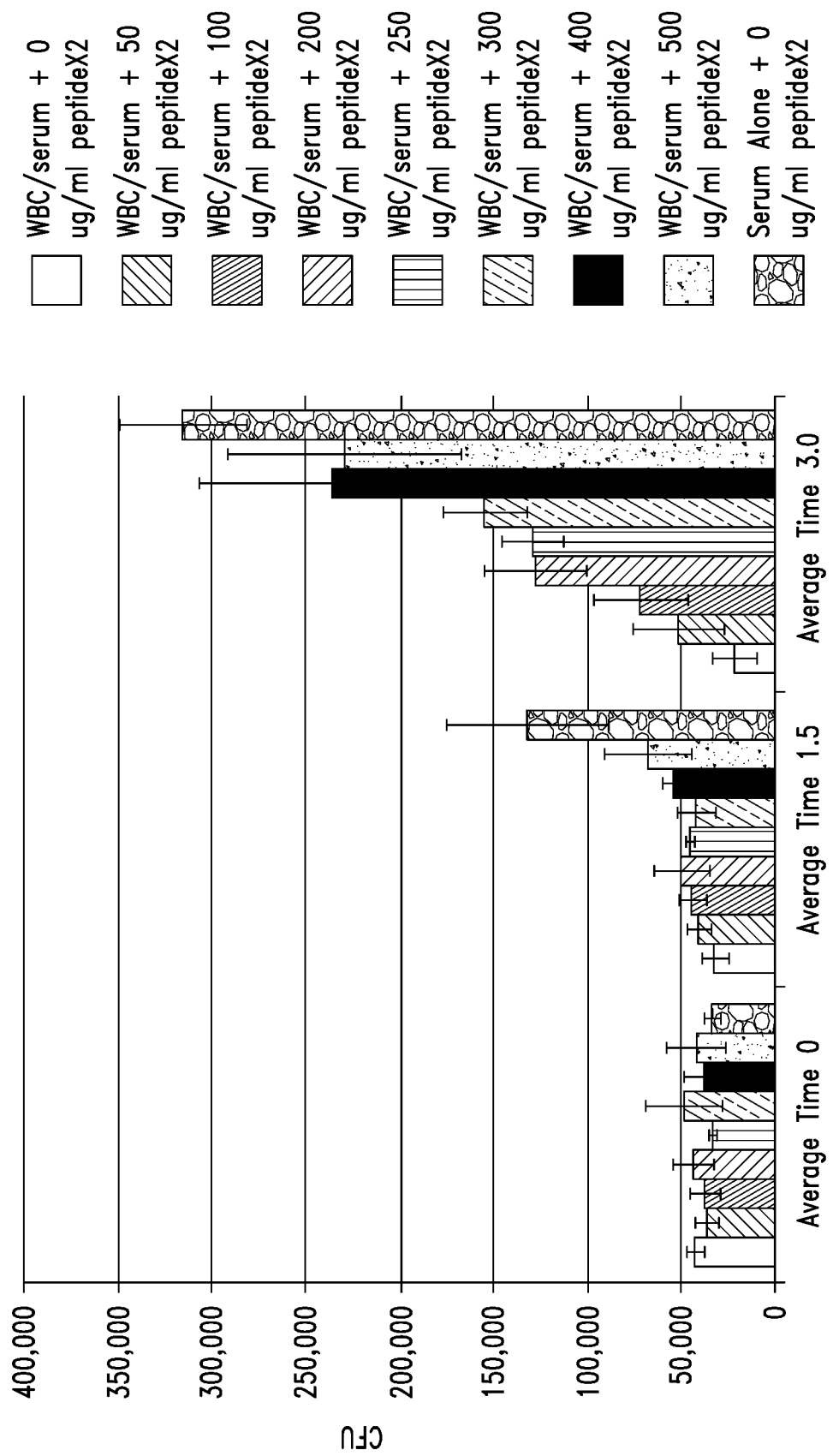
FIG. 12 is a bar graph that shows CFUs of E. coli incubated with serum, peripheral blood leukocytes or peripheral blood leukocytes in combination with various concentrations of PeptideX2 at several time points.

Human peripheral blood leukocytes (WBCs) were obtained from healthy donors with informed consent. Three test groups were inoculated with E. coli and incubated for 10 hours. The three groups were E. coli with serum alone, E. coli with WBCs, and E. coli with WBCs with PeptideX2. Samples were taken at 0, 2, 4, 6 and 10 hours and plated for colony forming units (CFUs). The number of E. coli present in the serum increased modestly over time, while the number of E. coli present in the WBC group showed only a slight increase. In contrast, the E. coli present in the WBC experimental group that was incubated with PeptideX2 group exhibited a rapid rise in CFUs at 10 hours (FIG. 11). In a separate but similar experiment, nine test groups (E. coli with serum alone, E. coli with WBCs, and E. coli with WBCs with PeptideX2 at each of seven indicated concentrations, see FIG. 12) were incubated over a time course of three hours, with quantification of bacterial CFU performed at times 0, 1.5 and 3 hours (FIG. 12). These results suggested that PeptideX2 suppressed the innate immune response that was mediated by WBC in the absence of PeptideX2, and that PeptideX2 may down regulate the adaptive immune response.

Example 6

Amino Acid Sequence Alignment of PeptideX2 Against PIF Peptides

Pre-implantation Factor (PIF) peptides are naturally occurring peptides that have been shown to promote suppression of the maternal immune response during pregnancy and may be important for embryo implantation. Several PIF peptides have been identified (see, e.g., PCT Application Publication Nos. WO 2003/004601 and WO 2005/040196). In order to confirm that PeptideX2 was not a known PIF peptide, the amino acid sequences of 8 PIF peptides (sequences 1-8 in Table 3) were compared to the amino acid sequence of PeptideX2. As shown in Table 3 below, none of the PIF sequences share any sequence identity with PeptideX2.

TABLE 3

PIF and PeptideX2 amino acid sequence comparison

| Sequence | Amino acid residues |   |   |   |   |   |   |   |
|---|---|---|---|---|---|---|---|---|
| sequence #1 | G | K | R | I | K | G | T |   |
| sequence #2 | V | L | G | K | R | I | K | G | T |

TABLE 3-continued

PIF and PeptideX2 amino acid sequence comparison

| Sequence | Amino acid residues | | | | | | | | | | |
|---|---|---|---|---|---|---|---|---|---|---|---|
| sequence #3 | I | E | V | L | G | K | R | I | K | G | T |
| sequence #4 | I | D | V | L | G | K | R | I | K | G | T |
| sequence #5 | I | R | V | L | G | K | R | I | K | G | T |
| sequence #6 | I | E | V | T | G | K | R | I | K | G | T |
| sequence #7 | I | D | V | T | G | K | R | I | K | G | T |
| sequence #8 | I | R | V | T | G | K | R | I | K | G | T |
| peptideX2 | K | S | I | A | Y | L | Q | M | N | S | L | K |
| HOMOLOGY | no | no | no | no | no | no | no | no | no | no | no |

Example 7

In Vitro Allograft Cell Proliferation Assays with PeptideX2

A modified mixed lymphocyte reaction (MMLR) is used to determine if the immunomodulating properties of PeptideX2 are sufficient to suppress cell proliferation in an in vitro allograft model. Mixed lymphocyte reactions are used to test the compatibility of lymphocytes from two individuals. One set of lymphocytes is irradiated or treated with mitomycin C so that they cannot respond or proliferate in response to a stimulus, and the other set of lymphocytes are responder cells which can differentiate into effector cells and proliferate if they are alloreactive to the first set of lymphocytes. The MMLR includes test groups featuring the addition of PeptideX2 to determine its suppressive effect on cell proliferation.

Cultures of peripheral white blood cells of eight human subjects obtained with appropriate informed consent are analyzed using one-way and two-way MMLR. Cells are cultured with 250 ug/ml PeptideX2 in one-way reactions using mitomicyin C. Two-way MMLR are also performed using 250 ug/ml PeptideX2. Cell proliferation is measured using a BrdU colorimetric assay according to the manufacturer's instructions (Roche Applied Science Product #11647229001). Inhibition of cellular proliferation by at least 50% indicates that a concentration of PeptideX2 is sufficient to suppress cell proliferation.

Optimum dosing of PeptideX2 is determined by measuring the degree of inhibition of cellular proliferation using various concentrations of PeptideX2. The concentrations include 25, 50, 100, 250 and 500 μg/ml. The dose of PeptideX2 that results in the greatest alteration (e.g., statistically significant decrease in cytoproliferation) in MMLR assays is regarded as the optimum dose for suppressing cellular proliferation.

Example 8

In Vitro Xenograft Cell Proliferation Assays with PeptideX2

Similarly, MMLR assays are used to determine if PeptideX2 may be useful in suppressing cellular proliferation as an in vitro xenograft model. The MMLR assays are performed as described above, however, mixtures of human and non-human leukocytes are used to determine the optimum dose or concentration of PeptideX2 for suppressing cellular proliferation in a xenograft model. The non-human leukocytes are obtained from pigs, rats and monkeys.

Example 9

Generation of PeptideX2 Variants

Variants of PeptideX2 are generated by introducing amino acid substitutions at different positions in the PeptideX2 amino acid sequence in order to determine if such variations enhance the biological activity of PeptideX2. Preferred variants are polypeptides of 12, 13, 14, 15, 16, 17, 18, 19, 20, 21, 22, 23, 24, 25, 26, 27, 28, 29, 30 or 31 amino acids that comprise at least one amino acid sequence as set forth in SEQ ID NO:106; in embodiments where the peptide comprises a polypeptide of SEQ ID NO:106 that differs in amino acid sequence from SEQ ID NO:2, polypeptides of no more than 12, 13, 14, 15, 16, 17, 18, 19, 20, 21, 22, 23, 24, 25, 26, 27, 28, 29, 30 or 31 amino acids, or of no more than 32, 33, 34, 35, 36, 37, 38, 39, 40, 41, 42, 43, 44, 45, 46, 47, 48, 49, 50, 51, 52, 53, 54, 55, 56, 57, 58, 59, 60, 61-70, 71-80 or 81-90 amino acids may be used. The modified peptides are tested as candidate competitive inhibitors of PeptideX2-FITC (described above) binding to neutrophils, using flow cytometry in order to compare their activity. Competitive cell-binding assays are performed by flow cytometry as described above, and cytokine induction profiles are also generated as described above, in order to compare the modified PeptideX2 sequences with unmodified PeptideX2. Peptides exhibiting significant activity are selected for use in MMLR and in vivo transplant models having relevance to organ transplantation and allograft rejection as discussed herein.

In flow cytometry-based competitive binding assays, cells are incubated with either PeptideX2-FITC or PeptideX2-FITC conjugated to BSA and the PeptideX2 sequence variant, to determine if the variant competes with PeptideX2. The competitive binding assays are used in addition to the cytokine profile results in order to determine candidate PeptideX2 variants for use in medical treatments such as transplantation.

Example 10

In Vivo Transplant Model

In order to further examine the potential role of PeptideX2, or a suitable variant, established in vivo allograft and xenograft models are utilized. For a xenograft model, human tissue is transplanted into an animal, such as a rodent or primate. Control animals are not treated with PeptideX2, and test animals are treated with either PeptideX2 or a standard immunosuppressive agent, such as anti-IL-2Rα. The rate of graft acceptance and/or rejection between the treatment groups is compared.

Example 11

Immune Status Profile of PeptideX2-Induced Immunomodulation

Immune status profiling is performed by determining the effects, on peripheral blood white blood cells, of exposure to a herein provided polypeptide that comprises the PeptideX2 sequence (SEQ ID NO:2) or that comprises the PeptideX2 variant sequence (SEQ ID NO:106) as described herein. MLR and MMLR assays are performed as described above, and the effects of PeptideX2 (SEQ ID NO:2) sequence-containing polypeptides or PeptideX2 variant (SEQ ID NO:106) sequence-containing polypeptides on MLR and MMLR are determined by measuring cellular proliferation and also by characterizing supernatant fluids for released cytokines using art accepted assay methodologies (e.g., with immunoassay kits as are readily available from R & D Systems, Minneapolis, Minn., or from BD Biosciences, San Jose, Calif.; or using other well known methodologies for detecting and quantifying cytokines). The effects of PeptideX2 or PeptideX2 variant sequence-containing polypeptides are also assessed on in vitro peripheral blood leukocyte (PBL) cultures following stimulation with T cell mitogens (e.g., PHA, or costimulatory antibody combinations such as anti-CD3/anti-CD28, etc.) or with B cell mitogens (e.g., LPS, or costimulatory antibody combinations, etc.) or with other established PBL subpopulation-specific or non-specific stimulatory protocols.

Following in vitro stimulation in controlled experimental groups that include such treatments in the presence and absence of a PeptideX2 or PeptideX2 variant sequence-containing polypeptide as provided herein, culture fluids are separated from cells and tested for the presence of one or more members of a panel of immunologically relevant cytokines. The panel includes: IL-2, IL-4, IL-6, IL-8, IL-10, IL-12, and TNF-α (detection of these cytokines is also described above) and also includes one or more of IL-1β, IL-5, IL-8, IL-13, IL-17, IL-22, CCL2, CCL3, CCL4, CCL5, CCL11, CXCL5, CXCL11, TGF13, IFNγ, basic FGF, GCSF, GMCSF, VEGF, EGF, and HGF.

Peripheral blood white cells containing peripheral blood leukocytes are also sorted using fluorescence activated cell sorting (FACS) on the basis of positive staining with labeled PeptideX2 or IgX, and the positively selected cells are cultured in culture medium alone or in medium supplemented with PeptideX2, IgX and/or other neutrophil-inducing agents. At suitable timepoints medium aliquots are collected and separated from cells, and the supernatant fluids are tested for the presence of one or more of the members of the panel of cytokines as described above, in order to profile the cytokine-elaboration activity status of PeptideX2-expressing cells.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of selectively labeling a mammalian peripheral blood white cell neutrophil subpopulation, comprising contacting a population of mammalian peripheral blood white cells which comprises neutrophils with an immunomodulatory polypeptide of no more than 31, 30, 29, 28, 27, 26, 25, 24, 23, 22, 21, 20, 19, 18, 17, 16, 15, 14, 13 or 12 amino acids which comprises the amino acid sequence set forth in SEQ ID NO:2, wherein the immunomodulatory polypeptide comprises a detectable label.

2. The method of claim 1, wherein the detectable label is selected from the group consisting of a fluorescent dye, a radioactive substance and a metal particle.

* * * * *

SEQUENCE LISTING

```
<160> NUMBER OF SEQ ID NOS: 115

<210> SEQ ID NO 1
<211> LENGTH: 11
<212> TYPE: PRT
<213> ORGANISM: Artificial Sequence
<220> FEATURE:
<223> OTHER INFORMATION: Peptide fragment

<400> SEQUENCE: 1

Ala Glu Asp Thr Ala Val Tyr Tyr Cys Ala Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Peptide fragment

<400> SEQUENCE: 2

Lys Ser Ile Ala Tyr Leu Gln Met Asn Ser Leu Lys
1               5                   10

<210> SEQ ID NO 3
<211> LENGTH: 471
<212> TYPE: PRT
<213> ORGANISM: Homo sapiens

<400> SEQUENCE: 3

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
                20                  25                  30
```

-continued

```
Pro Gly Arg Ser Leu Arg Leu Ser Cys Thr Ser Ser Gly Phe Thr Phe
         35                  40                  45
Gly Asp Tyr Ala Met Asn Trp Val Arg Gln Ala Pro Gly Lys Gly Leu
 50                  55                  60
Glu Trp Val Gly Phe Ile Arg Ser Lys Pro Tyr Gly Gly Thr Thr Glu
 65                  70                  75                  80
Tyr Ala Ala Ser Leu Lys Gly Arg Phe Thr Val Ser Arg Asp Asp Ser
                 85                  90                  95
Lys Ser Ile Ala Tyr Leu Gln Met Asn Ser Leu Lys Thr Glu Asp Thr
                100                 105                 110
Ala Leu Tyr Tyr Cys Thr Arg Ser Leu Arg Gly Val Gln Gly Pro Leu
            115                 120                 125
Asp Tyr Trp Gly Gln Gly Thr Leu Val Thr Val Ser Ser Ala Ser Thr
130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
            210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
            355                 360                 365
Glu Pro Gln Val Tyr Thr Leu Pro Pro Ser Arg Asp Glu Leu Thr Lys
370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
            435                 440                 445
Cys Ser Val Met His Glu Ala Leu His Asn His Tyr Thr Gln Lys Ser
```

```
                450                 455                 460

Leu Ser Leu Ser Pro Gly Lys
465                 470

<210> SEQ ID NO 4
<211> LENGTH: 23
<212> TYPE: PRT
<213> ORGANISM: Artificial Sequence
<220> FEATURE:
<223> OTHER INFORMATION: Peptide fragment

<400> SEQUENCE: 4

Lys Ser Ile Ala Tyr Leu Gln Met Asn Ser Leu Lys Thr Glu Asp Thr
1               5                   10                  15

Ala Leu Tyr Tyr Cys Thr Arg
            20

<210> SEQ ID NO 5
<211> LENGTH: 126
<212> TYPE: PRT
<213> ORGANISM: Homo sapiens

<400> SEQUENCE: 5

Leu Leu Glu Ser Gly Glu Gly Leu Val Gln Pro Gly Arg Ser Leu Arg
1               5                   10                  15

Leu Ser Cys Thr Ala Ser Gly Phe Thr Phe Gly Asp Tyr Ala Met Ser
            20                  25                  30

Trp Phe Arg Gln Ala Ser Gly Lys Gly Leu Glu Trp Val Gly Phe Ile
        35                  40                  45

Arg Ser Glu Ala Tyr Gly Gly Thr Thr Glu Tyr Ala Ala Ser Val Lys
    50                  55                  60

Gly Arg Phe Thr Ile Ser Arg Asp Asp Ser Lys Ser Ile Ala Tyr Leu
65                  70                  75                  80

Gln Met Asn Ser Leu Lys Thr Glu Asp Thr Ala Val Tyr Tyr Cys Thr
                85                  90                  95

Arg Glu Glu Trp Gly Ser Gly Trp Asn Gly Tyr Tyr Phe Asp Tyr Trp
            100                 105                 110

Gly Gln Gly Thr Leu Val Thr Val Ser Ser Ala Ser Thr Ala
        115                 120                 125

<210> SEQ ID NO 6
<211> LENGTH: 123
<212> TYPE: PRT
<213> ORGANISM: Homo sapiens

<400> SEQUENCE: 6

Glu Val Gln Leu Leu Glu Ser Gly Gly Leu Val Gln Pro Gly Arg
1               5                   10                  15

Ser Leu Arg Leu Ser Cys Thr Pro Ser Gly Phe Thr Phe Gly Asp Tyr
            20                  25                  30

Ala Met Ser Trp Ile Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95
```

Tyr Cys Thr Arg Trp Gly Ser Gly Ser Thr Asp Ala Phe Asp Ile
            100                 105                 110

Trp Gly Gln Gly Thr Met Val Thr Val Ser Ser
        115                 120

<210> SEQ ID NO 7
<211> LENGTH: 125
<212> TYPE: PRT
<213> ORGANISM: Homo sapiens

<400> SEQUENCE: 7

Glu Val Gln Leu Leu Glu Ser Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Gly Asp Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Glu Cys Gly Asp Pro Leu Leu Tyr Tyr Phe Phe Ala Met
            100                 105                 110

Asp Val Trp Gly Gln Gly Thr Met Val Thr Val Ser Ser
        115                 120                 125

<210> SEQ ID NO 8
<211> LENGTH: 114
<212> TYPE: PRT
<213> ORGANISM: Homo sapiens

<400> SEQUENCE: 8

Gly Gly Leu Val Gln Pro Gly Arg Ser Leu Thr Leu Ser Cys Ser Val
1               5                   10                  15

Ser Gly Phe Thr Phe Gly Asp Tyr Ala Met Ser Trp Val Arg Gln Ala
            20                  25                  30

Pro Gly Lys Gly Leu Glu Trp Val Gly Leu Ile Arg Ser Lys Thr Tyr
        35                  40                  45

Arg Gly Thr Thr Asp Tyr Ala Ala Ser Val Lys Gly Arg Val Thr Ile
    50                  55                  60

Ser Arg Asp Asp Ser Lys Ser Ile Ala Tyr Leu Gln Met Asn Ser Leu
65                  70                  75                  80

Lys Ile Asp Asp Thr Ala Val Tyr Tyr Cys Gly Arg Thr Leu Gly Ser
                85                  90                  95

Gly Asn Ala Ile Ser Tyr Tyr Tyr Gly Met Asp Val Trp Gly Leu Gly
            100                 105                 110

Thr Thr

<210> SEQ ID NO 9
<211> LENGTH: 116
<212> TYPE: PRT
<213> ORGANISM: Homo sapiens

<400> SEQUENCE: 9

Gly Gly Leu Val Gln Pro Gly Arg Ser Leu Arg Leu Ser Cys Thr Ala
1               5                   10                  15

Ser Gly Phe Thr Phe Gly Asp Phe Val Met Ser Trp Phe Arg Gln Ala
            20                  25                  30

Pro Gly Arg Gly Leu Glu Trp Val Gly Leu Ile Arg Asn Lys Ala Tyr
            35                  40                  45

Gly Gly Thr Thr Glu Tyr Ala Ala Ser Val Lys Gly Arg Phe Thr Ile
50                  55                  60

Ser Arg Glu Asp Ser Lys Ser Ile Ala Tyr Leu Gln Met Asn Ser Leu
65                  70                  75                  80

Lys Thr Asp Asp Ala Ala Val Tyr Tyr Cys Thr Arg Asp Lys Val Val
                85                  90                  95

Gly Ala Thr Met Asp Tyr His Tyr Tyr Gly Met Asp Val Trp Gly
                100                 105                 110

Gln Gly Thr Thr
        115

<210> SEQ ID NO 10
<211> LENGTH: 140
<212> TYPE: PRT
<213> ORGANISM: Homo sapiens

<400> SEQUENCE: 10

Val Gln Leu Val Glu Ser Gly Gly Gly Leu Val Gln Pro Gly Arg Ser
1               5                   10                  15

Leu Arg Leu Ser Cys Thr Ala Ser Gly Phe Thr Phe Gly Asp Tyr Ala
            20                  25                  30

Met Ser Trp Val Arg Gln Ala Pro Gly Lys Gly Leu Glu Trp Val Gly
            35                  40                  45

Phe Ile Arg Ser Lys Ala Tyr Gly Gly Thr Thr Glu Tyr Ala Ala Ser
        50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Thr Arg Pro Gly Tyr Ser Ser Gly Cys Gly Tyr Trp Gly Gln Gly
                100                 105                 110

Thr Leu Val Thr Val Ser Ser Gly Ser Ala Ser Ala Pro Thr Leu Phe
            115                 120                 125

Pro Ser Ser Pro Val Arg Ile Pro Arg Arg Ile Arg
        130                 135                 140

<210> SEQ ID NO 11
<211> LENGTH: 145
<212> TYPE: PRT
<213> ORGANISM: Homo sapiens
<220> FEATURE:
<221> NAME/KEY: VARIANT
<222> LOCATION: (1)...(145)
<223> OTHER INFORMATION: Xaa = Any Amino Acid

<400> SEQUENCE: 11

Gly Val Gln Cys Glu Val Gln Leu Val Glu Ser Gly Gly Gly Leu Val
1               5                   10                  15

Gln Pro Gly Arg Ser Leu Arg Leu Ser Cys Thr Ala Ser Gly Phe Thr
            20                  25                  30

Phe Gly Asp Tyr Ala Met Ser Trp Val Arg Gln Ala Pro Gly Lys Gly
            35                  40                  45

Leu Glu Trp Val Gly Phe Ile Arg Ser Lys Ala Tyr Gly Gly Thr Thr

```
            50                  55                  60
Glu Tyr Ala Ala Ser Val Lys Gly Arg Phe Thr Ile Ser Arg Asp Asp
 65                  70                  75                  80

Ser Lys Ser Ile Ala Tyr Leu Gln Met Asn Ser Leu Lys Thr Glu Asp
                     85                  90                  95

Thr Ala Val Tyr Tyr Cys Thr Arg Asp Gln Glu Gln Trp Leu Val Pro
                100                 105                 110

Gln Phe Asp Tyr Trp Gly Gln Gly Thr Leu Val Thr Val Ser Ser Gly
            115                 120                 125

Ser Ala Ser Pro Gln Pro Phe Ser Pro Arg Leu Leu Xaa Lys Phe Pro
            130                 135                 140

Val
145

<210> SEQ ID NO 12
<211> LENGTH: 144
<212> TYPE: PRT
<213> ORGANISM: Homo sapiens

<400> SEQUENCE: 12

Lys Val Pro Val Glu Val Gln Leu Val Glu Ser Gly Gly Asp Leu Leu
 1                   5                  10                  15

Gln Pro Gly Arg Ser Leu Arg Leu Ser Cys Thr Ala Ser Gly Phe Thr
                 20                  25                  30

Phe Gly Asp Tyr Thr Met Asn Trp Val Arg Gln Ala Pro Gly Lys Gly
             35                  40                  45

Leu Glu Trp Val Gly Phe Val Arg Lys Gln Glu Tyr Gly Gly Thr Thr
 50                  55                  60

Glu Tyr Ala Ala Ser Val Arg Gly Arg Val Thr Ile Ser Arg Asp Asp
 65                  70                  75                  80

Ser Lys Ser Ile Ala Tyr Leu Gln Met Asn Ser Leu Lys Ser Asp Asp
                     85                  90                  95

Thr Ala Val Tyr Tyr Cys Thr Gly Glu Leu Asp Leu Gly Ala Thr Tyr
                100                 105                 110

Tyr Tyr Tyr Gly Met Asp Val Trp Gly Gln Gly Thr Thr Val Thr Val
            115                 120                 125

Ser Ser Ala Ser Thr Lys Gly Pro Ser Val Phe Pro Leu Ala Pro Ser
            130                 135                 140

<210> SEQ ID NO 13
<211> LENGTH: 144
<212> TYPE: PRT
<213> ORGANISM: Homo sapiens

<400> SEQUENCE: 13

Arg Cys Pro Val Glu Val Gln Leu Val Glu Ser Gly Gly Asp Leu Leu
 1                   5                  10                  15

Gln Pro Gly Arg Ser Leu Arg Leu Ser Cys Thr Ala Ser Gly Phe Thr
                 20                  25                  30

Phe Gly Asp Tyr Thr Met Asn Trp Val Arg Gln Ala Pro Gly Lys Gly
             35                  40                  45

Leu Glu Trp Val Gly Phe Val Arg Lys Gln Glu Tyr Gly Gly Thr Thr
 50                  55                  60

Glu Tyr Ala Ala Ser Val Arg Gly Arg Val Thr Ile Ser Arg Asp Asp
 65                  70                  75                  80

Ser Lys Ser Ile Ala Tyr Leu Gln Met Asn Ser Leu Lys Ser Asp Asp
```

```
                     85                  90                  95

Thr Ala Val Tyr Tyr Cys Thr Gly Glu Leu Asp Leu Gly Ala Thr Tyr
                100                 105                 110

Tyr Tyr Tyr Gly Met Asp Val Trp Gly Gln Gly Thr Thr Val Thr Val
                115                 120                 125

Ser Ser Ala Ser Thr Lys Gly Pro Ser Val Phe Pro Leu Ala Pro Ser
                130                 135                 140

<210> SEQ ID NO 14
<211> LENGTH: 144
<212> TYPE: PRT
<213> ORGANISM: Homo sapiens

<400> SEQUENCE: 14

Arg Cys Pro Val Glu Val Gln Leu Val Glu Ser Gly Gly Asp Leu Leu
1               5                   10                  15

Gln Pro Gly Arg Ser Leu Arg Leu Ser Cys Thr Ala Ser Gly Phe Thr
                20                  25                  30

Phe Gly Asp Tyr Thr Met Asn Trp Val Arg Gln Ala Pro Gly Lys Gly
                35                  40                  45

Leu Glu Trp Val Gly Phe Val Arg Lys Gln Glu Tyr Gly Gly Thr Thr
    50                  55                  60

Glu Tyr Ala Ala Ser Val Arg Gly Arg Val Thr Ile Ser Arg Asp Asp
65                  70                  75                  80

Ser Lys Ser Ile Ala Tyr Leu Gln Met Asn Ser Leu Lys Ser Gly Asp
                85                  90                  95

Thr Ala Val Tyr Tyr Cys Thr Gly Glu Leu Asp Leu Gly Ala Thr Tyr
                100                 105                 110

Tyr Tyr Tyr Gly Met Asp Val Trp Gly Gln Gly Thr Thr Val Thr Val
                115                 120                 125

Ser Ser Ala Ser Thr Lys Gly Pro Ser Val Phe Pro Leu Ala Pro Ser
                130                 135                 140

<210> SEQ ID NO 15
<211> LENGTH: 143
<212> TYPE: PRT
<213> ORGANISM: Homo sapiens

<400> SEQUENCE: 15

Cys Pro Val Glu Val Gln Leu Val Glu Ser Gly Gly Asp Leu Leu Gln
1               5                   10                  15

Pro Gly Arg Ser Leu Arg Leu Ser Cys Thr Ala Ser Gly Phe Thr Phe
                20                  25                  30

Gly Asp Tyr Thr Met Asn Trp Val Arg Gln Ala Pro Gly Lys Gly Leu
                35                  40                  45

Glu Trp Val Gly Phe Val Arg Lys Gln Glu Tyr Gly Gly Thr Thr Glu
    50                  55                  60

Tyr Ala Ala Ser Val Arg Gly Arg Val Thr Ile Ser Arg Asp Asp Ser
65                  70                  75                  80

Lys Ser Ile Ala Tyr Leu Gln Met Asn Ser Leu Lys Ser Asp Asp Thr
                85                  90                  95

Ala Val Tyr Tyr Cys Thr Gly Glu Leu Asp Leu Gly Ala Thr Tyr Tyr
                100                 105                 110

Tyr Tyr Gly Met Asp Val Trp Gly Gln Gly Thr Thr Val Thr Val Ser
                115                 120                 125

Ser Ala Ser Thr Lys Gly Pro Ser Val Phe Pro Leu Ala Pro Ser
```

<210> SEQ ID NO 16
<211> LENGTH: 138
<212> TYPE: PRT
<213> ORGANISM: Homo sapiens

<400> SEQUENCE: 16

Val Gln Leu Val Glu Ser Gly Gly Asp Leu Leu Gln Pro Gly Arg Ser
1               5                   10                  15

Leu Arg Leu Ser Cys Thr Ala Ser Gly Phe Thr Phe Gly Asp Tyr Thr
            20                  25                  30

Met Asn Trp Val Arg Gln Ala Pro Gly Lys Gly Leu Glu Trp Val Gly
        35                  40                  45

Phe Val Arg Lys Gln Glu Tyr Gly Gly Thr Thr Glu Tyr Ala Ala Ser
    50                  55                  60

Val Arg Gly Arg Val Thr Ile Ser Arg Asp Asp Ser Lys Ser Ile Ala
65                  70                  75                  80

Tyr Leu Gln Met Asn Ser Leu Lys Ser Asp Asp Thr Ala Val Tyr Tyr
                85                  90                  95

Cys Thr Gly Glu Leu Asp Leu Gly Ala Thr Tyr Tyr Tyr Gly Met
            100                 105                 110

Asp Val Trp Gly Gln Gly Thr Thr Val Thr Val Ser Ala Ser Pro
        115                 120                 125

Arg Ala His Arg Ser Ser Pro Gly Ala Leu
        130                 135

<210> SEQ ID NO 17
<211> LENGTH: 139
<212> TYPE: PRT
<213> ORGANISM: Homo sapiens

<400> SEQUENCE: 17

Val Gln Leu Val Glu Ser Gly Gly Asp Leu Leu Gln Pro Gly Arg Ser
1               5                   10                  15

Leu Arg Leu Ser Cys Thr Ala Ser Gly Phe Thr Phe Gly Asp Tyr Thr
            20                  25                  30

Met Asn Trp Val Arg Gln Ala Pro Gly Lys Gly Leu Glu Trp Val Gly
        35                  40                  45

Phe Val Arg Lys Gln Glu Tyr Gly Gly Thr Thr Glu Tyr Ala Ala Ser
    50                  55                  60

Val Arg Gly Arg Val Thr Ile Ser Arg Asp Asp Ser Lys Ser Ile Ala
65                  70                  75                  80

Tyr Leu Gln Met Asn Ser Leu Lys Ser Asp Asp Thr Ala Val Tyr Tyr
                85                  90                  95

Cys Thr Gly Glu Leu Asp Leu Gly Ala Thr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser
        130                 135

<210> SEQ ID NO 18
<211> LENGTH: 120
<212> TYPE: PRT
<213> ORGANISM: Homo sapiens

<400> SEQUENCE: 18

Gln Val Gln Leu Val His Ser Gly Gly Leu Val Lys Pro Gly Arg
1               5                   10                  15

Ser Leu Arg Leu Ser Cys Thr Ala Ser Gly Phe Thr Phe Ser Asp Tyr
            20                  25                  30

Ala Val Ser Trp Phe Arg Gln Ala Pro Gly Lys Ala Pro Glu Trp Val
            35                  40                  45

Gly Leu Ile Arg Ser Arg His Tyr Gly Ala Lys Thr Gln Phe Ala Ala
        50                  55                  60

Ser Val Gln Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Asn Thr Ser Ser Leu Ala Val Ala Gly Asn Trp Gly Gln
            100                 105                 110

Gly Thr Leu Val Thr Val Ser Ser
        115                 120

<210> SEQ ID NO 19
<211> LENGTH: 100
<212> TYPE: PRT
<213> ORGANISM: Homo sapiens

<400> SEQUENCE: 19

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
        50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 20
<211> LENGTH: 131
<212> TYPE: PRT
<213> ORGANISM: Homo sapiens

<400> SEQUENCE: 20

Gly Gly Leu Val Gln Pro Gly Arg Ser Leu Arg Leu Ser Cys Thr Ala
1               5                   10                  15

Ser Gly Phe Thr Phe Gly Asp Tyr Ala Met Ser Trp Val Arg Gln Ala
            20                  25                  30

Pro Gly Lys Gly Leu Glu Trp Val Gly Phe Ile Arg Ser Lys Pro Tyr
            35                  40                  45

Gly Gly Thr Thr Glu Tyr Ala Ala Ser Val Lys Gly Arg Phe Thr Ile
        50                  55                  60

Ser Arg Asp Asp Ser Lys Ser Ile Ala Tyr Leu Gln Met Asn Ser Leu
65                  70                  75                  80

Lys Thr Glu Asp Thr Ala Val Tyr Tyr Cys Thr Arg Val Ser Pro Glu
                85                  90                  95

Gly Gly Leu Val His Phe Trp Tyr Phe Asp Leu Trp Gly Arg Gly Thr
              100                 105                 110

Leu Val Thr Val Ser Ser Ala Ser Thr Lys Gly Pro Ser Val Phe Pro
        115                 120                 125

Leu Ala Pro
     130

<210> SEQ ID NO 21
<211> LENGTH: 128
<212> TYPE: PRT
<213> ORGANISM: Homo sapiens

<400> SEQUENCE: 21

Gly Leu Val Lys Pro Gly Arg Ser Gln Arg Leu Ser Cys Ile Ala Ser
1               5                   10                  15

Gly Phe Thr Phe Gly Asp Tyr Ala Met Ser Trp Phe Arg Gln Ala Pro
            20                  25                  30

Gly Lys Gly Leu Glu Trp Val Gly Phe Ile Arg Gly Lys Ala Tyr Gly
        35                  40                  45

Gly Thr Thr Glu Tyr Ala Ala Ser Val Lys Gly Arg Phe Thr Ile Ser
    50                  55                  60

Arg Asp Asp Ser Lys Ser Ile Ala Tyr Leu Gln Met Asn Ser Leu Lys
65                  70                  75                  80

Thr Glu Asp Thr Ala Val Tyr Tyr Cys Thr Arg Thr Gln Glu Trp Arg
                85                  90                  95

Glu Phe Arg Tyr Tyr Tyr Gly Ser Gly Ser Thr Pro Pro His Tyr Tyr
            100                 105                 110

Tyr Gly Met Asp Val Trp Gly Gln Gly Thr Thr Val Thr Val Ser Ser
        115                 120                 125

<210> SEQ ID NO 22
<211> LENGTH: 87
<212> TYPE: PRT
<213> ORGANISM: Homo sapiens

<400> SEQUENCE: 22

Asp Tyr Ala Met Ser Trp Phe Arg Gln Ala Pro Gly Lys Gly Leu Glu
1               5                   10                  15

Trp Val Gly Phe Ile Arg Ser Lys Ala Tyr Gly Gly Thr Thr Glu Tyr
            20                  25                  30

Ala Ala Ser Val Lys Gly Arg Phe Thr Ile Ser Arg Asp Asp Ser Lys
        35                  40                  45

Ser Ile Ala Tyr Leu Gln Met Asn Ser Leu Lys Thr Glu Asp Thr Ala
    50                  55                  60

Val Tyr Tyr Cys Thr Arg Ala Thr Phe Ser Phe Phe Asp Tyr Trp Gly
65                  70                  75                  80

Gln Gly Thr Leu Val Thr Val
                85

<210> SEQ ID NO 23
<211> LENGTH: 93
<212> TYPE: PRT
<213> ORGANISM: Homo sapiens

<400> SEQUENCE: 23

Tyr Ala Met Ser Trp Phe Arg Gln Ala Pro Gly Lys Gly Leu Glu Trp
1               5                   10                  15

```
Val Gly Phe Ile Arg Ser Lys Ala Tyr Gly Thr Thr Glu Tyr Ala
             20                  25                  30

Ala Ser Val Lys Gly Arg Phe Thr Ile Ser Arg Asp Asp Ser Lys Ser
         35                  40                  45

Ile Ala Tyr Leu Gln Met Asn Ser Leu Lys Thr Glu Asp Thr Ala Val
     50                  55                  60

Tyr Tyr Cys Thr Arg Thr Gly Tyr Tyr Asp Ser Ser Gly Tyr Phe
 65              70                  75                  80

Tyr Tyr Tyr Gly Met Asp Val Trp Gly Gln Gly Thr Leu
                 85                  90
```

<210> SEQ ID NO 24
<211> LENGTH: 115
<212> TYPE: PRT
<213> ORGANISM: Homo sapiens

<400> SEQUENCE: 24

```
Val Gln Leu Val Glu Ser Gly Gly Gly Leu Val Gln Pro Gly Arg Ser
 1               5                  10                  15

Leu Arg Leu Ser Cys Thr Thr Ser Gly Phe Thr Phe Gly Asp Tyr Gly
             20                  25                  30

Leu Ser Trp Val Arg Gln Ala Pro Gly Lys Gly Leu Glu Trp Val Gly
         35                  40                  45

Phe Ile Arg Arg Lys Val Tyr Gly Glu Thr Thr Glu Tyr Ala Ala Ser
     50                  55                  60

Val Lys Gly Arg Phe Thr Ile Ser Arg Asp Asp Ser Lys Ser Ile Ala
 65              70                  75                  80

Tyr Leu Gln Met Asn Ser Leu Lys Thr Glu Asp Thr Ala Val Tyr Tyr
                 85                  90                  95

Cys Thr Arg Asp Asp Phe Trp Ser Gly Tyr Ser Tyr Trp Gly
            100                 105                 110

Gln Gly Thr
        115
```

<210> SEQ ID NO 25
<211> LENGTH: 117
<212> TYPE: PRT
<213> ORGANISM: Homo sapiens

<400> SEQUENCE: 25

```
Val Gln Leu Val Glu Ser Gly Gly Gly Leu Val Gln Pro Gly Arg Ser
 1               5                  10                  15

Leu Arg Leu Ser Cys Thr Ala Ser Gly Phe Thr Phe Gly Asp Tyr Ala
             20                  25                  30

Met Ser Trp Val Arg Gln Ala Pro Gly Lys Gly Leu Glu Trp Val Gly
         35                  40                  45

Phe Ile Arg Ser Lys Ala Tyr Gly Gly Thr Thr Glu Tyr Ala Ala Ser
     50                  55                  60

Val Lys Gly Arg Phe Thr Ile Ser Arg Asp Asp Ser Lys Ser Ile Ala
 65              70                  75                  80

Tyr Leu Gln Met Asn Ser Leu Lys Thr Glu Asp Thr Ala Val Tyr Tyr
                 85                  90                  95

Cys Thr Arg Asp Trp Glu Ile Ala Ala Arg Pro Glu Ser Phe Asp Tyr
            100                 105                 110

Trp Gly Gln Gly Thr
        115
```

<210> SEQ ID NO 26
<211> LENGTH: 112
<212> TYPE: PRT
<213> ORGANISM: Homo sapiens

<400> SEQUENCE: 26

Val Gln Leu Val Glu Ser Gly Gly Gly Leu Val Lys Pro Gly Arg Ser
1               5                   10                  15

Leu Arg Leu Ser Cys Thr Ala Ser Gly Phe Thr Phe Gly Asp Tyr Ala
            20                  25                  30

Met Ser Trp Phe Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
    50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Thr Arg Val Asp Thr Ala Met Val Asp Tyr Trp Gly Gln Gly Thr
            100                 105                 110

<210> SEQ ID NO 27
<211> LENGTH: 113
<212> TYPE: PRT
<213> ORGANISM: Homo sapiens

<400> SEQUENCE: 27

Val Gln Leu Val Glu Ser Gly Gly Gly Leu Val Lys Pro Gly Arg Ser
1               5                   10                  15

Leu Arg Leu Ser Cys Thr Ala Ser Gly Phe Thr Phe Gly Asp Tyr Val
            20                  25                  30

Met Ser Trp Phe Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
    50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Thr Arg Asp Pro Val Val Gly Pro Phe Asp Tyr Trp Gly Gln Gly
            100                 105                 110

Thr

<210> SEQ ID NO 28
<211> LENGTH: 120
<212> TYPE: PRT
<213> ORGANISM: Homo sapiens

<400> SEQUENCE: 28

Val Gln Leu Val Glu Ser Gly Gly Gly Leu Val Lys Pro Gly Arg Ser
1               5                   10                  15

Leu Arg Leu Ser Cys Thr Ala Ser Gly Phe Thr Phe Gly Asp Tyr Ala
            20                  25                  30

Met Ser Trp Phe Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
    50                  55                  60

```
Val Lys Gly Arg Phe Thr Ile Ser Arg Asp Asp Ser Lys Ser Ile Ala
 65                  70                  75                  80

Tyr Leu Gln Met Asn Ser Leu Lys Thr Glu Asp Thr Ala Val Tyr Tyr
                 85                  90                  95

Cys Thr Arg Asp Arg Asp Tyr Asp Ile Leu Thr Gly Tyr Tyr Trp Ser
            100                 105                 110

Asp Tyr Gly Met Asp Val Trp Gly
        115                 120

<210> SEQ ID NO 29
<211> LENGTH: 114
<212> TYPE: PRT
<213> ORGANISM: Homo sapiens

<400> SEQUENCE: 29

Val Gln Leu Val Glu Ser Gly Gly Gly Leu Val Lys Pro Gly Arg Ser
 1               5                  10                  15

Leu Arg Leu Ser Cys Thr Ala Ser Gly Phe Thr Phe Gly Asp Tyr Ala
            20                  25                  30

Met Ser Trp Phe Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
 50                  55                  60

Val Lys Gly Arg Phe Thr Ile Ser Arg Asp Asp Ser Lys Ser Ile Ala
 65                  70                  75                  80

Tyr Leu Gln Met Asn Ser Leu Lys Thr Glu Asp Thr Ala Val Tyr Tyr
                 85                  90                  95

Cys Thr Arg Ala Tyr Ser Ser Ser Tyr Tyr Tyr Tyr Gly Met Asp Val
            100                 105                 110

Trp Gly

<210> SEQ ID NO 30
<211> LENGTH: 115
<212> TYPE: PRT
<213> ORGANISM: Homo sapiens

<400> SEQUENCE: 30

Val Gln Leu Val Glu Ser Gly Gly Gly Leu Val Gln Pro Gly Arg Ser
 1               5                  10                  15

Leu Arg Leu Ser Cys Thr Ala Ser Gly Phe Thr Phe Gly Asp Tyr Ala
            20                  25                  30

Met Ser Trp Phe Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
 50                  55                  60

Val Lys Gly Arg Phe Thr Ile Ser Arg Asp Asp Ser Lys Ser Ile Ala
 65                  70                  75                  80

Tyr Leu Gln Met Asn Ser Leu Lys Thr Glu Asp Thr Ala Val Tyr Tyr
                 85                  90                  95

Cys Thr Ser Asn His Arg Ile Ala Ala Pro Val Gly Asn Tyr Trp Gly
            100                 105                 110

Gln Gly Thr
        115

<210> SEQ ID NO 31
<211> LENGTH: 115
```

```
<212> TYPE: PRT
<213> ORGANISM: Homo sapiens

<400> SEQUENCE: 31

Val Gln Leu Val Glu Ser Gly Gly Gly Leu Val Lys Pro Gly Arg Ser
1               5                   10                  15

Leu Arg Leu Ser Cys Thr Ala Ser Gly Phe Thr Phe Gly Asp Tyr Ala
                20                  25                  30

Met Ser Trp Phe Arg Gln Ala Pro Gly Lys Gly Leu Glu Trp Val Gly
            35                  40                  45

Phe Ile Arg Ser Lys Ala Tyr Gly Gly Thr Thr Glu Tyr Ala Ala Ser
        50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Thr Ala Val Tyr Tyr
                85                  90                  95

Cys Thr Arg Ile Pro Ser Gly Ser Tyr His Tyr Tyr Gly Met Asp
            100                 105                 110

Val Trp Gly
        115

<210> SEQ ID NO 32
<211> LENGTH: 118
<212> TYPE: PRT
<213> ORGANISM: Homo sapiens

<400> SEQUENCE: 32

Val Gln Leu Val Glu Ser Gly Gly Gly Leu Val Gln Pro Gly Arg Ser
1               5                   10                  15

Leu Arg Leu Ser Cys Thr Ala Ser Gly Phe Thr Phe Gly Asp Tyr Ala
                20                  25                  30

Met Ser Trp Phe Arg Gln Ala Pro Gly Lys Gly Leu Glu Trp Val Gly
            35                  40                  45

Phe Ile Arg Ser Lys Ala Tyr Gly Gly Thr Thr Glu Tyr Ala Ala Ser
        50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Thr Arg Trp Gly Lys Glu Gly Ala Thr Gly Glu Asn Phe Asp
            100                 105                 110

Tyr Trp Gly Gln Gly Thr
        115

<210> SEQ ID NO 33
<211> LENGTH: 110
<212> TYPE: PRT
<213> ORGANISM: Homo sapiens

<400> SEQUENCE: 33

Val Gln Leu Val Glu Ser Gly Gly Gly Leu Val Lys Pro Gly Arg Ser
1               5                   10                  15

Leu Arg Leu Ser Cys Thr Ala Ser Gly Phe Thr Phe Gly Asp Tyr Ala
                20                  25                  30

Met Ser Trp Phe Arg Gln Ala Pro Gly Lys Gly Leu Glu Trp Val Gly
            35                  40                  45

Phe Ile Arg Ser Lys Ala Tyr Gly Gly Thr Thr Glu Tyr Ala Ala Ser
```

```
                    50                  55                  60
Val Lys Gly Arg Phe Thr Ile Ser Arg Asp Asp Ser Lys Ser Ile Ala
 65                  70                  75                  80

Tyr Leu Gln Met Asn Ser Leu Lys Thr Glu Asp Thr Ala Val Tyr Tyr
                     85                  90                  95

Cys Thr Arg Asp Gly Ser Tyr Tyr Ala Phe Asp Ile Trp Gly
                100                 105                 110
```

<210> SEQ ID NO 34
<211> LENGTH: 107
<212> TYPE: PRT
<213> ORGANISM: Homo sapiens

<400> SEQUENCE: 34

```
Val Gln Leu Val Glu Ser Gly Gly Gly Leu Val Lys Pro Gly Arg Ser
  1               5                  10                  15

Leu Arg Leu Ser Cys Thr Ala Ser Gly Phe Thr Phe Gly Asp Tyr Ala
                 20                  25                  30

Met Ser Trp Phe Arg Gln Ala Pro Gly Lys Gly Leu Glu Trp Val Gly
             35                  40                  45

Phe Ile Arg Ser Lys Ala Tyr Gly Gly Thr Thr Glu Tyr Ala Ala Ser
         50                  55                  60

Val Lys Gly Arg Phe Thr Ile Ser Arg Asp Asp Ser Lys Ser Ile Ala
 65                  70                  75                  80

Tyr Leu Gln Met Asn Ser Leu Lys Thr Glu Asp Thr Ala Val Tyr Tyr
                     85                  90                  95

Cys Thr Pro Leu Val Tyr Trp Gly Gln Gly Thr
                100                 105
```

<210> SEQ ID NO 35
<211> LENGTH: 119
<212> TYPE: PRT
<213> ORGANISM: Homo sapiens

<400> SEQUENCE: 35

```
Val Gln Leu Val Glu Ser Gly Gly Gly Leu Val Lys Pro Gly Arg Ser
  1               5                  10                  15

Leu Arg Leu Ser Cys Thr Ala Ser Gly Phe Thr Phe Gly Asp Tyr Ala
                 20                  25                  30

Met Ser Trp Phe Arg Gln Ala Pro Gly Lys Gly Leu Glu Trp Val Gly
             35                  40                  45

Phe Ile Arg Ser Lys Ala Tyr Gly Gly Thr Thr Glu Tyr Ala Ala Ser
         50                  55                  60

Val Lys Gly Arg Phe Thr Ile Ser Arg Asp Asp Ser Lys Ser Ile Ala
 65                  70                  75                  80

Tyr Leu Gln Met Asn Ser Leu Lys Thr Glu Asp Thr Ala Val Tyr Tyr
                     85                  90                  95

Cys Thr Arg Asp Pro Leu Leu Tyr Gly Ser Gly Ser Arg Pro Tyr
                100                 105                 110

Asp Ala Phe Asp Ile Trp Gly
            115
```

<210> SEQ ID NO 36
<211> LENGTH: 123
<212> TYPE: PRT
<213> ORGANISM: Homo sapiens

<400> SEQUENCE: 36

```
Val Gln Leu Val Glu Ser Gly Gly Gly Leu Val Gln Pro Gly Arg Ser
1               5                   10                  15

Leu Arg Leu Ser Cys Thr Ala Ser Gly Phe Thr Phe Gly Asp Tyr Ala
            20                  25                  30

Met Ser Trp Phe Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
    50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Thr Ala Val Tyr Tyr
                85                  90                  95

Cys Thr Arg Gly Pro Pro Leu Pro Tyr Tyr Tyr Asp Ser Ser Gly Tyr
            100                 105                 110

Tyr Tyr Glu Gly Asp Tyr Trp Gly Gln Gly Thr
            115                 120

<210> SEQ ID NO 37
<211> LENGTH: 118
<212> TYPE: PRT
<213> ORGANISM: Homo sapiens

<400> SEQUENCE: 37

Val Gln Leu Val Glu Ser Gly Gly Gly Leu Val Lys Pro Gly Arg Ser
1               5                   10                  15

Leu Arg Leu Ser Cys Thr Ala Ser Gly Phe Thr Phe Gly Asp Tyr Ala
            20                  25                  30

Met Ser Trp Phe Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
    50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Thr Arg Asp His Arg Ser Lys Trp Leu Phe Glu Asn Trp Phe Asp
            100                 105                 110

Pro Trp Gly Gln Gly Thr
            115

<210> SEQ ID NO 38
<211> LENGTH: 119
<212> TYPE: PRT
<213> ORGANISM: Homo sapiens

<400> SEQUENCE: 38

Val Gln Leu Val Glu Ser Gly Gly Gly Leu Val Lys Pro Gly Arg Ser
1               5                   10                  15

Leu Arg Leu Ser Cys Thr Ala Ser Gly Phe Thr Phe Gly Asp Tyr Ala
            20                  25                  30

Met Ser Trp Phe Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
    50                  55                  60

Val Lys Gly Arg Phe Thr Ile Ser Arg Asp Asp Ser Lys Ser Ile Ala
65                  70                  75                  80
```

Tyr Leu Gln Met Asn Ser Leu Lys Thr Glu Asp Thr Ala Val Tyr Tyr
                85                  90                  95

Cys Thr Arg Arg Ile Asp Ser Ser Trp Tyr Pro Asp Tyr Tyr Tyr
            100                 105                 110

Tyr Gly Met Asp Val Trp Gly
        115

<210> SEQ ID NO 39
<211> LENGTH: 116
<212> TYPE: PRT
<213> ORGANISM: Homo sapiens

<400> SEQUENCE: 39

Val Gln Leu Val Glu Ser Gly Gly Gly Leu Val Gln Pro Gly Arg Ser
1               5                   10                  15

Leu Arg Leu Ser Cys Thr Ala Ser Gly Phe Thr Phe Gly Asp Tyr Ala
            20                  25                  30

Met Ser Trp Phe Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Thr Arg Glu Trp Tyr Asp Ser Ser Gly Tyr Tyr Ala Tyr Gly Met
            100                 105                 110

Asp Val Trp Gly
        115

<210> SEQ ID NO 40
<211> LENGTH: 117
<212> TYPE: PRT
<213> ORGANISM: Homo sapiens

<400> SEQUENCE: 40

Val Gln Leu Val Glu Ser Gly Gly Gly Ser Val Gln Pro Gly Arg Ser
1               5                   10                  15

Leu Arg Leu Ser Cys Thr Ala Ser Gly Phe Thr Phe Gly Asp Tyr Ala
            20                  25                  30

Met Ser Trp Val Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Thr Arg Asp Trp Glu Ile Ala Ala Arg Pro Glu Ser Phe Asp Tyr
            100                 105                 110

Trp Gly Gln Gly Thr
        115

<210> SEQ ID NO 41
<211> LENGTH: 118
<212> TYPE: PRT
<213> ORGANISM: Homo sapiens

<400> SEQUENCE: 41

Val Gln Leu Val Glu Ser Gly Gly Leu Val Gln Pro Gly Arg Ser
1               5                   10                  15
Leu Arg Leu Ser Cys Thr Thr Ser Gly Phe Thr Phe Gly Asp Tyr Ala
            20                  25                  30
Met Ser Trp Val Arg Gln Ala Pro Gly Lys Gly Leu Glu Trp Val Ser
        35                  40                  45
Phe Ile Arg Ser Lys Ala Tyr Gly Gly Thr Thr Glu Tyr Ala Ala Ser
    50                  55                  60
Val Lys Gly Arg Phe Thr Ile Ser Arg Asp Asp Ser Lys Ser Ile Ala
65                  70                  75                  80
Tyr Leu Gln Met Asn Ser Leu Lys Thr Glu Asp Thr Ala Val Tyr Tyr
                85                  90                  95
Cys Thr Lys Ser Asp His Met Ser Ser Trp Lys Val Asn Pro Phe Asp
            100                 105                 110
Tyr Trp Gly Gln Gly Thr
            115

<210> SEQ ID NO 42
<211> LENGTH: 118
<212> TYPE: PRT
<213> ORGANISM: Homo sapiens

<400> SEQUENCE: 42

Val Gln Val Val Glu Ser Gly Gly Leu Val Gln Pro Gly Arg Ser
1               5                   10                  15
Leu Arg Leu Ser Cys Thr Gly Ser Gly Phe Ile Phe Gly Asp Tyr Ala
            20                  25                  30
Met Ser Trp Val Arg Gln Ala Pro Gly Lys Gly Leu Glu Trp Val Gly
        35                  40                  45
Phe Ile Arg Ser Thr Gly Tyr Gly Gly Thr Ile Gln Tyr Ala Ala Ser
    50                  55                  60
Val Lys Gly Arg Phe Ser Ile Ser Arg Asp Asp Ser Lys Ser Ile Ala
65                  70                  75                  80
Tyr Leu Gln Met Asn Ser Leu Lys Ile Glu Asp Thr Gly Val Tyr Tyr
                85                  90                  95
Cys Thr Arg Gly Pro Tyr Ser Gly Ser Phe Asn Tyr Tyr Tyr
            100                 105                 110
Tyr Met Asp Val Trp Gly
            115

<210> SEQ ID NO 43
<211> LENGTH: 115
<212> TYPE: PRT
<213> ORGANISM: Homo sapiens

<400> SEQUENCE: 43

Val Gln Leu Val Glu Ser Gly Gly Gly Phe Val Gln Pro Gly Arg Ser
1               5                   10                  15
Leu Gly Leu Ser Cys Thr Thr Ser Gly Phe Ser Phe Gly Asp Tyr Ala
            20                  25                  30
Met Thr Trp Val Arg Gln Ala Pro Gly Lys Gly Leu Glu Trp Val Gly
        35                  40                  45
Val Val Arg Asn Lys Ala Tyr Gly Gly Thr Ala Glu Tyr Ala Ala Ser
    50                  55                  60

Val Lys Gly Arg Phe Ile Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Thr Arg Glu Thr Gly Pro Leu Thr Gly Pro Leu Gly Tyr Trp Gly
            100                 105                 110

Gln Gly Thr
        115

<210> SEQ ID NO 44
<211> LENGTH: 111
<212> TYPE: PRT
<213> ORGANISM: Homo sapiens

<400> SEQUENCE: 44

Val Gln Leu Val Glu Ser Gly Gly Gly Leu Val Gln Pro Gly Arg Ser
1               5                   10                  15

Leu Arg Leu Ser Cys Thr Ala Ser Gly Phe Thr Phe Gly Asp Tyr Ala
            20                  25                  30

Met Ser Trp Val Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Thr Arg Gly Ala Gln Thr Trp Ile Asn Trp Gly Gln Gly Thr
            100                 105                 110

<210> SEQ ID NO 45
<211> LENGTH: 121
<212> TYPE: PRT
<213> ORGANISM: Homo sapiens

<400> SEQUENCE: 45

Val Gln Leu Val Glu Ser Gly Gly Gly Leu Val Gln Pro Gly Arg Ser
1               5                   10                  15

Leu Arg Leu Ser Cys Thr Ala Ser Gly Phe Thr Phe Gly Asp Tyr Ala
            20                  25                  30

Met Ser Trp Val Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Thr Arg Ser Val Ala Glu Tyr Gln Leu Thr Gly Tyr Gly Val Gly
            100                 105                 110

Gly Phe Phe Phe Trp Gly Gln Gly Thr
        115                 120

<210> SEQ ID NO 46
<211> LENGTH: 120
<212> TYPE: PRT
<213> ORGANISM: Homo sapiens

<400> SEQUENCE: 46

Gly Gln Leu Val Glu Ser Gly Gly Leu Val Gln Pro Gly Arg Ser
1               5                   10                  15

Leu Arg Leu Ser Cys Thr Ala Ser Gly Phe Thr Phe Gly Asp Tyr Thr
                20                  25                  30

Met Asn Trp Val Arg Gln Ala Pro Gly Lys Gly Leu Glu Trp Val Gly
            35                  40                  45

Phe Ile Arg Arg Lys Ala Tyr Gly Gly Thr Thr Glu Tyr Ala Ala Ser
        50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Leu Tyr Tyr
                85                  90                  95

Cys Thr Arg Asp Arg Arg Asn Tyr Tyr Asp Ser Ser Gly Tyr Trp Gly
            100                 105                 110

His Asp Ala Phe Asn Ile Trp Gly
        115                 120

<210> SEQ ID NO 47
<211> LENGTH: 112
<212> TYPE: PRT
<213> ORGANISM: Homo sapiens

<400> SEQUENCE: 47

Val Gln Met Val Glu Ser Gly Gly Leu Val Gln Pro Gly Arg Ser
1               5                   10                  15

Leu Arg Leu Ser Cys Thr Thr Ser Gly Phe Phe Phe Gly Asp Tyr Ala
                20                  25                  30

Met Ser Trp Val Arg Gln Ala Pro Gly Lys Gly Leu Glu Trp Val Gly
            35                  40                  45

Phe Ile Arg Ser Lys Pro Tyr Gly Gly Thr Thr Gln Tyr Val Ala Ser
        50                  55                  60

Val Lys Gly Arg Phe Ser Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Ser Arg Glu Ser Phe Asp Asn Tyr Arg Ala Phe Asp Met Trp Gly
            100                 105                 110

<210> SEQ ID NO 48
<211> LENGTH: 129
<212> TYPE: PRT
<213> ORGANISM: Homo sapiens

<400> SEQUENCE: 48

Val Gln Leu Val Glu Ser Gly Gly Leu Gly Gln Pro Gly Arg Ser
1               5                   10                  15

Leu Arg Leu Ser Cys Ile Ala Ser Gly Phe Thr Phe Gly Asp Tyr Ala
                20                  25                  30

Met Ser Trp Val Arg Gln Ala Pro Gly Lys Gly Leu Glu Trp Val Gly
            35                  40                  45

Phe Ile Arg Ser Lys Ala Tyr Gly Gly Thr Thr Glu Tyr Ala Ala Ser
        50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr

```
            85                  90                  95
Cys Thr Arg Asp Pro Phe Glu Gly Gly Leu Ile Ala Ala Arg Pro Trp
            100                 105                 110

Arg Gly Trp Met Leu Tyr Pro Ser Ala Phe Asp Tyr Trp Gly Gln Gly
            115                 120                 125

Thr

<210> SEQ ID NO 49
<211> LENGTH: 85
<212> TYPE: PRT
<213> ORGANISM: Homo sapiens

<400> SEQUENCE: 49

Asp Tyr Ala Met Ser Trp Phe Arg Gln Ala Pro Gly Lys Gly Leu Glu
1               5                   10                  15

Trp Val Gly Phe Ile Arg Ser Lys Ala Tyr Gly Gly Thr Thr Glu Tyr
                20                  25                  30

Ala Ala Ser Val Lys Gly Arg Phe Thr Ile Ser Arg Asp Asp Ser Lys
            35                  40                  45

Ser Ile Ala Tyr Leu Gln Met Asn Ser Leu Lys Thr Glu Asp Thr Ala
50                  55                  60

Val Tyr Tyr Cys Thr Arg Ala Leu Tyr Ser Asn Phe Pro Ser Tyr Gly
65                  70                  75                  80

Met Asp Val Trp Gly
                85

<210> SEQ ID NO 50
<211> LENGTH: 91
<212> TYPE: PRT
<213> ORGANISM: Homo sapiens

<400> SEQUENCE: 50

Ser Gly Phe Thr Phe Gly Asp Tyr Ala Met Ser Trp Val Arg Gln Ala
1               5                   10                  15

Pro Gly Lys Gly Leu Glu Trp Val Gly Phe Ile Arg Ser Lys Ala Tyr
                20                  25                  30

Gly Gly Thr Thr Glu Tyr Ala Ala Ser Val Lys Gly Arg Phe Thr Ile
            35                  40                  45

Ser Arg Asp Asp Ser Lys Ser Ile Ala Tyr Leu Gln Met Asn Ser Leu
        50                  55                  60

Lys Thr Glu Asp Thr Ala Val Tyr Tyr Cys Thr Arg Asp Leu Asn Thr
65                  70                  75                  80

Tyr Tyr Tyr Asp Ser Ser Gly Tyr Tyr Trp Gly
                85                  90

<210> SEQ ID NO 51
<211> LENGTH: 125
<212> TYPE: PRT
<213> ORGANISM: Homo sapiens

<400> SEQUENCE: 51

Gly Gly Leu Val Gln Pro Gly Arg Ser Leu Arg Leu Ser Cys Thr Ala
1               5                   10                  15

Ser Gly Phe Thr Phe Gly Asp Tyr Ala Met Ser Trp Val Arg Gln Ala
                20                  25                  30

Pro Gly Lys Gly Leu Glu Trp Val Gly Phe Ile Arg Ser Lys Ala Tyr
            35                  40                  45
```

```
Gly Gly Thr Thr Glu Tyr Ala Ala Ser Val Lys Gly Arg Phe Thr Ile
            50                  55                  60

Ser Arg Asp Asp Ser Lys Ser Ile Ala Tyr Leu Gln Met Asn Ser Leu
 65                  70                  75                  80

Lys Thr Glu Asp Thr Ala Val Tyr Tyr Cys Thr Arg Gly Ser Glu Val
                85                  90                  95

Tyr Cys Ser Ser Thr Ser Cys Tyr Asp Asn Tyr Tyr Tyr Tyr Tyr Met
                100                 105                 110

Asp Val Trp Gly Lys Gly Thr Thr Val Thr Val Ser Ser
            115                 120                 125

<210> SEQ ID NO 52
<211> LENGTH: 128
<212> TYPE: PRT
<213> ORGANISM: Homo sapiens

<400> SEQUENCE: 52

Gly Gly Leu Val Gln Pro Gly Arg Ser Leu Arg Leu Ser Cys Thr Ala
 1               5                  10                  15

Ser Gly Phe Thr Phe Gly Asp Tyr Ala Met Ser Trp Val Arg Gln Ala
            20                  25                  30

Pro Gly Lys Gly Leu Glu Trp Val Gly Phe Ile Arg Ser Lys Ala Tyr
        35                  40                  45

Gly Gly Thr Thr Glu Tyr Ala Ala Ser Val Lys Gly Arg Phe Thr Ile
    50                  55                  60

Ser Arg Asp Asp Ser Lys Ser Ile Ala Tyr Leu Gln Met Asn Ser Leu
 65                  70                  75                  80

Lys Thr Glu Asp Thr Ala Val Tyr Tyr Cys Thr Arg Asp Pro Ala Met
                85                  90                  95

Ala Gln Tyr Tyr Asp Tyr Val Trp Gly Ser Tyr Thr Ala Tyr Tyr
                100                 105                 110

Tyr Gly Met Asp Val Trp Gly Gln Gly Thr Met Val Thr Val Ser Ser
            115                 120                 125

<210> SEQ ID NO 53
<211> LENGTH: 112
<212> TYPE: PRT
<213> ORGANISM: Homo sapiens

<400> SEQUENCE: 53

Gly Gly Leu Val Lys Pro Gly Arg Ser Leu Arg Leu Ser Cys Thr Ala
 1               5                  10                  15

Ser Gly Phe Thr Phe Gly Asp Tyr Ala Met Ser Trp Phe Arg Gln Ala
            20                  25                  30

Pro Gly Lys Gly Leu Glu Trp Val Gly Phe Ile Arg Ser Lys Ala Tyr
        35                  40                  45

Gly Gly Thr Thr Glu Tyr Ala Ala Ser Val Lys Gly Arg Phe Thr Ile
    50                  55                  60

Ser Arg Asp Asp Ser Lys Ser Ile Ala Tyr Leu Gln Met Asn Ser Leu
 65                  70                  75                  80

Lys Thr Glu Asp Thr Ala Val Tyr Tyr Cys Thr Arg Leu Gly Pro Tyr
                85                  90                  95

Tyr Asp Phe Trp Ser Gly Tyr Tyr Phe Asp Tyr Trp Gly Gln Gly
                100                 105                 110

<210> SEQ ID NO 54
<211> LENGTH: 80
```

-continued

```
<212> TYPE: PRT
<213> ORGANISM: Homo sapiens

<400> SEQUENCE: 54

Ser Trp Phe Arg Gln Ala Pro Gly Lys Gly Leu Glu Trp Val Gly Phe
1               5                   10                  15

Ile Arg Ser Lys Ala Tyr Gly Gly Thr Thr Glu Tyr Ala Ala Ser Val
            20                  25                  30

Lys Gly Arg Phe Thr Ile Ser Arg Asp Asp Ser Lys Ser Ile Ala Tyr
        35                  40                  45

Leu Gln Met Asn Ser Leu Lys Thr Glu Asp Thr Ala Leu Tyr Tyr Cys
    50                  55                  60

Thr Arg Ala Pro Ala Ile Ala Ser Gly Gly Pro Phe Asp Pro Trp Gly
65                  70                  75                  80

<210> SEQ ID NO 55
<211> LENGTH: 118
<212> TYPE: PRT
<213> ORGANISM: Homo sapiens

<400> SEQUENCE: 55

Glu Val Ala Leu Val Glu Ser Gly Gly Gly Leu Val Lys Pro Val Ala
1               5                   10                  15

Val Pro Glu Thr Leu Leu Val Ser Ala Ser Gly Phe Thr Phe Gly Asp
            20                  25                  30

His Val Met Ser Trp Phe Arg Gln Ala Pro Gly Lys Gly Pro Asp Trp
        35                  40                  45

Val Gly Phe Ile Arg Ser Lys Val Tyr Gly Gly Thr Ala Glu Tyr Ala
    50                  55                  60

Ala Ser Val Lys Gly Arg Phe Thr Ile Ser Arg Asp Asp Ser Lys Ser
65                  70                  75                  80

Ile Ala Tyr Leu Gln Met Asn Ser Leu Lys Thr Glu Asp Thr Gly Ile
                85                  90                  95

Tyr Tyr Cys Ala Arg Asp His Tyr Ser Asn Phe Trp Gly Gln Gly Thr
            100                 105                 110

Leu Val Thr Val Ser Ser
        115

<210> SEQ ID NO 56
<211> LENGTH: 106
<212> TYPE: PRT
<213> ORGANISM: Homo sapiens

<400> SEQUENCE: 56

Thr Ala Ser Gly Phe Thr Phe Gly Asp Tyr Ala Met Ser Trp Val Arg
1               5                   10                  15

Gln Ala Pro Gly Lys Gly Leu Glu Trp Val Gly Phe Ile Arg Ser Lys
            20                  25                  30

Ala Tyr Gly Gly Thr Thr Glu Tyr Ala Ala Ser Val Lys Gly Arg Phe
        35                  40                  45

Thr Ile Ser Arg Asp Asp Ser Lys Ser Ile Ala Tyr Leu Gln Met Asn
    50                  55                  60

Ser Leu Lys Thr Glu Asp Thr Ala Val Tyr Tyr Cys Thr Arg Ala Thr
65                  70                  75                  80

Tyr Tyr Tyr Asp Ser Ser Gly Tyr Tyr Phe Leu Asp Asn Pro Gly Tyr
                85                  90                  95

Tyr Phe Asp Tyr Trp Gly Gln Gly Thr Leu
```

<210> SEQ ID NO 57
<211> LENGTH: 112
<212> TYPE: PRT
<213> ORGANISM: Homo sapiens

<400> SEQUENCE: 57

Glu Val Gln Met Val Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Cys Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Asp Pro Ile Thr Gly Ser Ser Trp Tyr Asp Tyr Trp
            100                 105                 110

<210> SEQ ID NO 58
<211> LENGTH: 100
<212> TYPE: PRT
<213> ORGANISM: Homo sapiens

<400> SEQUENCE: 58

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 59
<211> LENGTH: 100
<212> TYPE: PRT
<213> ORGANISM: Homo sapiens

<400> SEQUENCE: 59

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

```
Ser Val Lys Gly Arg Phe Thr Ile Ser Arg Asp Asp Ser Lys Ser Ile
 65                  70                  75                  80

Ala Tyr Leu Gln Met Asn Ser Leu Lys Thr Glu Asp Thr Ala Val Tyr
             85                  90                  95

Tyr Cys Thr Arg
            100

<210> SEQ ID NO 60
<211> LENGTH: 134
<212> TYPE: PRT
<213> ORGANISM: Homo sapiens
<220> FEATURE:
<221> NAME/KEY: VARIANT
<222> LOCATION: (1)...(134)
<223> OTHER INFORMATION: Xaa = Any Amino Acid

<400> SEQUENCE: 60

Leu Arg Leu Ser Cys Thr Ala Ser Gly Phe Thr Phe Gly Asp Tyr Ala
 1               5                  10                  15

Met Ser Trp Val Arg Gln Ala Pro Gly Lys Gly Leu Glu Trp Val Gly
             20                  25                  30

Phe Ile Arg Ser Lys Ala Tyr Gly Gly Thr Thr Glu Tyr Ala Ala Ser
         35                  40                  45

Val Lys Gly Arg Phe Thr Ile Ser Arg Asp Asp Ser Lys Ser Ile Ala
 50                  55                  60

Tyr Leu Gln Met Asn Ser Leu Lys Thr Glu Asp Thr Ala Val Tyr Tyr
 65                  70                  75                  80

Cys Thr Arg Asp Gly Phe Tyr Asp Tyr Ile Trp Gly Ser Tyr Arg Tyr
             85                  90                  95

Thr Tyr Glu Gly Phe Ser Asp Tyr Trp Gly Gln Gly Thr Xaa Val Thr
            100                 105                 110

Val Ser Ser Gly Ser Ala Ser Ala Pro Thr Leu Phe Pro Leu Val Ser
            115                 120                 125

Cys Glu Asn Ser Pro Ser
            130

<210> SEQ ID NO 61
<211> LENGTH: 107
<212> TYPE: PRT
<213> ORGANISM: Homo sapiens

<400> SEQUENCE: 61

Gly Gly Ser Leu Arg Leu Ser Cys Thr Ala Ser Gly Phe Thr Phe Gly
 1               5                  10                  15

Asp Tyr Ala Met Ser Trp Phe Arg Gln Ala Pro Gly Lys Gly Leu Glu
             20                  25                  30

Trp Val Gly Phe Ile Arg Ser Lys Ala Tyr Gly Gly Thr Thr Glu Tyr
             35                  40                  45

Ala Ala Ser Val Lys Gly Arg Phe Thr Ile Ser Arg Asp Asp Ser Lys
             50                  55                  60

Ser Ile Ala Tyr Leu Gln Met Asn Ser Leu Lys Thr Glu Asp Thr Ala
 65                  70                  75                  80

Val Tyr Tyr Cys Thr Arg Ser Gly Pro Ser Asp Tyr Tyr Asp Phe Trp
             85                  90                  95

Ser Gly Tyr Tyr Gly Gly Tyr Phe Asp Tyr Trp
            100                 105
```

```
<210> SEQ ID NO 62
<211> LENGTH: 143
<212> TYPE: PRT
<213> ORGANISM: Homo sapiens

<400> SEQUENCE: 62

Arg Leu Ser Cys Thr Ala Ser Gly Phe Thr Phe Gly Asp Tyr Ala Met
1               5                   10                  15

Ser Trp Phe Arg Gln Ala Pro Gly Lys Gly Leu Glu Trp Val Gly Phe
            20                  25                  30

Ile Arg Ser Lys Ala Tyr Gly Gly Thr Thr Glu Tyr Ala Ala Ser Val
        35                  40                  45

Lys Gly Arg Phe Thr Ile Ser Arg Asp Asp Ser Lys Ser Ile Ala Tyr
50                  55                  60

Leu Gln Met Asn Ser Leu Lys Thr Glu Asp Thr Ala Val Tyr Tyr Cys
65                  70                  75                  80

Thr Arg Ala Gln Leu Ile Leu Val Val Pro Ala Ala Ser Trp Asp Tyr
                85                  90                  95

Phe Asp Tyr Trp Gly Gln Gly Thr Leu Val Thr Val Ser Ser Gly Ser
            100                 105                 110

Ala Ser Ala Pro Thr Leu Phe Pro Leu Val Ser Cys Glu Asn Ser Pro
        115                 120                 125

Ser Gly Tyr Glu Gln Arg Ala Val Gly Cys Ser His Arg Ile Leu
130                 135                 140

<210> SEQ ID NO 63
<211> LENGTH: 92
<212> TYPE: PRT
<213> ORGANISM: Homo sapiens

<400> SEQUENCE: 63

Phe Gly Glu Tyr Ala Met Ser Trp Phe Arg Gln Ala Pro Gly Lys Gly
1               5                   10                  15

Leu Glu Trp Val Gly Tyr Ile Arg Ser Lys Pro Phe Gly Gly Thr Ala
            20                  25                  30

Tyr Tyr Ala Ala Ser Val Lys Gly Arg Phe Thr Ile Ser Arg Asp Asp
        35                  40                  45

Thr Lys Ser Ile Ala Tyr Leu Gln Met Asn Ser Leu Lys Thr Glu Asp
50                  55                  60

Thr Ala Val Tyr Phe Cys Thr Arg Glu Tyr Arg Gly Ser Gly Ser Ser
65                  70                  75                  80

Ala Leu Tyr Tyr Tyr Tyr Gly Met Asp Val Trp Gly
                85                  90

<210> SEQ ID NO 64
<211> LENGTH: 103
<212> TYPE: PRT
<213> ORGANISM: Homo sapiens

<400> SEQUENCE: 64

Leu Arg Leu Ser Cys Thr Ala Ser Gly Phe Thr Phe Gly Asp Tyr Ala
1               5                   10                  15

Met Ser Trp Phe Arg Gln Ala Pro Gly Lys Gly Leu Glu Trp Val Gly
            20                  25                  30

Phe Ile Arg Ser Lys Ala Tyr Gly Gly Thr Thr Glu Tyr Ala Ala Ser
        35                  40                  45

Val Lys Gly Arg Phe Thr Ile Ser Arg Asp Asp Ser Lys Ser Ile Ala
50                  55                  60
```

Tyr Leu Gln Met Asn Ser Leu Lys Thr Glu Asp Thr Ala Val Tyr Tyr
65                  70                  75                  80

Cys Thr Arg Gly Tyr Cys Ser Gly Gly Ser Cys Leu Tyr Tyr Tyr
                85                  90                  95

Tyr Gly Met Asp Val Trp Gly
            100

<210> SEQ ID NO 65
<211> LENGTH: 98
<212> TYPE: PRT
<213> ORGANISM: Homo sapiens

<400> SEQUENCE: 65

Leu Arg Leu Ser Cys Thr Ala Ser Gly Phe Thr Phe Gly Asp Tyr Ala
1               5                   10                  15

Met Ser Trp Val Arg Gln Ala Pro Gly Lys Gly Leu Glu Trp Val Gly
            20                  25                  30

Phe Ile Arg Ser Lys Ala Tyr Gly Gly Thr Thr Glu Tyr Ala Ala Ser
        35                  40                  45

Val Lys Gly Arg Phe Thr Ile Ser Arg Asp Asp Ser Lys Ser Ile Ala
    50                  55                  60

Tyr Leu Gln Met Asn Ser Leu Lys Thr Glu Asp Thr Ala Val Tyr Tyr
65                  70                  75                  80

Cys Thr Arg Ala Arg Gly Tyr Ser Ser Gly Trp Tyr Tyr Phe Asp Tyr
                85                  90                  95

Trp Gly

<210> SEQ ID NO 66
<211> LENGTH: 98
<212> TYPE: PRT
<213> ORGANISM: Homo sapiens

<400> SEQUENCE: 66

Leu Arg Leu Ser Cys Thr Ala Ser Gly Phe Thr Phe Gly Asp Tyr Ala
1               5                   10                  15

Met Ser Trp Phe Arg Gln Ala Pro Gly Lys Gly Leu Glu Trp Val Gly
            20                  25                  30

Phe Ile Arg Ser Lys Ala Tyr Gly Gly Thr Thr Glu Tyr Ala Ala Ser
        35                  40                  45

Val Lys Gly Arg Phe Thr Ile Ser Arg Asp Asp Ser Lys Ser Ile Ala
    50                  55                  60

Tyr Leu Gln Met Asn Ser Leu Lys Thr Glu Asp Thr Ala Val Tyr Tyr
65                  70                  75                  80

Cys Thr Arg Asp Gly Gly Gln Gln Leu Gly Arg Thr Lys Phe Asp Tyr
                85                  90                  95

Trp Gly

<210> SEQ ID NO 67
<211> LENGTH: 72
<212> TYPE: PRT
<213> ORGANISM: Homo sapiens

<400> SEQUENCE: 67

Lys Gly Leu Glu Trp Val Gly Phe Ile Arg Ser Lys Ala Tyr Gly Gly
1               5                   10                  15

Thr Thr Glu Tyr Ala Ala Ser Val Lys Gly Arg Phe Thr Ile Ser Arg
            20                  25                  30

Asp Asp Ser Lys Ser Ile Ala Tyr Leu Gln Met Asn Ser Leu Lys Thr
        35                  40                  45

Glu Asp Thr Ala Val Tyr Tyr Cys Thr Arg Ala Gly Val Ala Thr Thr
 50                  55                  60

Arg Gly Lys Phe Asp Tyr Trp Gly
 65                  70

<210> SEQ ID NO 68
<211> LENGTH: 97
<212> TYPE: PRT
<213> ORGANISM: Homo sapiens

<400> SEQUENCE: 68

Ala Ser Gly Phe Thr Phe Gly Asp Tyr Ala Met Ser Trp Phe Arg Gln
 1               5                  10                  15

Ala Pro Gly Lys Gly Leu Glu Trp Val Gly Phe Ile Arg Ser Lys Ala
            20                  25                  30

Tyr Gly Gly Thr Thr Glu Tyr Thr Ala Ser Val Lys Gly Arg Phe Thr
        35                  40                  45

Ile Ser Arg Asp Gly Ser Lys Ser Ile Ala Tyr Leu Gln Met Asn Ser
 50                  55                  60

Leu Lys Thr Glu Asp Thr Ala Val Tyr Tyr Cys Thr Arg Asp Gly Arg
 65                  70                  75                  80

Asp Ile Val Val Val Pro Ala Val Leu Asn Trp Phe Asp Pro Trp
                85                  90                  95

Gly

<210> SEQ ID NO 69
<211> LENGTH: 92
<212> TYPE: PRT
<213> ORGANISM: Homo sapiens

<400> SEQUENCE: 69

Ser Gly Phe Thr Phe Gly Asp Tyr Ala Met Ser Trp Phe Arg Gln Ala
 1               5                  10                  15

Pro Gly Lys Gly Leu Glu Trp Val Gly Phe Ile Arg Ser Lys Ala Tyr
            20                  25                  30

Gly Gly Thr Thr Glu Tyr Ala Ala Ser Val Lys Gly Arg Phe Thr Ile
        35                  40                  45

Ser Arg Asp Asp Ser Lys Ser Ile Ala Tyr Leu Gln Met Asn Ser Leu
 50                  55                  60

Lys Thr Glu Asp Thr Ala Val Tyr Tyr Cys Thr Ser Thr Thr Val Ala
 65                  70                  75                  80

Gly Trp Asp Tyr Tyr Tyr Gly Met Asp Val Trp Gly
                85                  90

<210> SEQ ID NO 70
<211> LENGTH: 76
<212> TYPE: PRT
<213> ORGANISM: Homo sapiens

<400> SEQUENCE: 70

Pro Gly Lys Gly Leu Glu Trp Val Gly Phe Ile Arg Ser Lys Ala Tyr
 1               5                  10                  15

Gly Gly Thr Thr Glu Tyr Thr Ala Ser Val Lys Gly Arg Phe Thr Ile
            20                  25                  30

Ser Arg Asp Gly Ser Lys Ser Ile Ala Tyr Leu Gln Met Asn Ser Leu

```
                35                  40                  45
Lys Thr Glu Asp Thr Ala Val Tyr Tyr Cys Thr Arg Asp Gln Leu Asn
 50                  55                  60

Pro Val Thr Asn Glu Gly Ile Phe Asp Tyr Trp Gly
 65                  70                  75

<210> SEQ ID NO 71
<211> LENGTH: 103
<212> TYPE: PRT
<213> ORGANISM: Homo sapiens

<400> SEQUENCE: 71

Leu Arg Leu Ser Cys Thr Ala Ser Gly Phe Thr Phe Gly Asp Tyr Ala
 1               5                  10                  15

Met Ser Trp Phe Arg Gln Ala Pro Gly Lys Gly Leu Glu Trp Val Gly
                20                  25                  30

Phe Ile Arg Ser Lys Ala Tyr Gly Gly Thr Thr Glu Tyr Ala Ala Ser
                35                  40                  45

Val Lys Gly Arg Phe Thr Ile Ser Arg Asp Asp Ser Lys Ser Ile Ala
 50                  55                  60

Tyr Leu Gln Met Asn Ser Leu Lys Thr Glu Asp Thr Ala Val Tyr Tyr
 65                  70                  75                  80

Cys Thr Arg Val Gln Asn Trp Ala Ile Val Val Val Ala Ala Thr
                85                  90                  95

Pro Val Ala Asp Tyr Trp Gly
            100

<210> SEQ ID NO 72
<211> LENGTH: 74
<212> TYPE: PRT
<213> ORGANISM: Homo sapiens

<400> SEQUENCE: 72

Pro Gly Lys Gly Leu Glu Trp Val Gly Phe Ile Arg Ser Lys Ala Tyr
 1               5                  10                  15

Gly Gly Thr Thr Glu Tyr Ala Ala Ser Val Lys Gly Arg Phe Thr Ile
                20                  25                  30

Ser Arg Asp Asp Ser Lys Ser Ile Ala Tyr Leu Gln Met Asn Ser Leu
                35                  40                  45

Lys Thr Glu Asp Thr Ala Val Tyr Tyr Cys Thr Arg Asp Gly Gly Phe
 50                  55                  60

Ser Ser Gly Trp Arg Phe Asp Tyr Trp Gly
 65                  70

<210> SEQ ID NO 73
<211> LENGTH: 75
<212> TYPE: PRT
<213> ORGANISM: Homo sapiens

<400> SEQUENCE: 73

Pro Gly Lys Gly Leu Glu Trp Val Gly Phe Ile Arg Ser Lys Ala Tyr
 1               5                  10                  15

Gly Gly Thr Thr Glu Tyr Ala Ala Ser Val Lys Gly Arg Phe Thr Ile
                20                  25                  30

Ser Arg Asp Asp Ser Lys Ser Ile Ala Tyr Leu Gln Met Asn Ser Leu
                35                  40                  45

Lys Thr Glu Asp Thr Ala Val Tyr Tyr Cys Thr Arg Asp Leu Ser Glu
 50                  55                  60
```

```
Leu Leu Tyr Tyr Tyr Gly Met Asp Val Trp Gly
 65                  70                  75
```

<210> SEQ ID NO 74
<211> LENGTH: 92
<212> TYPE: PRT
<213> ORGANISM: Homo sapiens

<400> SEQUENCE: 74

```
Gly Phe Thr Phe Gly Asp Tyr Ala Met Ser Trp Phe Arg Gln Ala Pro
  1               5                  10                  15

Gly Lys Gly Leu Glu Trp Val Gly Phe Ile Arg Ser Lys Ala Tyr Gly
             20                  25                  30

Gly Thr Thr Glu Tyr Thr Ala Ser Val Lys Gly Arg Phe Thr Ile Ser
         35                  40                  45

Arg Asp Gly Ser Lys Ser Ile Ala Tyr Leu Gln Met Asn Ser Leu Lys
     50                  55                  60

Thr Glu Asp Thr Ala Val Tyr Tyr Cys Thr Arg Val Thr Gly Val Val
 65                  70                  75                  80

Val Pro Ala Trp Ser Tyr Tyr Phe Asp Tyr Trp Gly
                 85                  90
```

<210> SEQ ID NO 75
<211> LENGTH: 79
<212> TYPE: PRT
<213> ORGANISM: Homo sapiens

<400> SEQUENCE: 75

```
Arg Gln Ala Pro Gly Lys Gly Leu Glu Trp Val Gly Phe Ile Arg Ser
  1               5                  10                  15

Lys Ala Tyr Gly Gly Thr Thr Glu Tyr Ala Ala Ser Val Lys Gly Arg
             20                  25                  30

Phe Thr Ile Ser Arg Asp Asp Ser Lys Ser Ile Ala Tyr Leu Gln Met
         35                  40                  45

Asn Ser Leu Lys Thr Glu Asp Thr Ala Val Tyr Tyr Cys Thr Arg Ile
     50                  55                  60

Gly Val Phe Gly Asp Tyr Gly Tyr Trp Tyr Phe Asp Leu Trp Gly
 65                  70                  75
```

<210> SEQ ID NO 76
<211> LENGTH: 107
<212> TYPE: PRT
<213> ORGANISM: Homo sapiens

<400> SEQUENCE: 76

```
Ser Gly Gly Gly Leu Val Gln Pro Gly Arg Ser Leu Arg Leu Ser Cys
  1               5                  10                  15

Thr Ala Ser Gly Phe Thr Phe Gly Asp Tyr Ala Met Ser Trp Val Arg
             20                  25                  30

Gln Ala Pro Gly Lys Gly Leu Glu Trp Val Gly Phe Ile Arg Ser Lys
         35                  40                  45

Ala Tyr Gly Gly Thr Thr Glu Tyr Ala Ala Ser Val Lys Gly Arg Phe
     50                  55                  60

Thr Ile Ser Arg Asp Asp Ser Lys Ser Ile Ala Tyr Leu Gln Met Asn
 65                  70                  75                  80

Ser Leu Lys Thr Glu Asp Thr Ala Val Tyr Tyr Cys Thr Ser Gly Arg
                 85                  90                  95
```

Arg Trp Tyr Leu Asp Tyr Trp Gly Gln Gly Thr
            100                 105

<210> SEQ ID NO 77
<211> LENGTH: 126
<212> TYPE: PRT
<213> ORGANISM: Homo sapiens

<400> SEQUENCE: 77

Met Ala Gln Val Gln Leu Val Gln Ser Gly Gly Gly Leu Val Gln Pro
1               5                   10                  15

Gly Arg Ser Leu Arg Leu Ser Cys Thr Ala Ser Gly Phe Thr Phe Gly
            20                  25                  30

Asp Tyr Val Met Ser Trp Val Arg Gln Ala Pro Gly Lys Gly Leu Glu
        35                  40                  45

Trp Val Gly Phe Ile Arg Ser Lys Ala Tyr Gly Gly Thr Thr Asp Tyr
    50                  55                  60

Ala Ala Ser Val Lys Gly Arg Phe Ser Met Ser Arg Asp Asp Ser Lys
65                  70                  75                  80

Ser Ile Ala Tyr Leu Gln Met Asn Ser Leu Lys Thr Glu Asp Thr Ala
                85                  90                  95

Val Tyr Tyr Cys Thr Arg Gly Asp Asp Tyr Tyr Gly Ser Gly Thr Tyr
            100                 105                 110

Ile Pro Arg Asp Tyr Trp Asp His Gly His Arg Leu Asn His
        115                 120                 125

<210> SEQ ID NO 78
<211> LENGTH: 124
<212> TYPE: PRT
<213> ORGANISM: Homo sapiens

<400> SEQUENCE: 78

Gln Val Gln Leu Leu Glu Ser Gly Gly Gly Leu Val Gln Pro Gly Arg
1               5                   10                  15

Ser Leu Arg Leu Ser Cys Thr Thr Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Gln Ala Tyr Ser Gly Thr Thr Ala Tyr Ala Ala
    50                  55                  60

Ser Val Glu Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ser Arg Asp Arg Glu Thr Ser Ala Ala Ala Arg Pro Phe Asp
            100                 105                 110

Tyr Trp Gly Gln Gly Thr Leu Val Thr Val Ser Ser
        115                 120

<210> SEQ ID NO 79
<211> LENGTH: 127
<212> TYPE: PRT
<213> ORGANISM: Homo sapiens

<400> SEQUENCE: 79

Val Gln Leu Val Glu Ser Gly Gly Gly Leu Val Gln Pro Gly Arg Ser
1               5                   10                  15

Leu Arg Leu Ser Cys Thr Ala Ser Gly Phe Thr Phe Gly Asp Tyr Ala

Met Ser Trp Val Arg Gln Ala Pro Gly Lys Gly Leu Glu Trp Val Gly
                20                  25                  30

Phe Ile Arg Ser Lys Ala Tyr Gly Gly Thr Thr Glu Tyr Ala Ala Ser
         35                  40                  45

Val Lys Gly Arg Phe Thr Ile Ser Arg Asp Asp Ser Lys Ser Ile Ala
 65                  70                  75                  80

Tyr Leu Gln Met Asn Ser Leu Lys Thr Glu Asp Thr Ala Val Tyr Tyr
                 85                  90                  95

Cys Thr Arg Ala Pro Arg Leu Glu Leu Arg Arg Tyr Tyr Tyr Tyr Tyr
                100                 105                 110

Tyr Met Asp Val Trp Gly Lys Gly Thr Thr Val Thr Val Ser Ser
                115                 120                 125

<210> SEQ ID NO 80
<211> LENGTH: 101
<212> TYPE: PRT
<213> ORGANISM: Homo sapiens

<400> SEQUENCE: 80

Thr Ala Ser Gly Phe Thr Phe Gly Asp Tyr Ala Met Ser Trp Val Arg
 1               5                  10                  15

Gln Ala Pro Gly Lys Gly Leu Glu Trp Val Gly Phe Ile Arg Ser Lys
                20                  25                  30

Ala Tyr Gly Gly Thr Thr Glu Tyr Ala Ala Ser Val Lys Gly Arg Phe
             35                  40                  45

Thr Ile Ser Arg Asp Asp Ser Lys Ser Ile Ala Tyr Leu Gln Met Asn
         50                  55                  60

Ser Leu Lys Thr Glu Asp Thr Ala Val Tyr Tyr Cys Thr Ser His Ser
 65                  70                  75                  80

Ser Ser Trp Asp Tyr Tyr Tyr Tyr Tyr Tyr Tyr Met Asp Val Trp
                 85                  90                  95

Gly Lys Gly Thr Thr
            100

<210> SEQ ID NO 81
<211> LENGTH: 126
<212> TYPE: PRT
<213> ORGANISM: Homo sapiens

<400> SEQUENCE: 81

Met Glu Phe Gly Leu Ser Trp Val Phe Leu Val Ala Ile Leu Lys Gly
 1               5                  10                  15

Val Gln Cys Glu Val Gln Leu Val Glu Ser Gly Gly Gly Leu Val Gln
                20                  25                  30

Pro Gly Arg Ser Leu Arg Leu Ser Cys Thr Ala Ser Gly Phe Thr Phe
             35                  40                  45

Gly Asp Tyr Ala Met Ser Trp Phe Arg Gln Ala Pro Gly Lys Gly Leu
         50                  55                  60

Glu Trp Val Gly Phe Ile Arg Ser Lys Ala Tyr Gly Gly Thr Thr Glu
 65                  70                  75                  80

Tyr Ala Ala Ser Val Lys Gly Arg Phe Thr Ile Ser Arg Asp Asp Ser
                 85                  90                  95

Lys Ser Ile Ala Tyr Leu Gln Met Asn Ser Leu Lys Thr Glu Asp Thr
                100                 105                 110

Ala Val Tyr Tyr Cys Thr Arg Asp Thr Val Arg Gly Gly Gln

<210> SEQ ID NO 82
<211> LENGTH: 118
<212> TYPE: PRT
<213> ORGANISM: Homo sapiens

<400> SEQUENCE: 82

Glu Val Gln Leu Val Gln Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Val Trp Phe Arg Gln Ala Pro Gly Lys Gly Leu Glu Trp Leu
        35                  40                  45

Ala Phe Ile Arg Ser Lys Ala Ser Gly Glu Thr Thr Glu Tyr Ala Ala
    50                  55                  60

Ser Val Gln Asp Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Ser Cys Asn Gly Tyr Tyr Asp Ser Ser Gly Tyr Tyr Ser Asp Tyr Pro
            100                 105                 110

Val Val Thr Asn Pro Val
        115

<210> SEQ ID NO 83
<211> LENGTH: 125
<212> TYPE: PRT
<213> ORGANISM: Homo sapiens

<400> SEQUENCE: 83

Gln Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Asp Arg Pro Leu Val Pro Arg Ser Glu Trp Phe Asp
            100                 105                 110

Pro Trp Gly Gln Gly Thr Leu Val Thr Val Ser Ser Gly
        115                 120                 125

<210> SEQ ID NO 84
<211> LENGTH: 97
<212> TYPE: PRT
<213> ORGANISM: Homo sapiens

<400> SEQUENCE: 84

Ala Met Ser Trp Val Arg Gln Ala Pro Gly Lys Gly Leu Glu Trp Val
1               5                   10                  15

Gly Phe Ile Arg Ser Lys Ala Tyr Gly Gly Thr Thr Glu Tyr Ala Ala
            20                  25                  30

```
Ser Val Lys Gly Arg Phe Thr Ile Ser Arg Asp Asp Ser Lys Ser Ile
            35                  40                  45

Ala Tyr Leu Gln Met Asn Ser Leu Lys Thr Glu Asp Thr Ala Val Tyr
 50                  55                  60

Tyr Cys Thr Arg Val Arg Thr Pro Pro Asp Leu Ile Ile Val Val Val
 65                  70                  75                  80

Pro Ala Ala Ser Leu Asp Tyr Tyr Tyr Met Asp Val Trp Gly Lys
                 85                  90                  95

Gly

<210> SEQ ID NO 85
<211> LENGTH: 133
<212> TYPE: PRT
<213> ORGANISM: Homo sapiens

<400> SEQUENCE: 85

Leu Val Gln Leu Val Glu Ser Gly Gly Gly Leu Val Gln Pro Gly Arg
 1               5                  10                  15

Ser Leu Arg Leu Ser Cys Thr Ala Ser Gly Phe Thr Phe Gly Asp Tyr
                 20                  25                  30

Ala Met Ser Trp Val Arg Gln Ala Pro Gly Lys Gly Leu Glu Trp Val
             35                  40                  45

Gly Phe Ile Arg Ser Lys Ala Tyr Gly Gly Thr Thr Glu Tyr Ala Ala
         50                  55                  60

Ser Val Lys Gly Arg Phe Thr Ile Ser Arg Asp Asp Ser Lys Ser Ile
 65                  70                  75                  80

Ala Tyr Leu Gln Met Asn Ser Leu Lys Thr Glu Asp Thr Ala Val Tyr
                 85                  90                  95

Tyr Cys Thr Arg Asp Ala Arg Leu Gln Tyr Tyr Asp Phe Trp Ser Gly
                100                 105                 110

Tyr Tyr Thr Ala Pro Gly Trp Phe Asp Pro Trp Gly Gln Gly Thr Leu
            115                 120                 125

Val Thr Val Ser Ser
        130

<210> SEQ ID NO 86
<211> LENGTH: 130
<212> TYPE: PRT
<213> ORGANISM: Homo sapiens

<400> SEQUENCE: 86

Leu Val Gln Leu Val Glu Ser Gly Gly Gly Leu Val Gln Pro Gly Arg
 1               5                  10                  15

Ser Leu Arg Leu Ser Cys Thr Ala Ser Gly Phe Thr Phe Gly Asp Tyr
                 20                  25                  30

Ala Met Ser Trp Val Arg Gln Ala Pro Gly Lys Gly Leu Glu Trp Val
             35                  40                  45

Gly Phe Ile Arg Ser Lys Ala Tyr Gly Gly Thr Thr Glu Tyr Ala Ala
         50                  55                  60

Ser Val Lys Gly Arg Phe Thr Ile Ser Arg Asp Asp Ser Lys Ser Ile
 65                  70                  75                  80

Ala Tyr Leu Gln Met Asn Ser Leu Lys Thr Glu Asp Thr Ala Val Tyr
                 85                  90                  95

Tyr Cys Thr Arg Asp Leu Gln Lys Trp Asp Cys Ser Gly Gly Ser Cys
                100                 105                 110
```

```
Phe Thr Ser Gly Val Asp Tyr Trp Gly Gln Gly Thr Leu Val Thr Val
            115                 120                 125
Ser Ser
    130

<210> SEQ ID NO 87
<211> LENGTH: 133
<212> TYPE: PRT
<213> ORGANISM: Homo sapiens

<400> SEQUENCE: 87

Leu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
            35                  40                  45

Gly Phe Ile Arg Ser Arg Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Asp Ala Arg Leu Gln Tyr Tyr Asp Phe Trp Ser Gly
            100                 105                 110

Tyr Tyr Thr Ala Pro Gly Trp Phe Asp Pro Trp Gly Gln Gly Thr Leu
            115                 120                 125

Val Thr Val Ser Ser
            130

<210> SEQ ID NO 88
<211> LENGTH: 131
<212> TYPE: PRT
<213> ORGANISM: Homo sapiens

<400> SEQUENCE: 88

Leu Val Gln Leu Val Glu Ser Gly Gly Gly Leu Val Gln Pro Gly Arg
1               5                   10                  15

Ser Leu Arg Leu Ser Cys Thr Ala Pro Gly Phe Thr Phe Gly Asp Tyr
            20                  25                  30

Ala Met Ser Trp Val Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Asp Gln Asp Cys Thr Asn Gly Val Cys Tyr Thr Phe
            100                 105                 110

Gly Val Glu Asn Trp Phe Asp Pro Trp Gly Gln Gly Thr Leu Val Thr
            115                 120                 125

Val Ser Ser
    130

<210> SEQ ID NO 89
<211> LENGTH: 170
```

<212> TYPE: PRT
<213> ORGANISM: Homo sapiens

<400> SEQUENCE: 89

Trp Val Phe Leu Val Ala Ile Leu Lys Gly Val Gln Cys Glu Val Gln
1               5                   10                  15

Leu Val Glu Ser Gly Gly Ala Leu Val Gln Pro Gly Arg Ser Leu Thr
            20                  25                  30

Leu Ser Cys Thr Ser Ser Gly Leu Thr Phe Asp Asp Tyr Phe Met Ser
        35                  40                  45

Trp Phe Arg Gln Ala Pro Gly Lys Gly Leu Glu Trp Val Gly Phe Ile
    50                  55                  60

Arg Ser Lys Thr Tyr Gly Gly Thr Thr Glu Tyr Ala Ala Ser Val Gln
65                  70                  75                  80

Gly Arg Phe Thr Ile Ser Arg Asp Asp Ser Lys Ser Ile Ala Tyr Leu
                85                  90                  95

Gln Met Asn Ser Leu Lys Thr Glu Asp Thr Ala Ile Tyr Tyr Cys Ser
            100                 105                 110

Pro Gly Gly Ser Ala Tyr Tyr His Glu Asp Phe Gln Gln Trp Gly Pro
        115                 120                 125

Gly Thr Met Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro
                165                 170

<210> SEQ ID NO 90
<211> LENGTH: 172
<212> TYPE: PRT
<213> ORGANISM: Homo sapiens

<400> SEQUENCE: 90

Trp Val Phe Leu Val Ala Ile Leu Lys Gly Val Gln Cys Glu Val Gln
1               5                   10                  15

Leu Val Glu Ser Gly Gly Gly Leu Val Gln Pro Gly Arg Ser Leu Arg
            20                  25                  30

Leu Ser Cys Thr Ala Ser Gly Phe Thr Phe Ser Asp Tyr Ala Met Ile
        35                  40                  45

Trp Phe Arg Gln Ala Pro Gly Lys Gly Leu Glu Trp Val Ala Phe Ile
    50                  55                  60

Arg Lys Lys Ala Tyr Gly Gly Thr Thr Asp Tyr Ala Ala Ser Val Lys
65                  70                  75                  80

Gly Arg Phe Thr Ile Ser Arg Asp Asp Ser Lys Ser Ile Ala Tyr Leu
                85                  90                  95

Gln Met Asn Ser Leu Lys Thr Glu Asp Thr Ala Leu Tyr Tyr Cys Thr
            100                 105                 110

Arg Asp Ser Glu Gly Trp Gly Val Tyr Tyr Gly Met Asp Val Trp
        115                 120                 125

Gly Lys Gly Thr Thr Val Thr Val Ser Ser Gly Ser Ala Ser Ala Pro
    130                 135                 140

Thr Leu Phe Pro Leu Val Ser Cys Glu Asn Ser Pro Ser Asn Thr Ser
145                 150                 155                 160

Ser Val Ala Val Gly Cys Leu Ala Gln Asp Phe Leu
                165                 170

<210> SEQ ID NO 91
<211> LENGTH: 127
<212> TYPE: PRT
<213> ORGANISM: Homo sapiens

<400> SEQUENCE: 91

```
Glu Val Gln Leu Leu Glu Ser Gly Gly Gly Leu Val Gln Pro Gly Arg
1               5                   10                  15

Ser Leu Arg Leu Ser Cys Leu Ala Ser Gly Phe Thr Phe Glu Asp Tyr
            20                  25                  30

Ala Met His Trp Val Arg Gln Ala Pro Gly Lys Gly Leu Glu Trp Ile
        35                  40                  45

Gly Phe Ile Arg Asn Lys Ala Tyr Gly Gly Thr Thr Glu Tyr Ala Ala
    50                  55                  60

Ser Val Lys Gly Arg Phe Val Ile Ser Arg Glu Asp Pro Lys Ser Ile
65                  70                  75                  80

Ala Tyr Leu Gln Met Asn Ser Leu Lys Ile Glu Asp Thr Ala Val Tyr
                85                  90                  95

Tyr Cys Met Arg Tyr Arg Arg Val Pro Ile Phe Gly Gly Ile His Ser
            100                 105                 110

Phe Phe Asp Tyr Trp Gly Leu Gly Thr Leu Val Ser Val Ser Ser
        115                 120                 125
```

<210> SEQ ID NO 92
<211> LENGTH: 127
<212> TYPE: PRT
<213> ORGANISM: Homo sapiens

<400> SEQUENCE: 92

```
Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Phe Pro Thr Pro Gly Tyr Tyr Tyr Asp Ser Ser Gly Tyr
            100                 105                 110

Phe Pro Asp Tyr Trp Gly Gln Gly Thr Leu Val Thr Val Ser Ser
        115                 120                 125
```

<210> SEQ ID NO 93
<211> LENGTH: 110
<212> TYPE: PRT
<213> ORGANISM: Homo sapiens

<400> SEQUENCE: 93

```
Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
```

```
                35                  40                  45
Gly Phe Ile Arg Ser Lys Ala Tyr Gly Gly Thr Thr Glu Tyr Ala Ala
        50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Ser Ser Ser Arg Val Ser Asn Phe Asp Tyr Trp
            100                 105                 110

<210> SEQ ID NO 94
<211> LENGTH: 102
<212> TYPE: PRT
<213> ORGANISM: Homo sapiens

<400> SEQUENCE: 94

Ser Gly Gly Ala Leu Val His Pro Trp Arg Ser Leu Arg Leu Ser Cys
1               5                   10                  15

Ser Thr Ser Gly Phe Thr Phe Gly Asp Tyr Ser Met Thr Trp Val Arg
                20                  25                  30

Gln Ala Pro Gly Lys Gly Leu Glu Trp Ile Ser Ser Ile Arg Gly Lys
            35                  40                  45

Ser Phe Gly Gly Thr Thr Met Tyr Ala Ala Ser Val Lys Asp Arg Phe
        50                  55                  60

Thr Ile Ser Arg Asp Asp Ser Lys Ser Ile Ala Tyr Leu Gln Met Asn
65                  70                  75                  80

Ser Leu Lys Ile Glu Asp Thr Ala Met Tyr Phe Cys Thr Arg Asn Leu
                85                  90                  95

His Asp Phe Asp Tyr Trp
            100

<210> SEQ ID NO 95
<211> LENGTH: 88
<212> TYPE: PRT
<213> ORGANISM: Homo sapiens

<400> SEQUENCE: 95

Phe Thr Phe Gly Asp Tyr Ala Met Ser Trp Val Arg Gln Ala Pro Gly
1               5                   10                  15

Lys Gly Leu Glu Trp Val Gly Phe Ile Arg Ser Lys Ala Tyr Gly Gly
                20                  25                  30

Thr Thr Glu Tyr Ala Ala Ser Val Lys Gly Arg Phe Thr Ile Ser Arg
            35                  40                  45

Asp Asp Ser Lys Ser Ile Ala Tyr Leu Gln Met Asn Ser Leu Lys Thr
        50                  55                  60

Glu Asp Thr Ala Val Tyr Tyr Cys Thr Arg Asp Glu Ser Phe Asp Trp
65                  70                  75                  80

Leu Phe Pro Pro Leu Asp Tyr Trp
                85

<210> SEQ ID NO 96
<211> LENGTH: 67
<212> TYPE: PRT
<213> ORGANISM: Homo sapiens

<400> SEQUENCE: 96

Pro Gly Lys Gly Leu Glu Trp Ile Gly Phe Ile Arg Ser Lys Ala Tyr
1               5                   10                  15
```

Gly Glu Thr Ala Glu His Ala Ala Ser Val Lys Gly Arg Phe Thr Ile
            20                  25                  30

Ser Arg Asp Asp Ser Lys Ser Ile Ala Tyr Leu Gln Met Asn Ser Leu
            35                  40                  45

Lys Thr Glu Asp Thr Ala Val Tyr Tyr Cys Thr Ser Ser Pro Gly Met
 50                  55                  60

Ala Val Trp
 65

<210> SEQ ID NO 97
<211> LENGTH: 134
<212> TYPE: PRT
<213> ORGANISM: Homo sapiens

<400> SEQUENCE: 97

Leu Ala Ala Ile Ile Arg Gly Val Gln Cys Glu Val Gln Leu Val Glu
 1               5                  10                  15

Ser Gly Gly Gly Leu Val Gln Pro Gly Arg Ser Leu Arg Leu Ser Cys
            20                  25                  30

Thr Ala Ser Gly Phe Thr Phe Gly Asp Tyr Thr Val Ser Trp Leu Arg
            35                  40                  45

Gln Ala Pro Gly Lys Gly Leu Glu Tyr Val Gly Phe Ile Arg Ser Lys
 50                  55                  60

Thr His Gly Gly Thr Ala Glu Tyr Ala Ala Ser Leu Asn Gly Arg Phe
 65                  70                  75                  80

Thr Ile Ser Arg Glu Asp Ser Lys Ser Ile Ala Tyr Leu Gln Met Asn
                85                  90                  95

Ser Leu Lys Thr Glu Asp Thr Ala Val Tyr Tyr Cys Thr Arg Asp Ser
            100                 105                 110

Lys Val Asp Gly Lys Leu Asp Ala Phe Asp Ile Trp Gly Gln Gly Thr
        115                 120                 125

Met Val Thr Val Ser Ser
        130

<210> SEQ ID NO 98
<211> LENGTH: 89
<212> TYPE: PRT
<213> ORGANISM: Homo sapiens

<400> SEQUENCE: 98

Met Ser Trp Val Arg Gln Ala Ser Gly Lys Gly Leu Glu Trp Val Gly
 1               5                  10                  15

Phe Ile Arg Ser Lys Ala Tyr Gly Gly Thr Thr Glu Tyr Ala Ala Ser
            20                  25                  30

Val Lys Gly Arg Phe Thr Ile Ser Arg Asp Asp Ser Lys Ser Ile Ala
            35                  40                  45

Tyr Leu Gln Met Asn Ser Leu Lys Thr Glu Asp Thr Ala Val Tyr Tyr
 50                  55                  60

Cys Thr Arg Glu Ile Glu Gly Tyr Cys Thr Gly Gly Val Cys Phe Lys
 65                  70                  75                  80

Thr Thr Arg Asn Ala Phe Asp Ile Trp
                85

<210> SEQ ID NO 99
<211> LENGTH: 133
<212> TYPE: PRT
<213> ORGANISM: Homo sapiens

```
<220> FEATURE:
<221> NAME/KEY: VARIANT
<222> LOCATION: (1)...(133)
<223> OTHER INFORMATION: Xaa = Any Amino Acid

<400> SEQUENCE: 99

Cys Ala Leu Ile Xaa Arg Val Gln Cys Glu Val Gln Leu Val Glu Ser
1               5                   10                  15

Gly Gly Gly Leu Val Gln Pro Gly Arg Ser Leu Arg Leu Ser Cys Thr
            20                  25                  30

Ala Ser Gly Phe Thr Phe Gly Asp Tyr Thr Val Ser Trp Leu Arg Gln
        35                  40                  45

Ala Pro Gly Lys Gly Leu Glu Tyr Val Gly Phe Ile Arg Ser Lys Thr
    50                  55                  60

His Gly Gly Thr Ala Glu Tyr Ala Ala Ser Leu Asn Gly Arg Phe Thr
65                  70                  75                  80

Ile Ser Arg Glu Asp Ser Lys Ser Ile Ala Tyr Leu Gln Met Asn Ser
                85                  90                  95

Leu Lys Thr Glu Asp Thr Ala Val Tyr Tyr Cys Thr Arg Asp Ser Lys
            100                 105                 110

Val Asp Gly Lys Leu Asp Ala Phe Asp Ile Trp Gly Gln Gly Thr Met
        115                 120                 125

Val Thr Val Ser Ser
    130

<210> SEQ ID NO 100
<211> LENGTH: 124
<212> TYPE: PRT
<213> ORGANISM: Homo sapiens

<400> SEQUENCE: 100

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Glu Lys His Tyr Asp Ile Leu Thr Asp Pro Phe Asp
            100                 105                 110

Tyr Trp Gly Gln Gly Thr Leu Val Thr Val Ser Ser
        115                 120

<210> SEQ ID NO 101
<211> LENGTH: 132
<212> TYPE: PRT
<213> ORGANISM: Homo sapiens

<400> SEQUENCE: 101

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30
```

```
Ala Met Ser Trp Val Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
        50                  55                  60

Ser Val Lys Gly Arg Phe Thr Ile Ser Arg Asp Asp Ser Lys Ser Ile
 65                 70                  75                  80

Ala Tyr Leu Gln Met Asn Ser Leu Lys Thr Glu Asp Thr Ala Val Tyr
                85                  90                  95

Tyr Cys Thr Arg Val Pro Ser Glu Val Leu Pro Ala Ala Met Ala Val
            100                 105                 110

Tyr Tyr Tyr Tyr Tyr Met Asp Val Trp Gly Lys Gly Thr Thr Val
        115                 120                 125

Thr Val Ser Ser
        130

<210> SEQ ID NO 102
<211> LENGTH: 114
<212> TYPE: PRT
<213> ORGANISM: Homo sapiens

<400> SEQUENCE: 102

Glu Val Gln Leu Val Glu Ser Gly Gly Gly Leu Val Gln Pro Gly Arg
 1               5                  10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
        50                  55                  60

Ser Val Lys Gly Arg Phe Thr Ile Ser Arg Asp Asp Ser Lys Ser Ile
 65                 70                  75                  80

Ala Tyr Leu Gln Met Asn Ser Leu Lys Thr Glu Asp Thr Ala Val Tyr
                85                  90                  95

Tyr Cys Thr Arg Val Tyr Ser Ser Gly Trp Tyr Gly Gly Leu Val Asp
            100                 105                 110

Tyr Trp

<210> SEQ ID NO 103
<211> LENGTH: 129
<212> TYPE: PRT
<213> ORGANISM: Homo sapiens

<400> SEQUENCE: 103

Glu Val Gln Leu Val Glu Ser Gly Gly Gly Leu Val Lys Pro Gly Arg
 1               5                  10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
        50                  55                  60

Ser Val Lys Gly Arg Phe Thr Ile Ser Arg Asp Asp Ser Lys Ser Ile
 65                 70                  75                  80

Ala Tyr Leu Gln Met Asn Ser Leu Lys Thr Glu Asp Thr Ala Val Tyr
                85                  90                  95
```

Tyr Cys Thr Arg Ala Trp Arg Gly Asn Tyr Cys Ser Gly Gly Ser Cys
            100                 105                 110

Tyr Leu Tyr Phe Gln His Trp Gly Gln Gly Thr Leu Val Thr Val Ser
        115                 120                 125

Ser

<210> SEQ ID NO 104
<211> LENGTH: 134
<212> TYPE: PRT
<213> ORGANISM: Homo sapiens

<400> SEQUENCE: 104

Leu Val Ala Leu Leu Gly Gly Val Gln Cys Glu Val Gln Leu Val Glu
1               5                   10                  15

Ser Gly Gly Gly Leu Val Gln Pro Gly Arg Ser Leu Arg Leu Ser Cys
            20                  25                  30

Thr Ala Ser Gly Phe Thr Phe Gly Asp Tyr Thr Val Ser Trp Leu Arg
        35                  40                  45

Gln Ala Pro Gly Lys Gly Leu Glu Tyr Val Gly Phe Ile Arg Ser Lys
    50                  55                  60

Thr His Gly Gly Thr Ala Glu Tyr Ala Ala Ser Leu Asn Gly Arg Phe
65                  70                  75                  80

Thr Ile Ser Arg Glu Asp Ser Lys Ser Ile Ala Tyr Leu Gln Met Asn
                85                  90                  95

Ser Leu Lys Thr Glu Asp Thr Ala Val Tyr Tyr Cys Thr Arg Asp Ser
            100                 105                 110

Lys Val Asp Gly Lys Leu Asp Ala Phe Asp Ile Trp Gly Gln Gly Thr
        115                 120                 125

Met Val Thr Val Ser Ser
        130

<210> SEQ ID NO 105
<211> LENGTH: 21
<212> TYPE: PRT
<213> ORGANISM: Artificial Sequence
<220> FEATURE:
<223> OTHER INFORMATION: Peptide fragment

<400> SEQUENCE: 105

Lys Ser Ile Ala Tyr Leu Gln Met Asn Ser Leu Lys Thr Glu Asp Thr
1               5                   10                  15

Ala Leu Tyr Tyr Cys
            20

<210> SEQ ID NO 106
<211> LENGTH: 12
<212> TYPE: PRT
<213> ORGANISM: Artificial Sequence
<220> FEATURE:
<223> OTHER INFORMATION: Peptide fragment general formula
<220> FEATURE:
<221> NAME/KEY: VARIANT
<222> LOCATION: (2)...(2)
<223> OTHER INFORMATION: Xaa = Ser or Asn
<220> FEATURE:
<221> NAME/KEY: VARIANT
<222> LOCATION: (3)...(3)
<223> OTHER INFORMATION: Xaa = Ile, Thr, Ser, Met, Arg, or Asn
<220> FEATURE:
<221> NAME/KEY: VARIANT
<222> LOCATION: (4)...(4)
<223> OTHER INFORMATION: Xaa = Ala, Leu, Val, or Gln
<220> FEATURE:

```
<221> NAME/KEY: VARIANT
<222> LOCATION: (9)...(9)
<223> OTHER INFORMATION: Xaa = Asn, Asp, Ser, Thr or Ala
<220> FEATURE:
<221> NAME/KEY: VARIANT
<222> LOCATION: (10)...(10)
<223> OTHER INFORMATION: Xaa = Ser, Thr, or Asn

<400> SEQUENCE: 106

Lys Xaa Xaa Xaa Tyr Leu Gln Met Xaa Xaa Leu Lys
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Illustrative spacer peptide sequence

<400> SEQUENCE: 107

Glu Gly Lys Ser Ser Gly Ser Gly Ser Glu Ser Lys Val Asp
1               5                   10

<210> SEQ ID NO 108
<211> LENGTH: 18
<212> TYPE: PRT
<213> ORGANISM: Artificial Sequence
<220> FEATURE:
<223> OTHER INFORMATION: Illustrative spacer peptide sequence

<400> SEQUENCE: 108

Lys Glu Ser Gly Ser Val Ser Ser Glu Gln Leu Ala Gln Phe Arg Ser
1               5                   10                  15

Leu Asp

<210> SEQ ID NO 109
<211> LENGTH: 5
<212> TYPE: PRT
<213> ORGANISM: Artificial Sequence
<220> FEATURE:
<223> OTHER INFORMATION: Flexible polylinker peptide sequence

<400> SEQUENCE: 109

Gly Gly Gly Gly Ser
1               5

<210> SEQ ID NO 110
<211> LENGTH: 6
<212> TYPE: PRT
<213> ORGANISM: Artificial Sequence
<220> FEATURE:
<223> OTHER INFORMATION: Peptide sequence

<400> SEQUENCE: 110

Glu Val Gln Leu Val Glu
1               5

<210> SEQ ID NO 111
<211> LENGTH: 6
<212> TYPE: PRT
<213> ORGANISM: Artificial Sequence
<220> FEATURE:
<223> OTHER INFORMATION: Peptide sequence

<400> SEQUENCE: 111

Asp Val Gln Leu Leu Glu
1               5
```

<210> SEQ ID NO 112
<211> LENGTH: 463
<212> TYPE: PRT
<213> ORGANISM: Homo sapiens

<400> SEQUENCE: 112

```
Met Glu Phe Gly Leu Ser Trp Val Phe Leu Val Ala Ile Leu Lys Gly
1               5                   10                  15

Val Gln Cys Glu Val Lys Leu Val Glu Ser Gly Gly Gly Leu Val Gln
            20                  25                  30

Pro Gly Arg Ser Leu Arg Leu Ser Cys Thr Ser Ser Gly Phe Thr Phe
        35                  40                  45

Gly Asp Tyr Ala Met Asn Trp Val Arg Gln Ala Pro Gly Lys Gly Leu
    50                  55                  60

Glu Trp Val Gly Phe Ile Arg Ser Lys Pro Tyr Gly Gly Thr Thr Glu
65                  70                  75                  80

Tyr Ala Ala Ser Leu Lys Gly Arg Phe Thr Val Ser Arg Asp Asp Ser
                85                  90                  95

Lys Ser Ile Ala Tyr Leu Gln Met Asn Ser Leu Lys Thr Glu Asp Thr
            100                 105                 110

Ala Leu Tyr Tyr Cys Thr Arg Ser Leu Arg Gly Val Gln Gln Pro Leu
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Thr Ile
            340                 345                 350

Ser Lys Ala Lys Gly Gly Pro Arg Glu Pro Gln Val Tyr Thr Leu Pro
        355                 360                 365

Pro Ser Arg Asp Glu Leu Thr Lys Asn Gln Val Ser Leu Thr Cys Leu
```

```
                    370                 375                 380
Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro Gly Lys
                450                 455                 460

<210> SEQ ID NO 113
<211> LENGTH: 471
<212> TYPE: PRT
<213> ORGANISM: Homo sapiens

<400> SEQUENCE: 113

Met Glu Phe Gly Leu Ser Trp Val Phe Leu Val Ala Ile Leu Lys Gly
1               5                   10                  15

Val Gln Cys Glu Val Lys Leu Val Glu Ser Gly Gly Gly Leu Val Gln
                20                  25                  30

Pro Gly Arg Ser Leu Arg Leu Ser Cys Thr Ser Ser Gly Phe Thr Phe
            35                  40                  45

Gly Asp Tyr Ala Met Asn Trp Val Arg Gln Ala Pro Gly Lys Gly Leu
        50                  55                  60

Glu Trp Val Gly Phe Ile Arg Ser Lys Pro Tyr Gly Gly Thr Thr Glu
65                  70                  75                  80

Tyr Ala Ala Ser Leu Lys Gly Arg Phe Thr Val Ser Arg Asp Asp Ser
                85                  90                  95

Lys Ser Ile Ala Tyr Leu Gln Met Asn Ser Leu Lys Thr Glu Asp Thr
                100                 105                 110

Ala Leu Tyr Tyr Cys Thr Arg Ser Leu Arg Gly Val Gln Gln Pro Leu
            115                 120                 125

Asp Tyr Trp Gly Gln Gly Thr Leu Val Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285
```

```
Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gly Pro Arg
        355                 360                 365

Glu Pro Gln Val Tyr Thr Leu Pro Pro Ser Arg Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 114
<211> LENGTH: 459
<212> TYPE: PRT
<213> ORGANISM: Homo sapiens

<400> SEQUENCE: 114

Met Glu Phe Gly Leu Ser Trp Val Phe Leu Val Ala Ile Leu Lys Gly
1               5                   10                  15

Val Gln Cys Asp Val Gln Leu Leu Glu Ser Gly Gly Gly Leu Val Gln
            20                  25                  30

Pro Gly Gly Ser Leu Arg Leu Ser Cys Thr Ser Ser Gly Phe Thr Phe
        35                  40                  45

Gly Asp Tyr Ala Met Asn Trp Val Arg Gln Ala Pro Gly Lys Gly Leu
    50                  55                  60

Glu Trp Val Gly Phe Ile Arg Ser Lys Pro Tyr Gly Gly Thr Thr Glu
65                  70                  75                  80

Tyr Ala Ala Ser Leu Lys Gly Arg Phe Thr Val Ser Arg Asp Asp Ser
                85                  90                  95

Lys Ser Ile Ala Tyr Leu Gln Met Asn Ser Leu Lys Thr Glu Asp Thr
            100                 105                 110

Ala Leu Tyr Tyr Cys Thr Arg Ser Leu Arg Gly Val Gln Gln Pro Leu
        115                 120                 125

Asp Tyr Trp Gly Gln Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190
```

```
Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gly Pro Arg Glu Pro Gln Val Tyr Thr Leu Pro Pro Ser Arg Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 115
<211> LENGTH: 459
<212> TYPE: PRT
<213> ORGANISM: Homo sapiens

<400> SEQUENCE: 115

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Thr Ser Gly Phe Thr Phe
        35                  40                  45

Gly Asp Tyr Ala Met Asn Trp Val Arg Gln Ala Pro Gly Lys Gly Leu
    50                  55                  60

Glu Trp Val Gly Phe Ile Arg Ser Lys Pro Tyr Gly Gly Thr Thr Glu
65                  70                  75                  80

Tyr Ala Ala Ser Leu Lys Gly Arg Phe Thr Val Ser Arg Asp Asp Ser
                85                  90                  95

Lys Ser Ile Ala Tyr Leu Gln Met Asn Ser Leu Lys Thr Glu Asp Thr
```

```
                    100                 105                 110
Ala Leu Tyr Tyr Cys Thr Arg Ser Leu Arg Gly Val Gln Gln Pro Leu
            115                 120                 125

Asp Tyr Trp Gly Gln Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
            195                 200                 205

Thr Tyr Ile Cys Asn Val Asn His Lys Pro Ser Asn Thr Lys Val Asp
        210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser His Glu Asp Pro Glu Val Lys Phe Asn
            275                 280                 285

Trp Tyr Val Asp Gly Val Glu Val His Asn Ala Lys Thr Lys Pro Arg
        290                 295                 300

Glu Glu Gln Tyr Asn Ser Thr Tyr Arg Val Val Ser Val Leu Tyr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gly Pro Arg Glu Pro Gln Val Tyr Thr Leu Pro Pro Ser Arg Asp
            355                 360                 365

Glu Leu Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
                420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
    450                 455
```